(12) United States Patent
Allen et al.

(10) Patent No.: US 7,255,701 B2
(45) Date of Patent: *Aug. 14, 2007

(54) SYSTEM, METHODS, AND APPARATUSES FOR CLAMPING AND RECLAMPING AN ORTHOPEDIC SURGICAL CABLE

(75) Inventors: C. Wayne Allen, Southaven, MS (US); David C. Kelman, Collierville, TN (US); Jerry L. Jones, Memphis, TN (US)

(73) Assignee: Smith & Nephew, Inc., Memphis, TN (US)

( * ) Notice: Subject to any disclaimer, the term of this patent is extended or adjusted under 35 U.S.C. 154(b) by 385 days.

This patent is subject to a terminal disclaimer.

(21) Appl. No.: 10/456,598

(22) Filed: Jun. 6, 2003

(65) Prior Publication Data
US 2004/0097942 A1 May 20, 2004

Related U.S. Application Data

(63) Continuation-in-part of application No. 10/230,040, filed on Aug. 28, 2002.

(51) Int. Cl.
*A61B 17/56* (2006.01)
(52) U.S. Cl. .................................................. 606/74
(58) Field of Classification Search ............ 606/69–71, 606/72, 74
See application file for complete search history.

(56) References Cited

U.S. PATENT DOCUMENTS

| | | | |
|---|---|---|---|
| 575,631 A | 1/1897 | Brooks | |
| 902,040 A | * 10/1908 | Wyckoff | 403/391 |
| 2,501,978 A | * 3/1950 | Wichman | 606/71 |
| 3,866,607 A | 2/1975 | Forsythe et al. | |
| RE31,628 E | 7/1984 | Allgower et al. | |

(Continued)

FOREIGN PATENT DOCUMENTS

DE 43 43 117 A1 6/1995

(Continued)

OTHER PUBLICATIONS

Brochure entitled Introducing Peak™ Polyaxial Anterior Cervical Plate, by Depuy Motech, one page, undated.

(Continued)

*Primary Examiner*—Eduardo C Robert
*Assistant Examiner*—Mary Hoffman
(74) *Attorney, Agent, or Firm*—Kilpatrick Stockton LLP

(57) ABSTRACT

Systems, methods, and apparatuses for clamping and reclamping an orthopedic surgical cable used in conjunction with an orthopedic implant device, a bone, and/or bone implant or structure. A sequence for a method in accordance with various embodiments the invention includes providing a surgical cable clamp and an orthopedic surgical cable. Next, mounting a portion of the surgical cable to the surgical cable clamp. Next, applying a force to the portion of the surgical cable so that the surgical cable is restrained or secured relative to the surgical cable clamp with a first tension in the surgical cable. Then releasing the force on the extended portion of the surgical cable so that the surgical cable can be repositioned relative to the surgical cable clamp. Finally, applying another force to the extended portion of the surgical cable so that the surgical cable is again restrained or secured relative to the surgical cable clamp.

22 Claims, 20 Drawing Sheets

U.S. PATENT DOCUMENTS

| | | | |
|---|---|---|---|
| 4,484,570 | A | 11/1984 | Sutter et al. |
| 5,085,660 | A | 2/1992 | Lin |
| 5,275,601 | A | 1/1994 | Gogolewski et al. |
| 5,312,410 | A | 5/1994 | Miller et al. |
| 5,324,291 | A | 6/1994 | Ries et al. |
| 5,395,374 | A | 3/1995 | Miller et al. |
| 5,415,658 | A | 5/1995 | Kilpela et al. |
| 5,423,820 | A | 6/1995 | Miller et al. |
| 5,431,659 | A | 7/1995 | Ross, Jr. et al. |
| 5,470,333 | A | 11/1995 | Ray |
| 5,527,310 | A * | 6/1996 | Cole et al. .................. 606/60 |
| 5,536,127 | A | 7/1996 | Pennig |
| 5,569,253 | A | 10/1996 | Farris et al. |
| 5,601,553 | A | 2/1997 | Trebing et al. |
| 5,665,088 | A | 9/1997 | Gil et al. |
| 5,676,667 | A | 10/1997 | Hausman |
| 5,702,399 | A * | 12/1997 | Kilpela et al. ................ 606/72 |
| 5,709,686 | A | 1/1998 | Talos et al. |
| 5,788,697 | A | 8/1998 | Kilpela et al. |
| 5,893,856 | A | 4/1999 | Jacob et al. |
| 5,902,305 | A | 5/1999 | Beger et al. |
| 5,935,130 | A | 8/1999 | Kipela et al. |
| 5,935,133 | A | 8/1999 | Wagner et al. |
| 5,954,722 | A | 9/1999 | Bono |
| 5,964,769 | A | 10/1999 | Wagner et al. |
| 5,968,046 | A | 10/1999 | Castleman |
| 6,053,921 | A | 4/2000 | Wagner et al. |
| 6,129,730 | A | 10/2000 | Bono et al. |
| 6,176,861 | B1 | 1/2001 | Bernstein et al. |
| 6,193,721 | B1 | 2/2001 | Michelson |
| 6,206,881 | B1 | 3/2001 | Frigg et al. |
| 6,235,033 | B1 | 5/2001 | Brace et al. |
| 6,306,136 | B1 | 10/2001 | Baccelli |
| 6,306,140 | B1 | 10/2001 | Siddiqui |
| 6,322,562 | B1 | 11/2001 | Wolter |
| 6,355,043 | B1 | 3/2002 | Adam |
| 6,358,250 | B1 | 3/2002 | Orbay |
| 6,361,537 | B1 | 3/2002 | Anderson |
| 6,364,885 | B1 | 4/2002 | Kilpela et al. |
| 6,391,030 | B1 | 5/2002 | Wagner et al. |
| 6,413,259 | B1 | 7/2002 | Lyons et al. |
| 6,428,542 | B1 | 8/2002 | Michelson |
| 6,440,135 | B2 | 8/2002 | Orbay et al. |
| 6,454,769 | B2 | 9/2002 | Wagner et al. |
| 6,475,218 | B2 | 11/2002 | Gournay et al. |
| 6,506,191 | B1 | 1/2003 | Joos |
| 6,520,965 | B2 | 2/2003 | Chervitz et al. |
| 6,595,994 | B2 | 7/2003 | Kilpela et al. |
| 6,623,486 | B1 | 9/2003 | Weaver et al. |
| 6,682,533 | B1 * | 1/2004 | Dinsdale et al. ............... 606/74 |
| 6,730,091 | B1 | 5/2004 | Pfefferle et al. |
| 6,821,278 | B2 | 11/2004 | Frigg et al. |
| 6,960,213 | B2 | 11/2005 | Chervitz et al. |
| 2001/0037112 | A1 | 11/2001 | Brace et al. |
| 2001/0047174 | A1 | 11/2001 | Donno et al. |
| 2002/0045901 | A1 | 4/2002 | Wagner et al. |
| 2002/0058940 | A1 | 5/2002 | Frigg et al. |
| 2002/0058943 | A1 | 5/2002 | Kilpela et al. |
| 2002/0143338 | A1 | 10/2002 | Orbay et al. |
| 2003/0018335 | A1 | 1/2003 | Michelson |
| 2004/0044345 | A1 | 3/2004 | DeMoss et al. |
| 2004/0073218 | A1 | 4/2004 | Dahners |
| 2004/0087954 | A1 | 5/2004 | Allen et al. |
| 2004/0138666 | A1 | 7/2004 | Molz, IV et al. |
| 2004/0199169 | A1 | 10/2004 | Koons et al. |
| 2005/0070904 | A1 | 3/2005 | Gerlach |
| 2005/0107796 | A1 | 5/2005 | Gerlach et al. |

FOREIGN PATENT DOCUMENTS

| | | |
|---|---|---|
| EP | 0 355 035 B1 | 2/1990 |
| EP | 0 486 762 B1 | 5/1995 |
| EP | 0 468 192 B1 | 9/1996 |
| EP | 0 760 632 B1 | 3/1997 |
| EP | 1169971 | 1/2002 |
| WO | WO 01/19267 A1 | 3/2001 |
| WO | WO 01/91660 | 12/2001 |
| WO | WO 02/058574 | 8/2002 |
| WO | WO 02/096309 A1 | 12/2002 |

OTHER PUBLICATIONS

Brochure entitled Introducing the Profile™ Anterior Thoracolumbar Compression Plate, by Dupuy Motech, one page, undated.

Baumgaertel, et al., "Fracture healing in biological plate osteosynthesis," *Injury*, 29(Supp. 3):S-C3-S-C6 (1998).

Bolhofner, et al., "The Results of Open Reduction and Internal Fixation of Distal Femur Fractures Using a Biologic (Indirect) Reduction Technique," *Journal of Orthopaedic Trauma*, 10(6):371-377 (1996).

Farouk, et al., "Minimally invasive plate osteosynthesis and vascularity: preliminary results of a cadaver injection study," *Injury*, 28(Supp. 1):S-A7-S-A12 (1997).

Farouk, et al., "Minimally Invasive Plate Osteosynthesis: Does Percutaneous Plating Disrupt Femoral Blood Supply Less Than the Traditional Technique?", *Journal of Orthopaedic Trauma*, 13(6):401-406 (1999).

Frigg, et al., "The development of the distal femur Less Invasive Stabilization System (LISS)," *Injury, Int. J. Care Injured*, 32(S-C24-31 (2001).

Frigg, et al. "LCP: The Locking Compression Plate System," *Bone Zone*, undated.

Gerber, et al., "Biological internal fixation of fractures," *Arch. Orthop. Trauma Surg.*, 109:295-303 (1990).

Karnezis, et al., "'Biological' internal fixation of long bone fractures: a biomechanical study of a 'noncontact' plate system," *Injury*, 29(9):689-695 (1998).

Koval, et al., "Distal Femoral Fixation: A Biomechanical Comparison of the Standard Condylar Buttress Plate, a Locked Buttress Plate, and the 95-Degree Blade Plate," Journal of Orthopaedic Trauma, 11(7):521-524 (1997).

Krettek, et al., "Minimally invasive percutaneous plate osteosynthesis (MIPPO) using the DCS in proximal and distal femoral fractures," *Injury*, 28(Supp. 1):S-A20-S-A30 (1997).

Krettek, et al., "Intraoperative control of axes, rotation and length in femoral and tibial fractures," *Injury*, 29(Supp. 3):S-C-29-S-C39 (1998).

Marti, et al., "Biomechanical Evaluation of the Less Invasive Stabilization System for the Internal Fixation of Distal Femur Fractures," *Journal of Orthopaedic Trauma*, 15(7):482-487, 2001.

Miclau, et al., "A Mechanical comparison of the Dynamic Compression Plate, Limited Contact-Dynamic Compression Plate, and Point Contact Fixator," *Journal of Orthopaedic Trauma*, 9(1):17-22 (1995).

Rüedi, et al., "New Techniques in Indirect Reduction of Long Bone Fractures," *Clinical Orthopaedics and Related Research*, No. 347:27-34 (1998).

Schavan, et al., "LISS—The Less Invasive Stabilizaiton System for Metaphyseal Fractures of Femur and Tibia," *OTA 98 Posters* (1998).

Mudgal, et al., 'Plate and Screw Design in Fractures of the Hand and Wrist,' *Clinical Orthopaedics and Related Research*, 445:68-80 (2006).

* cited by examiner

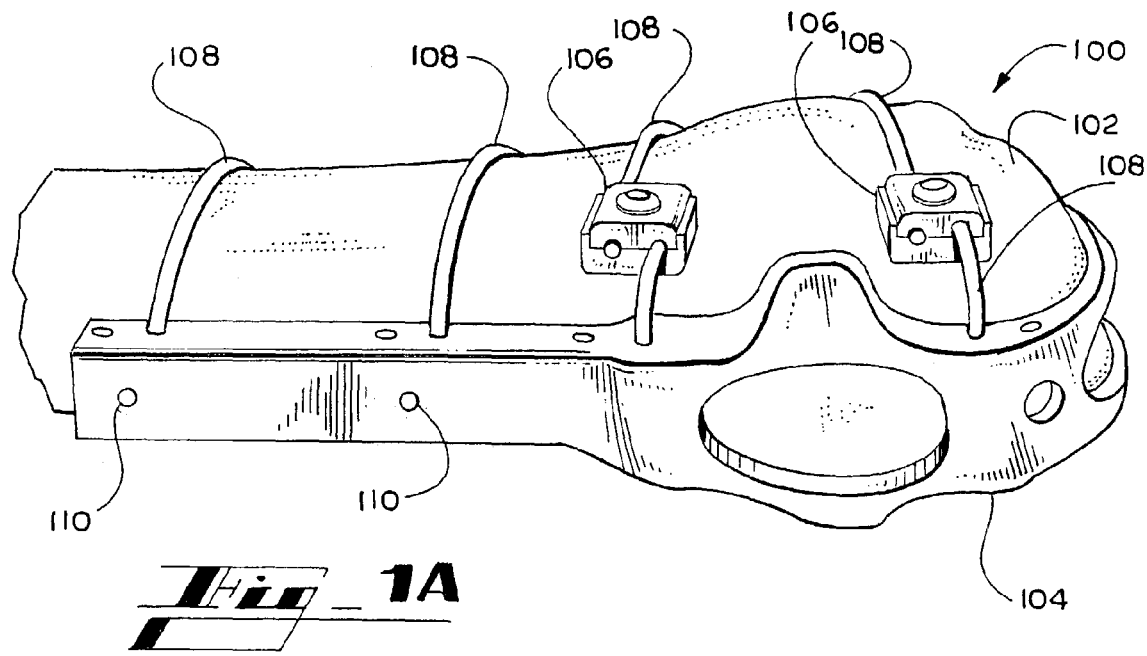
Fig_1A
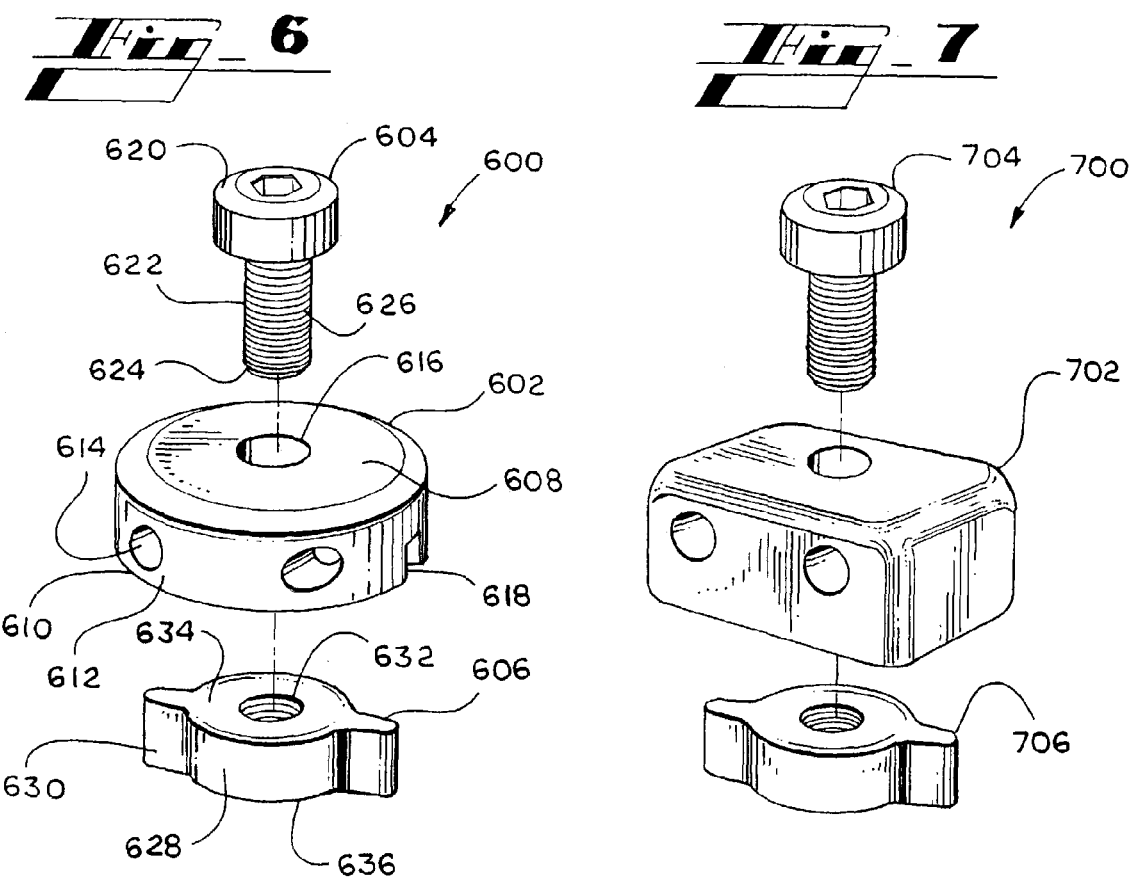
Fig_6
Fig_7

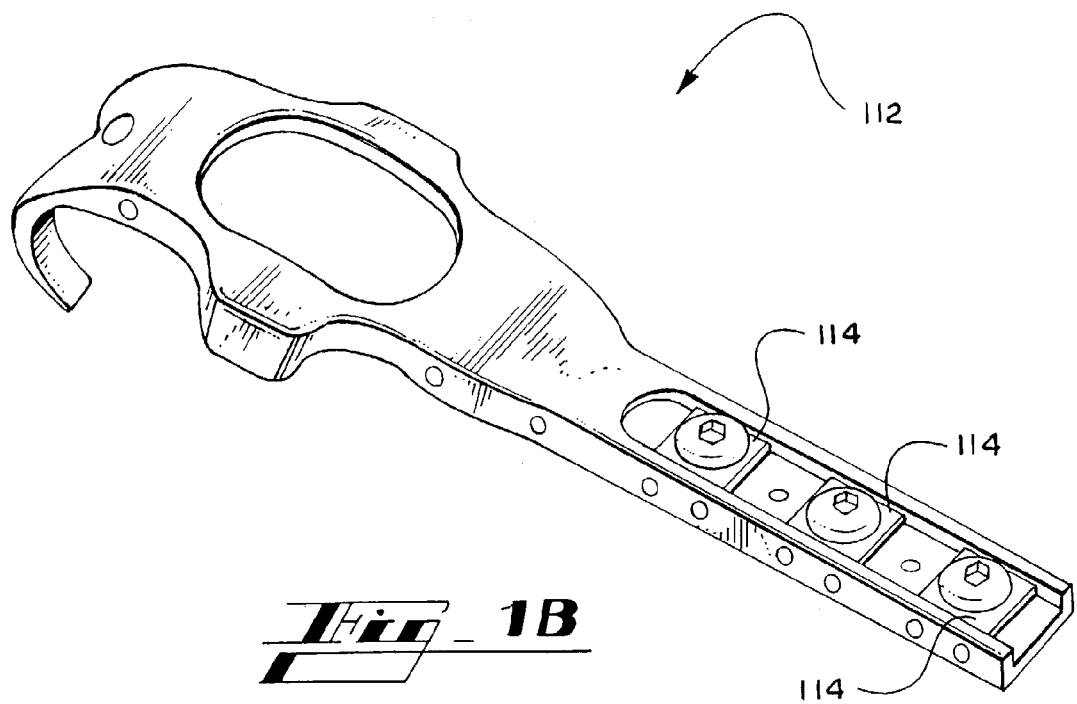
Fig_1B
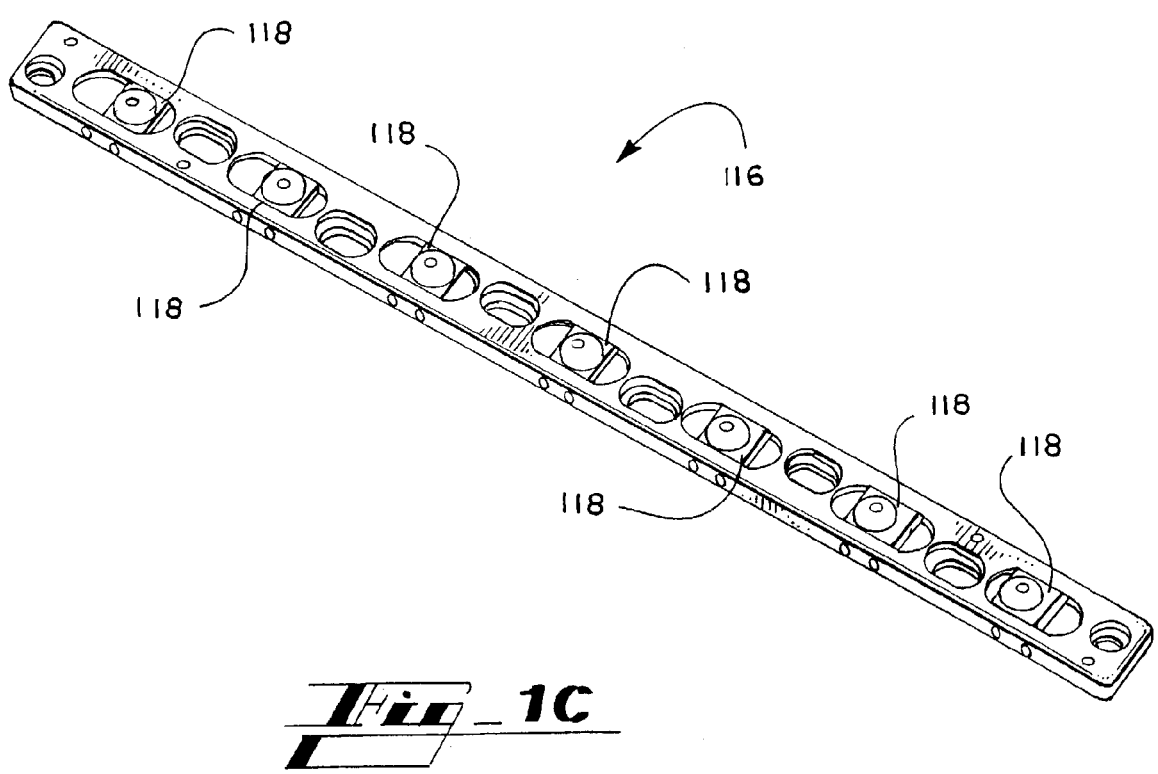
Fig_1C

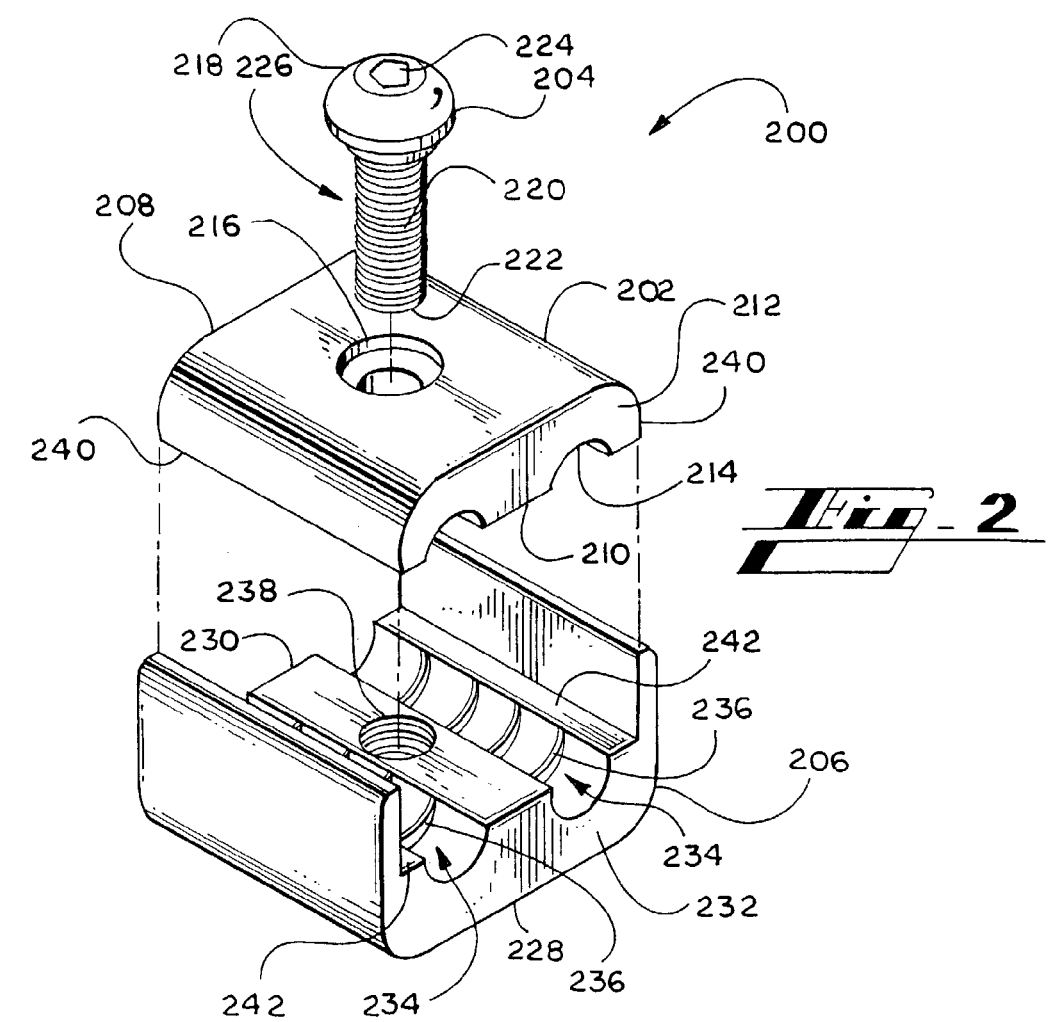
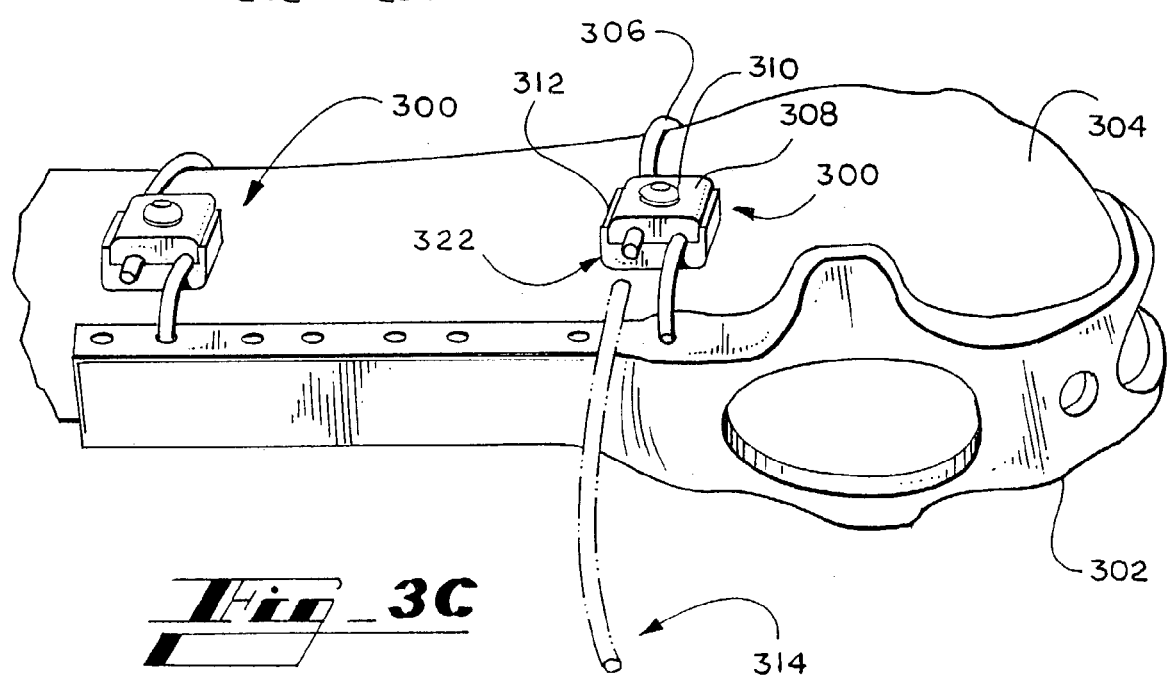

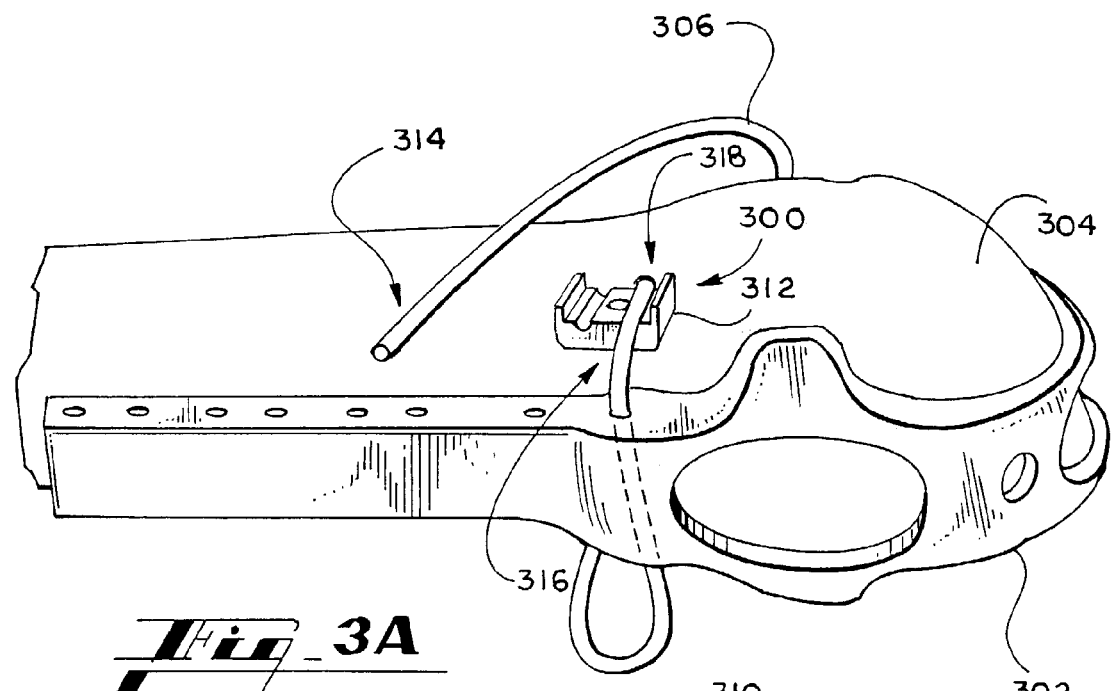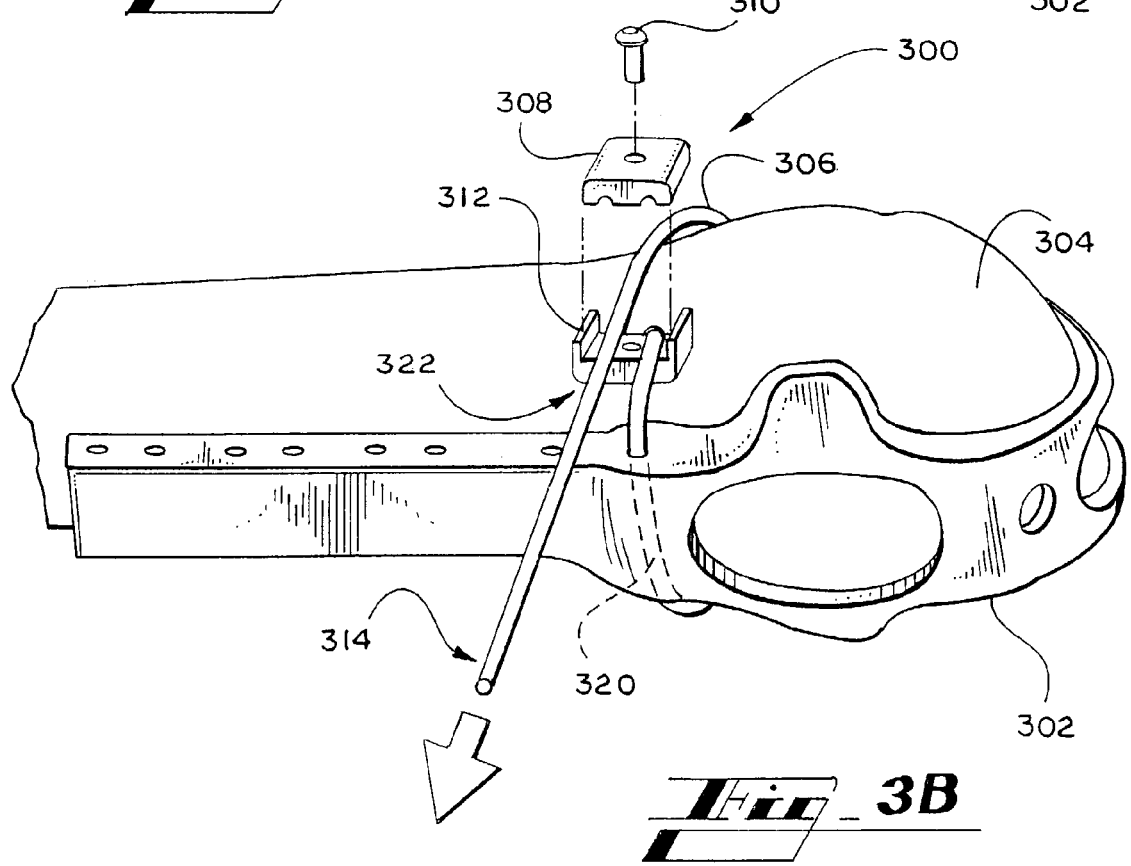

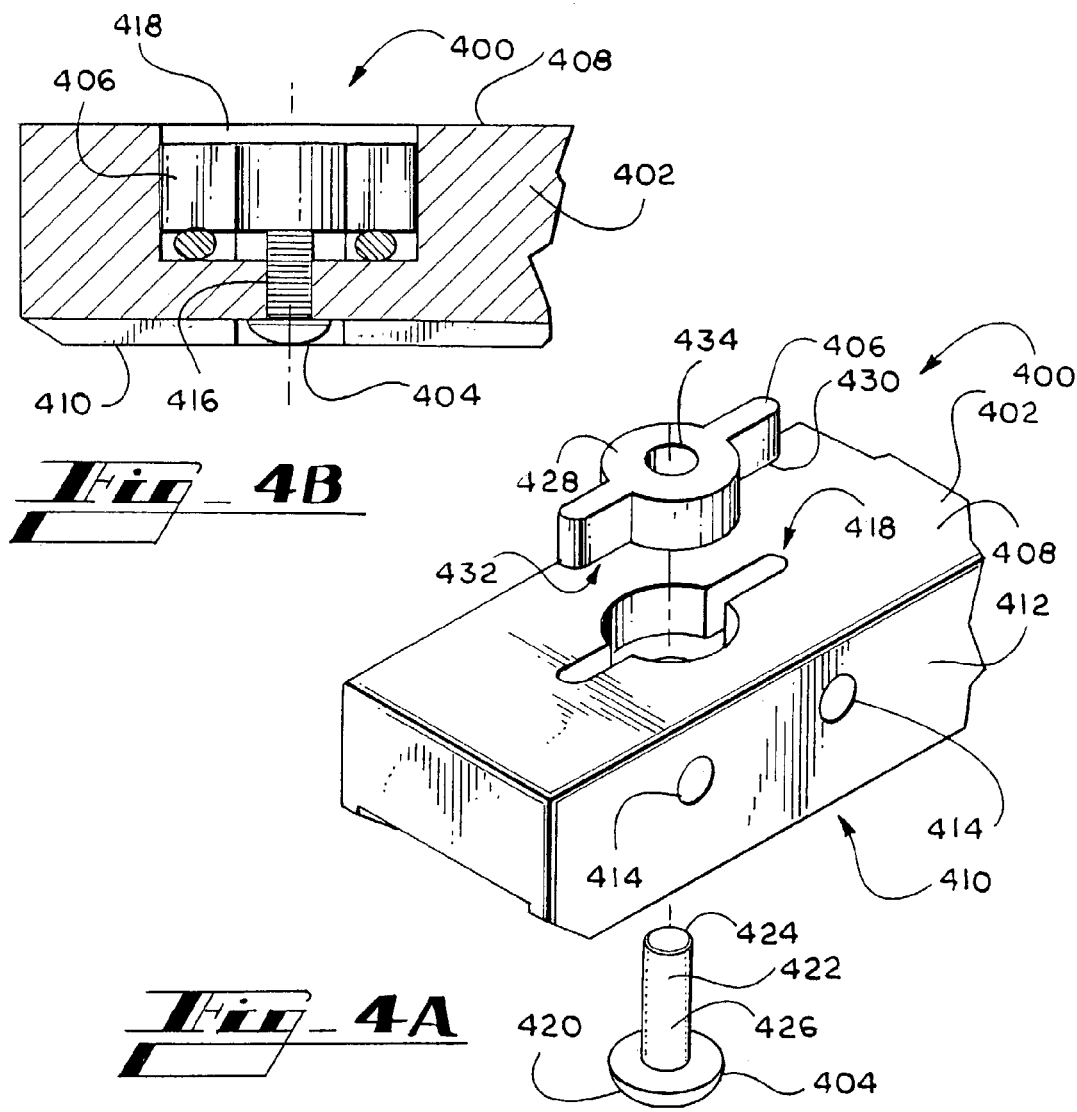
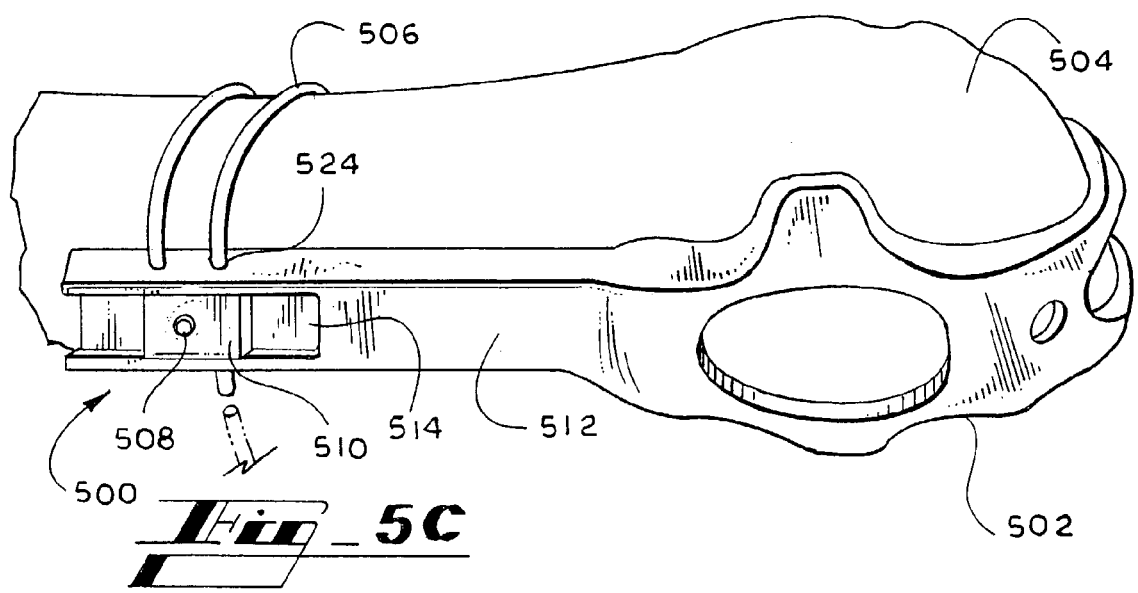

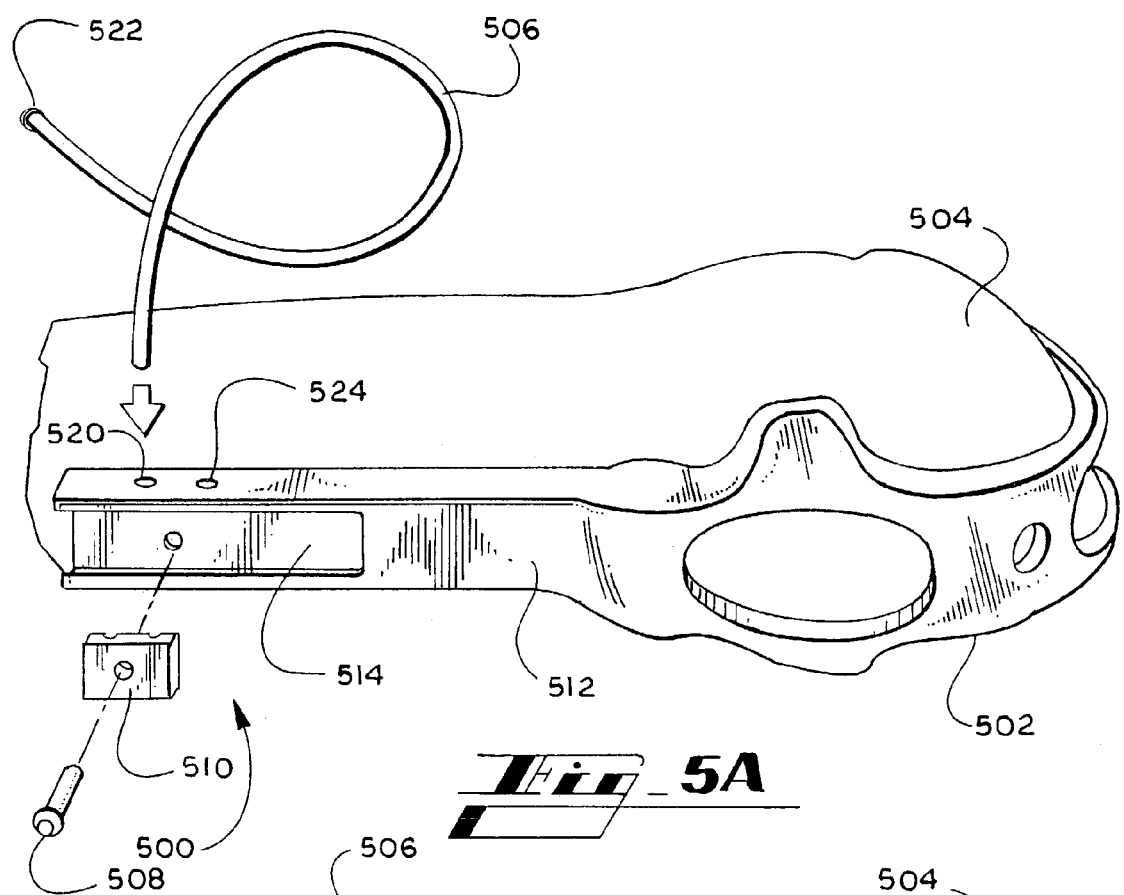
Fig_5A
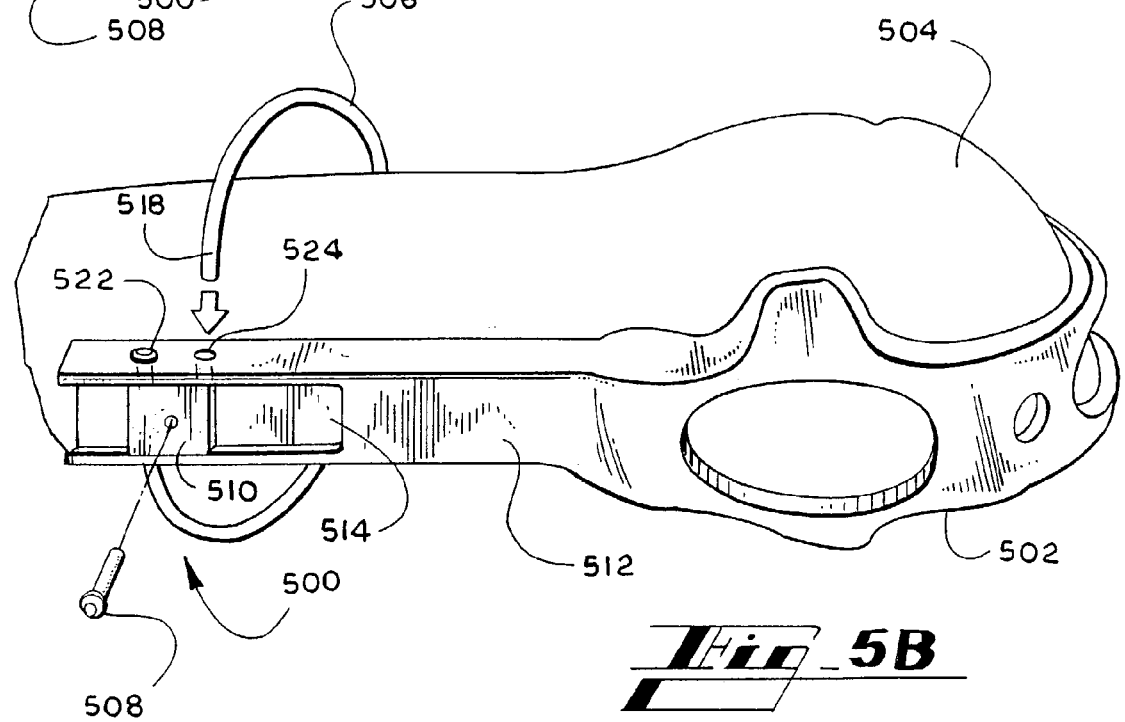
Fig_5B

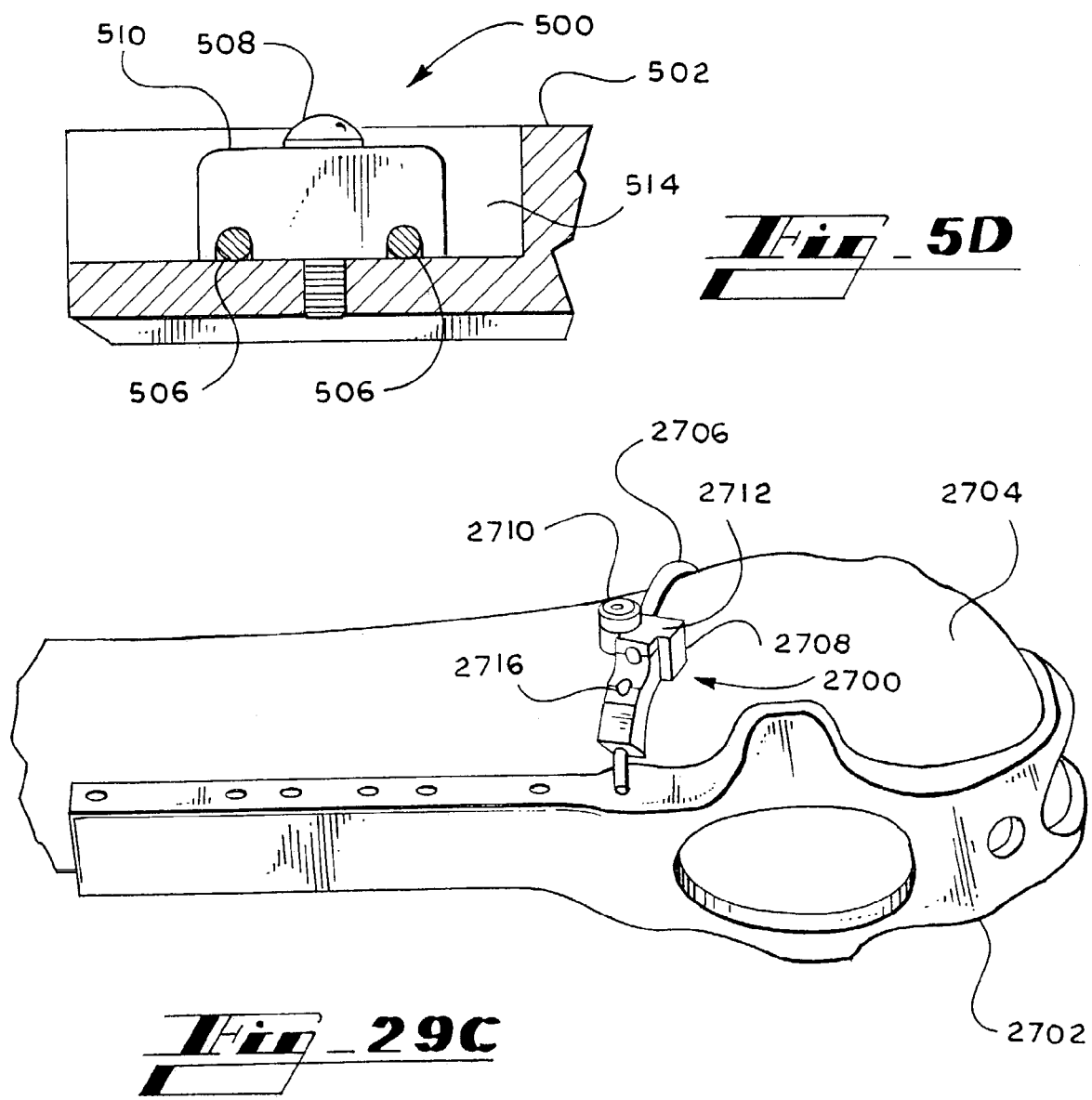

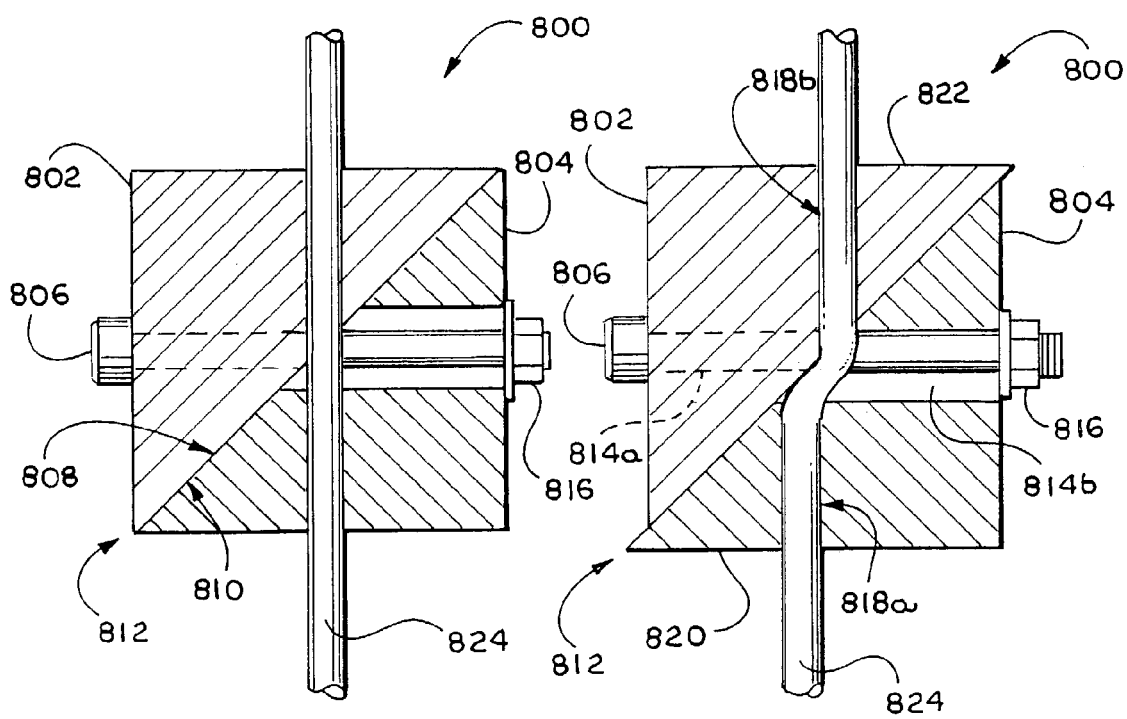
Fig_8A  Fig_8B
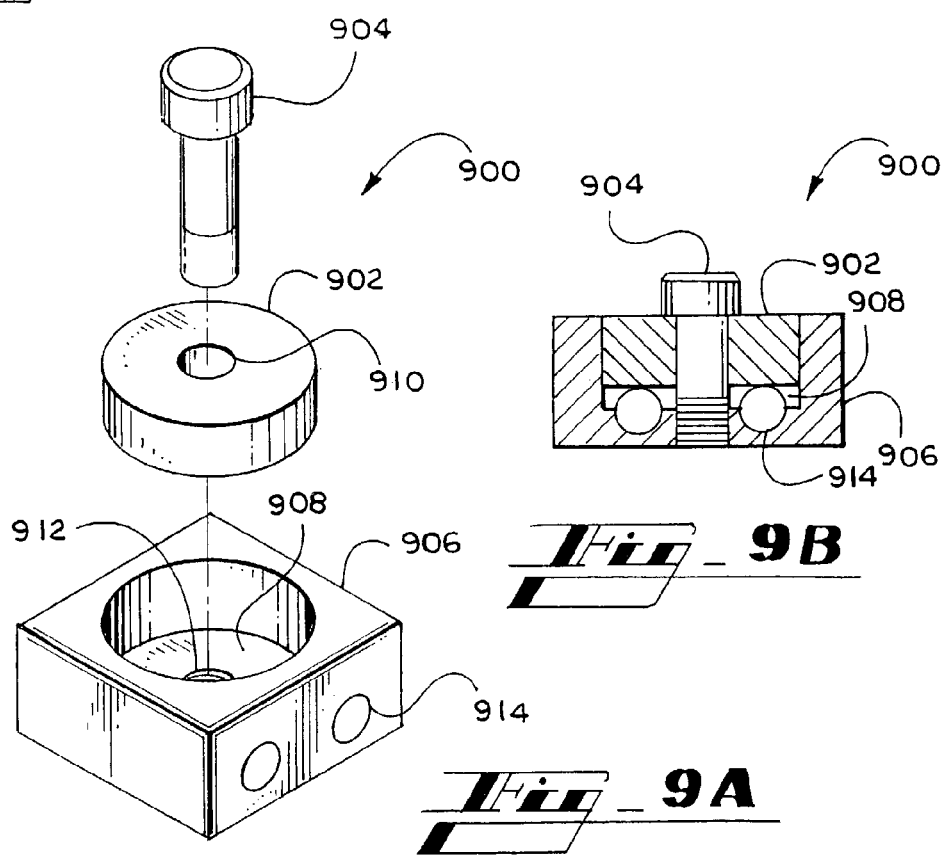
Fig_9B
Fig_9A

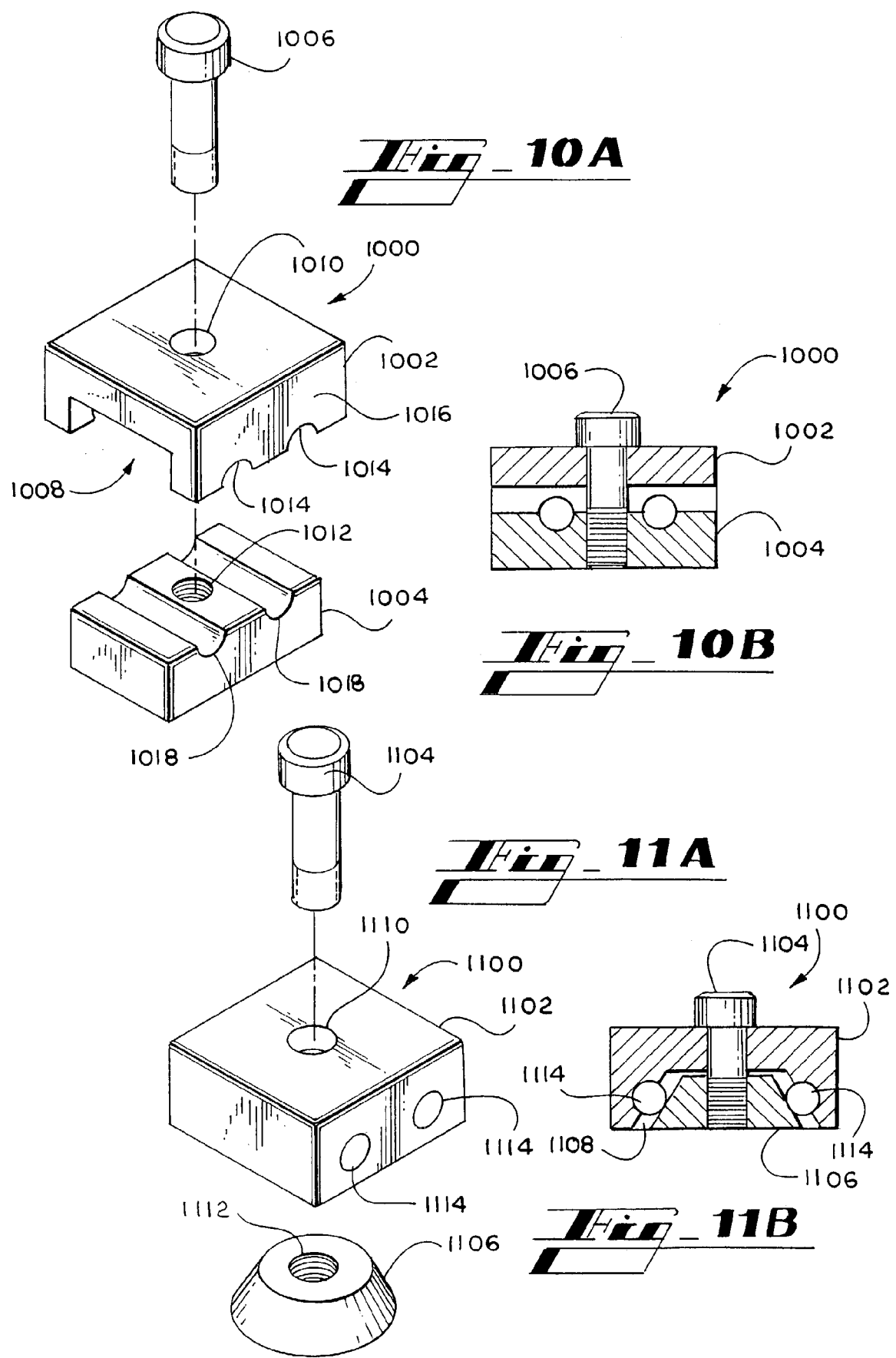

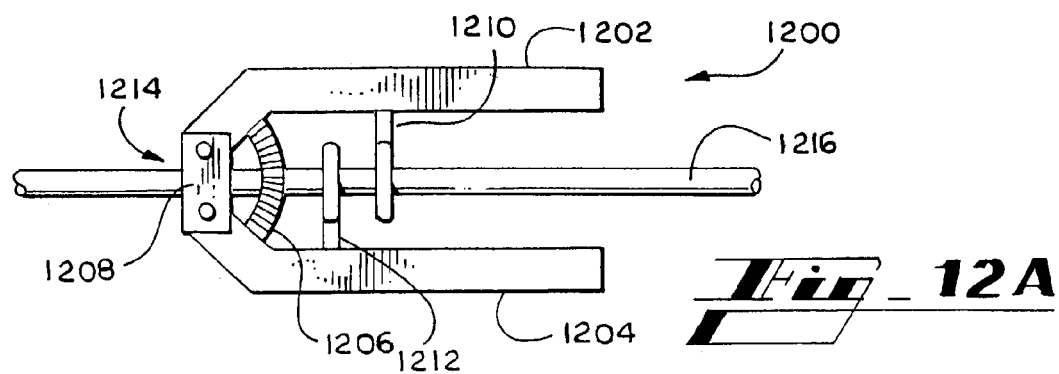
*Fig_12A*
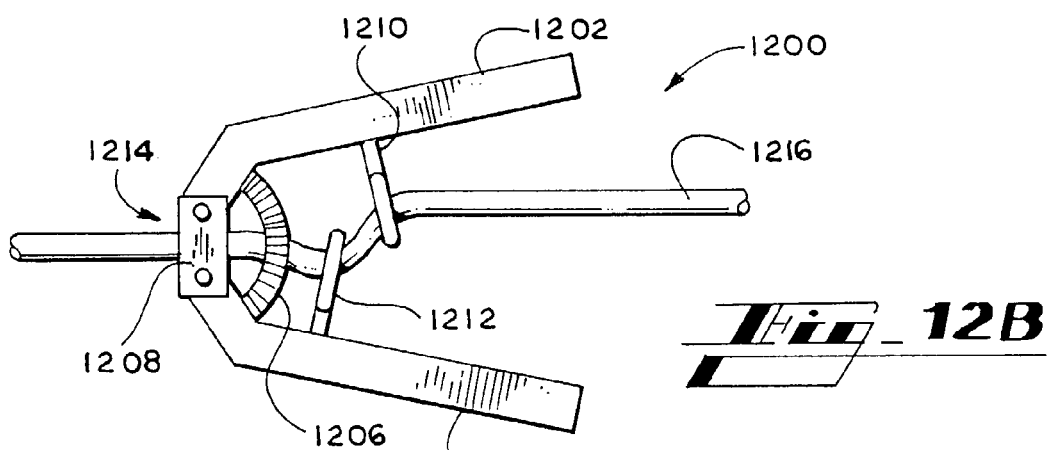
*Fig_12B*
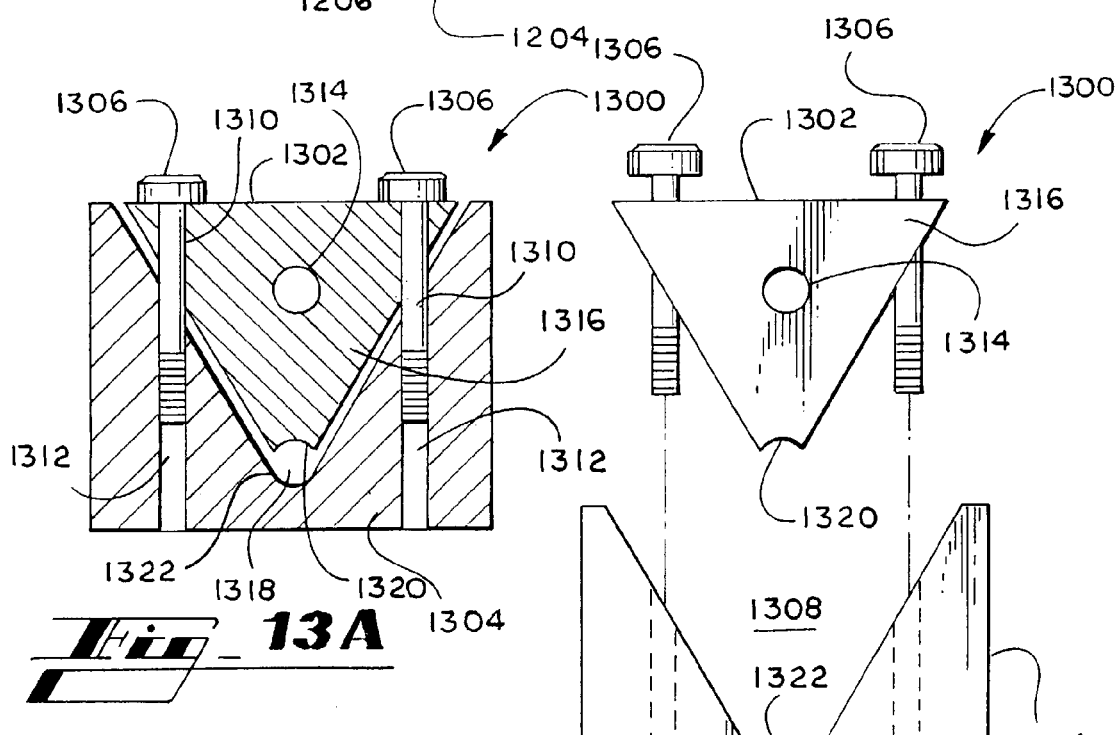
*Fig_13A*
*Fig_13B*

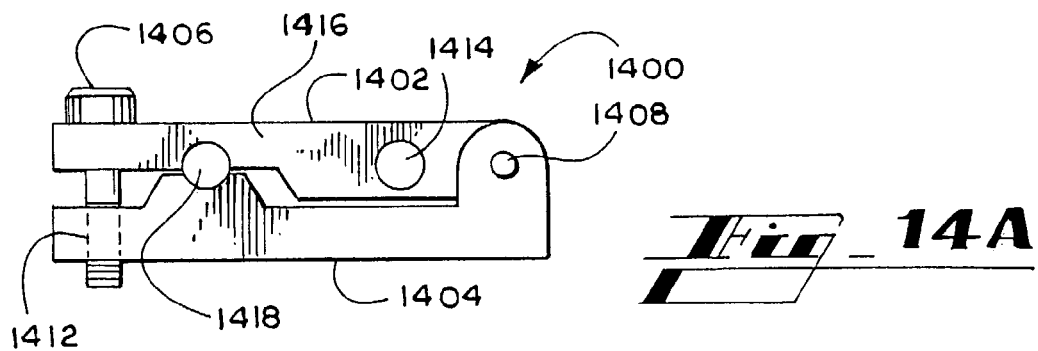
Fig_14A
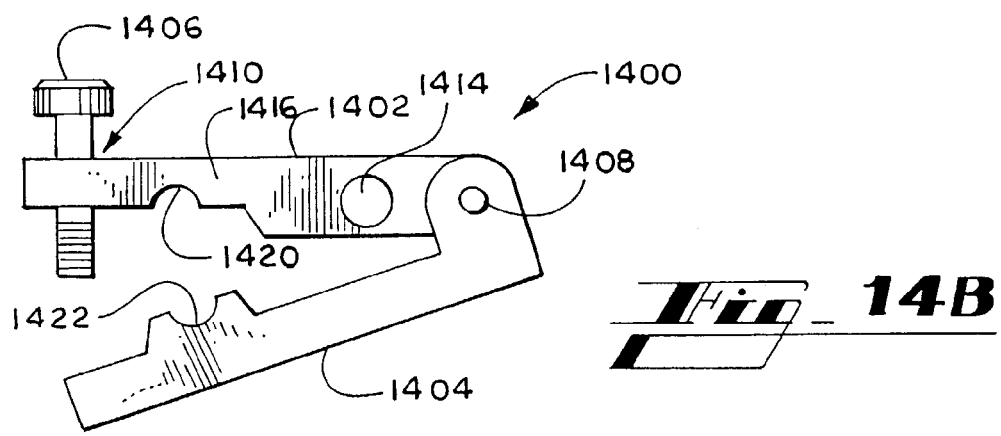
Fig_14B
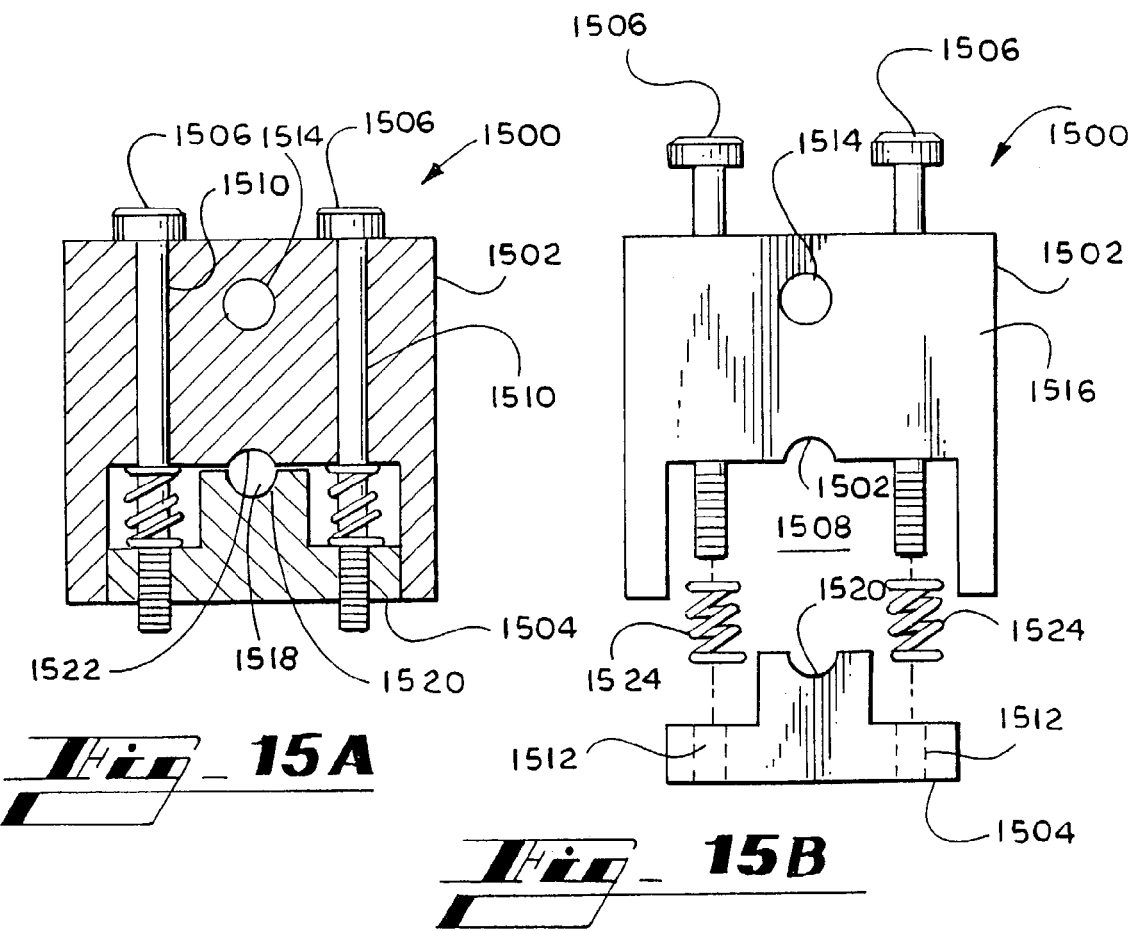
Fig_15A
Fig_15B

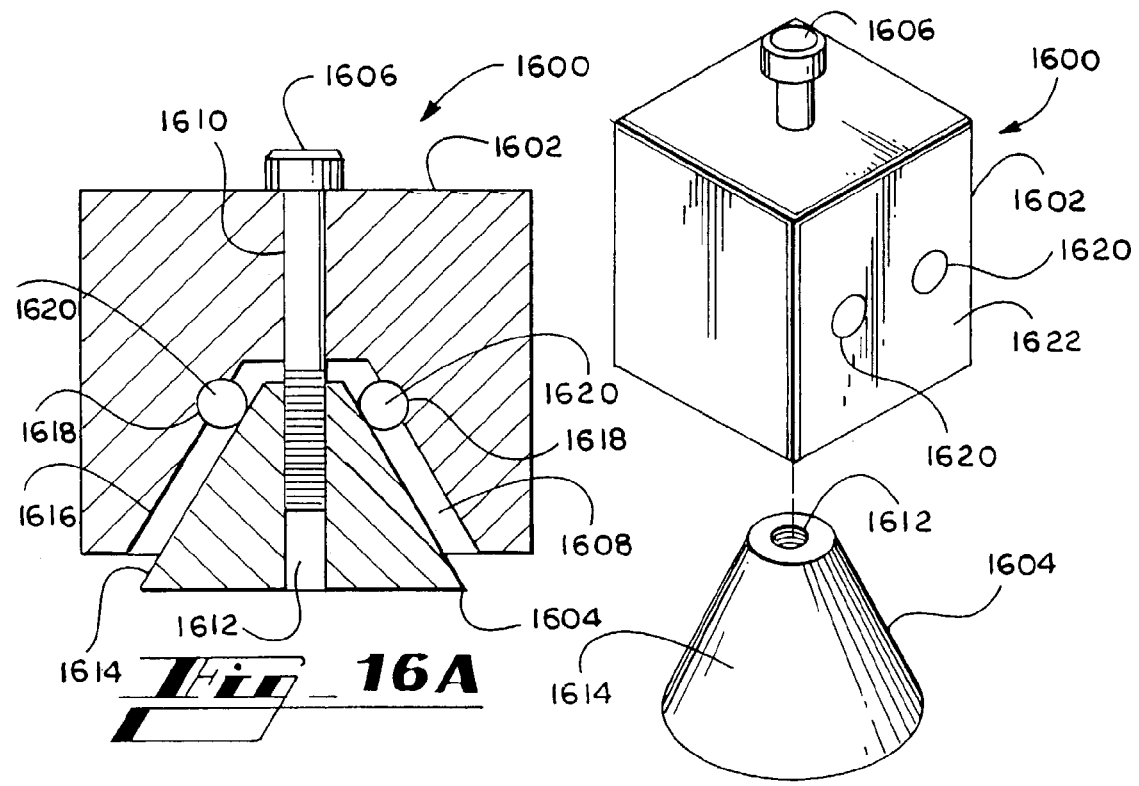
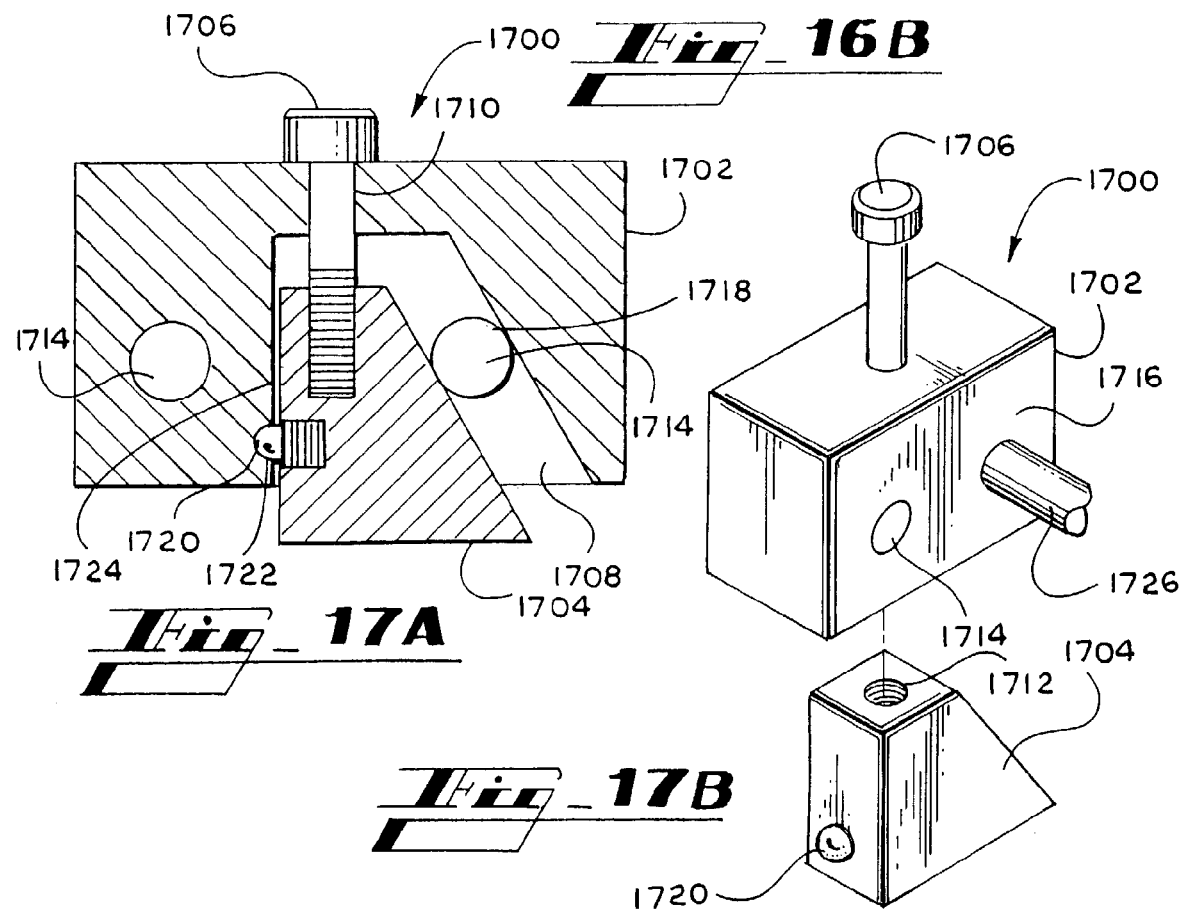

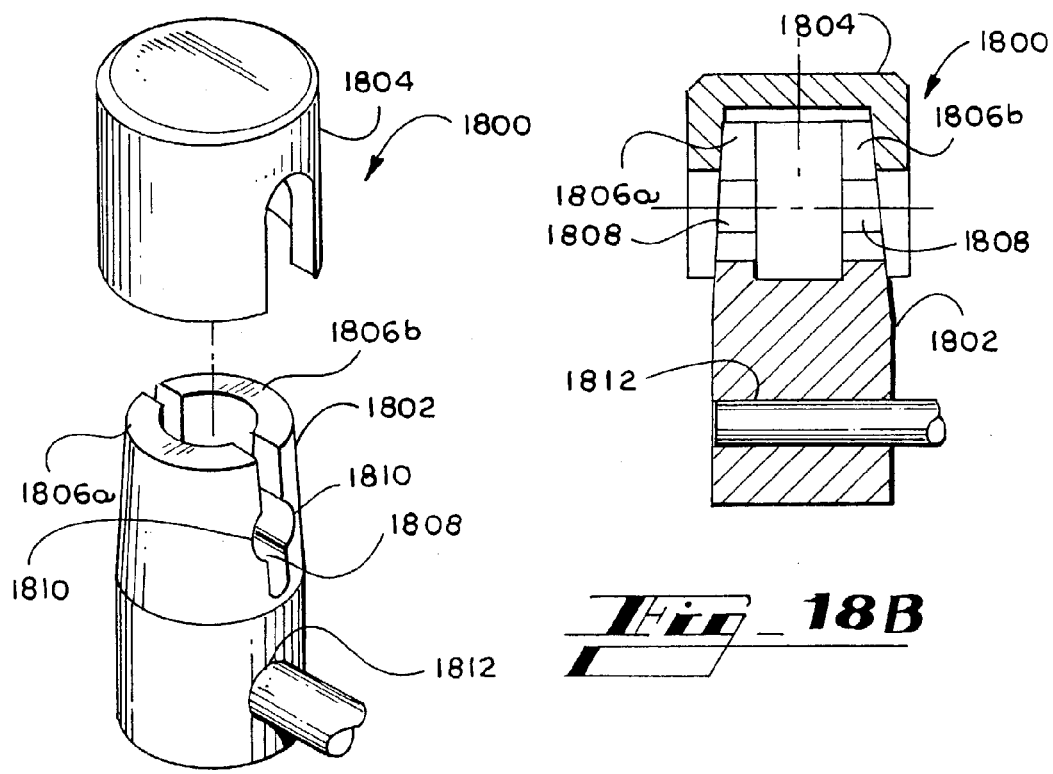
Fig_18A
Fig_18B
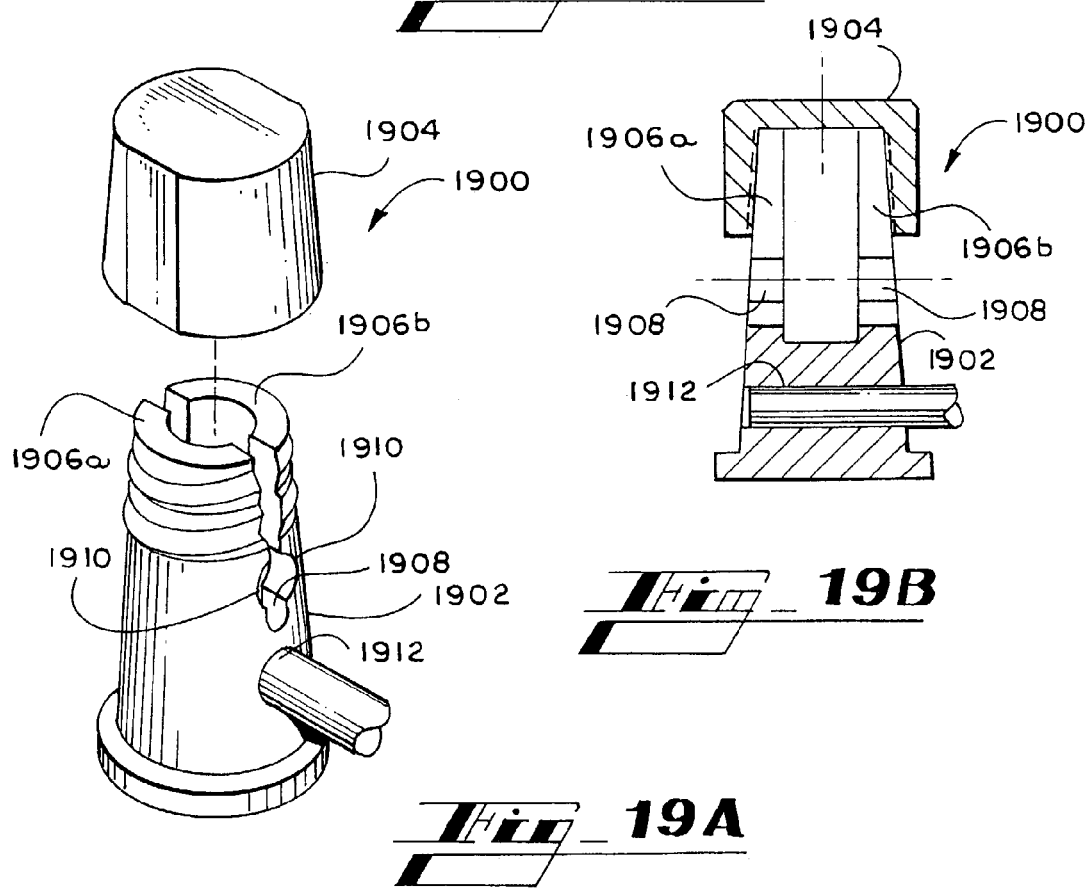
Fig_19A
Fig_19B

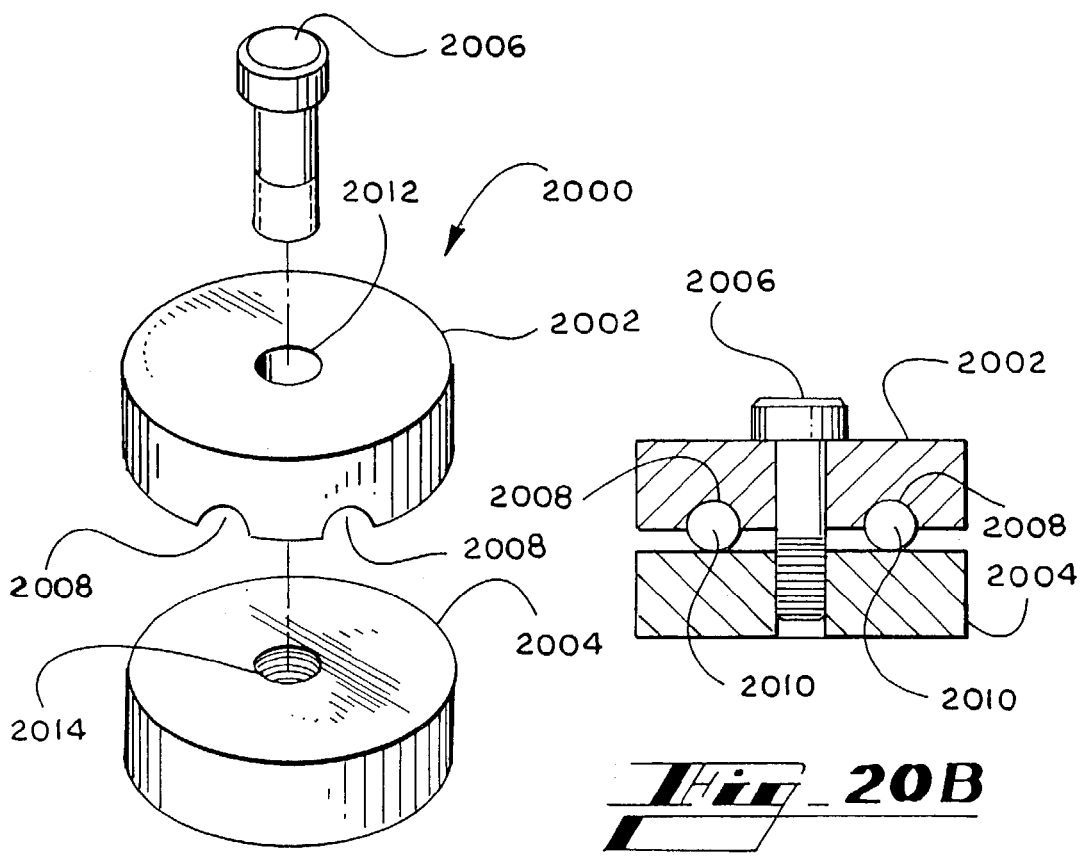
Fig_20A
Fig_20B
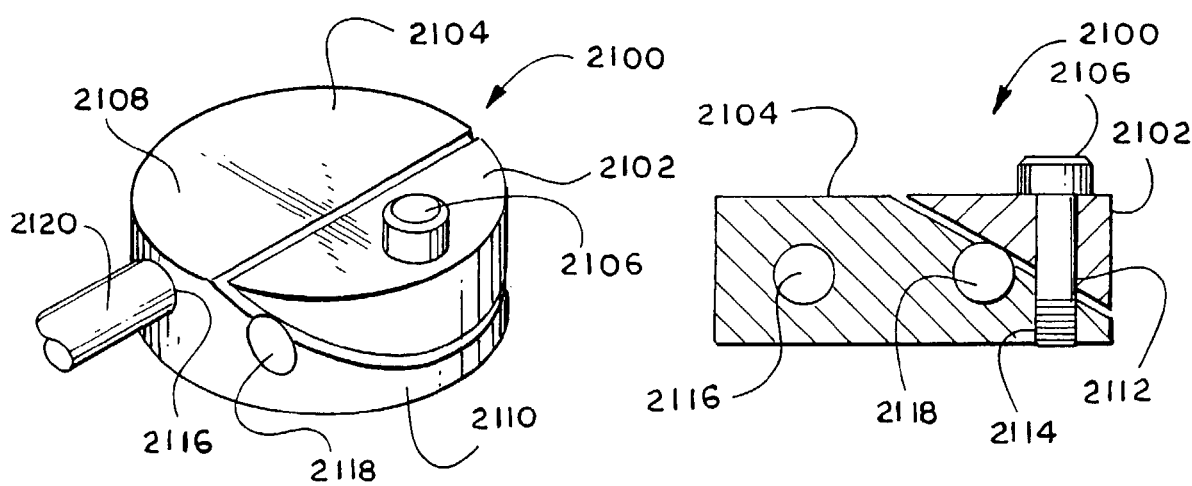
Fig_21A
Fig_21B

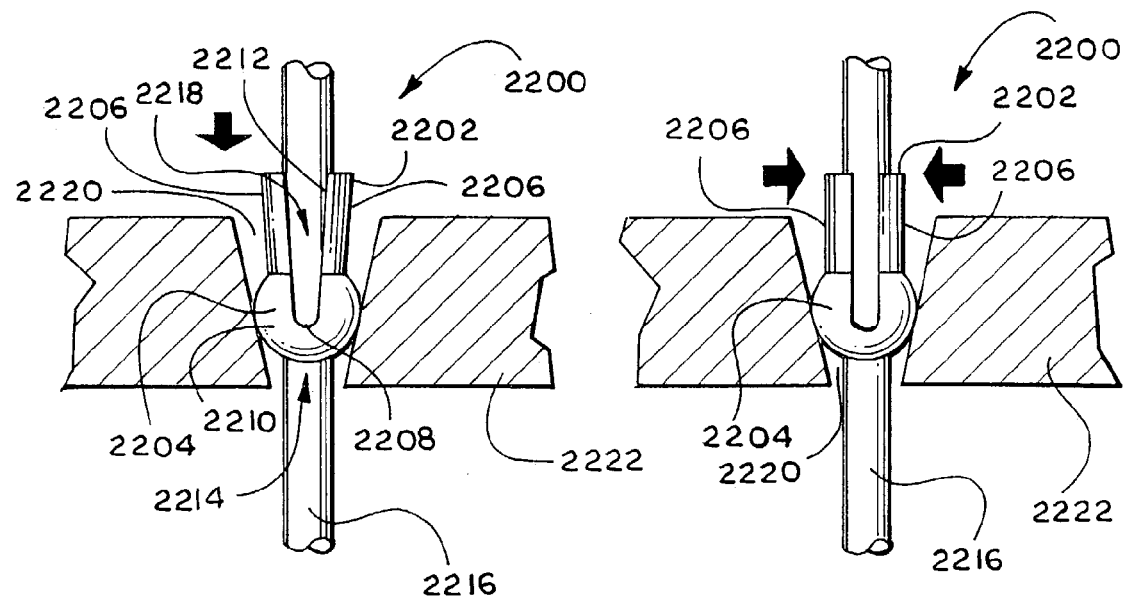
Fig_22A    Fig_22B
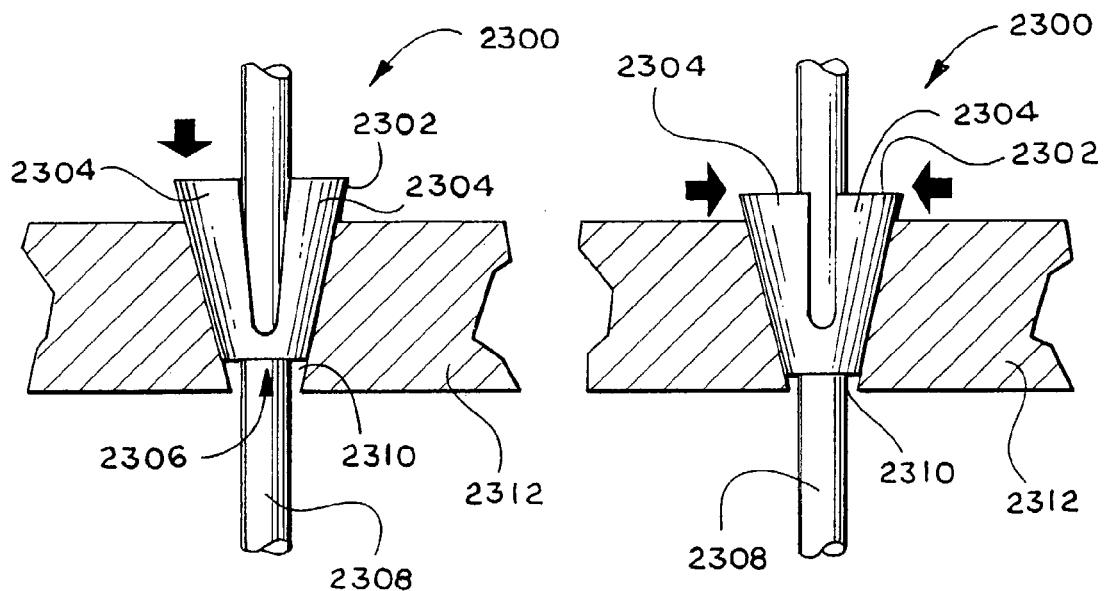
Fig_23A    Fig_23B

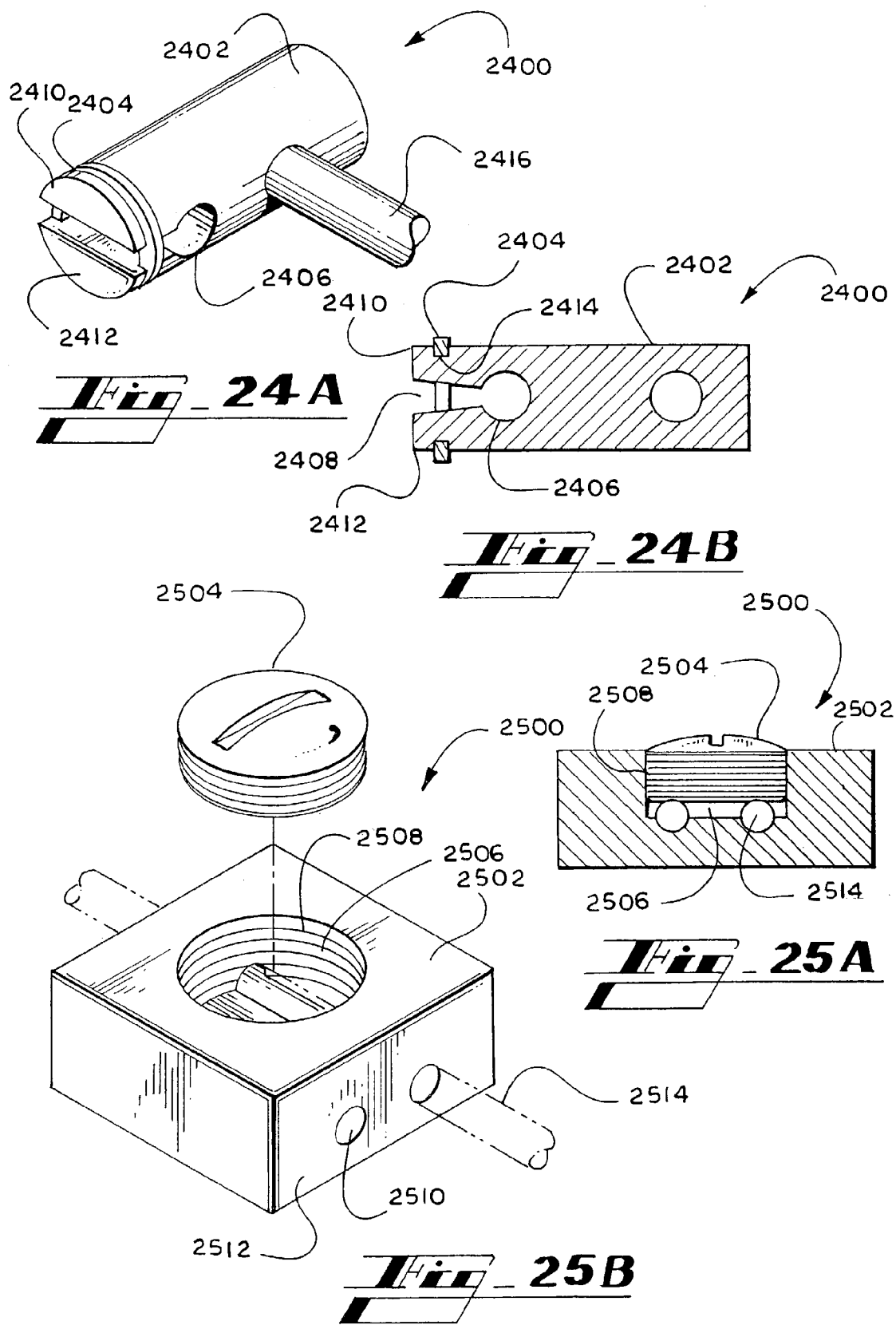

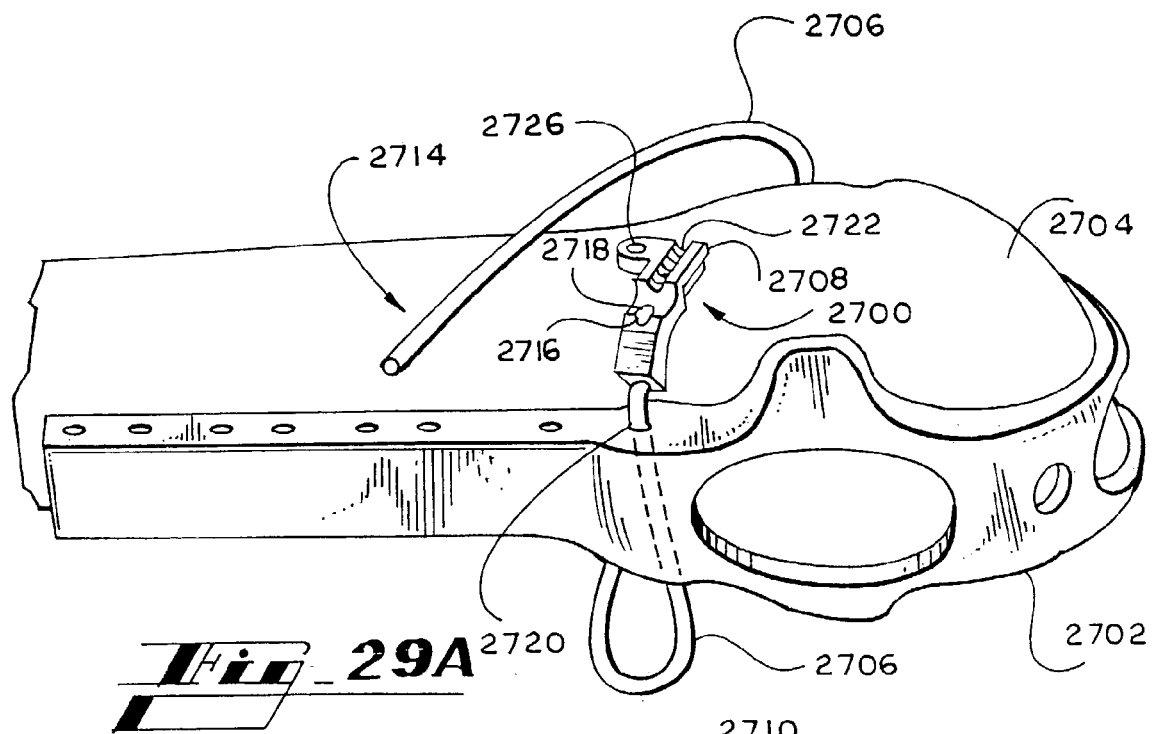
Fig_29A
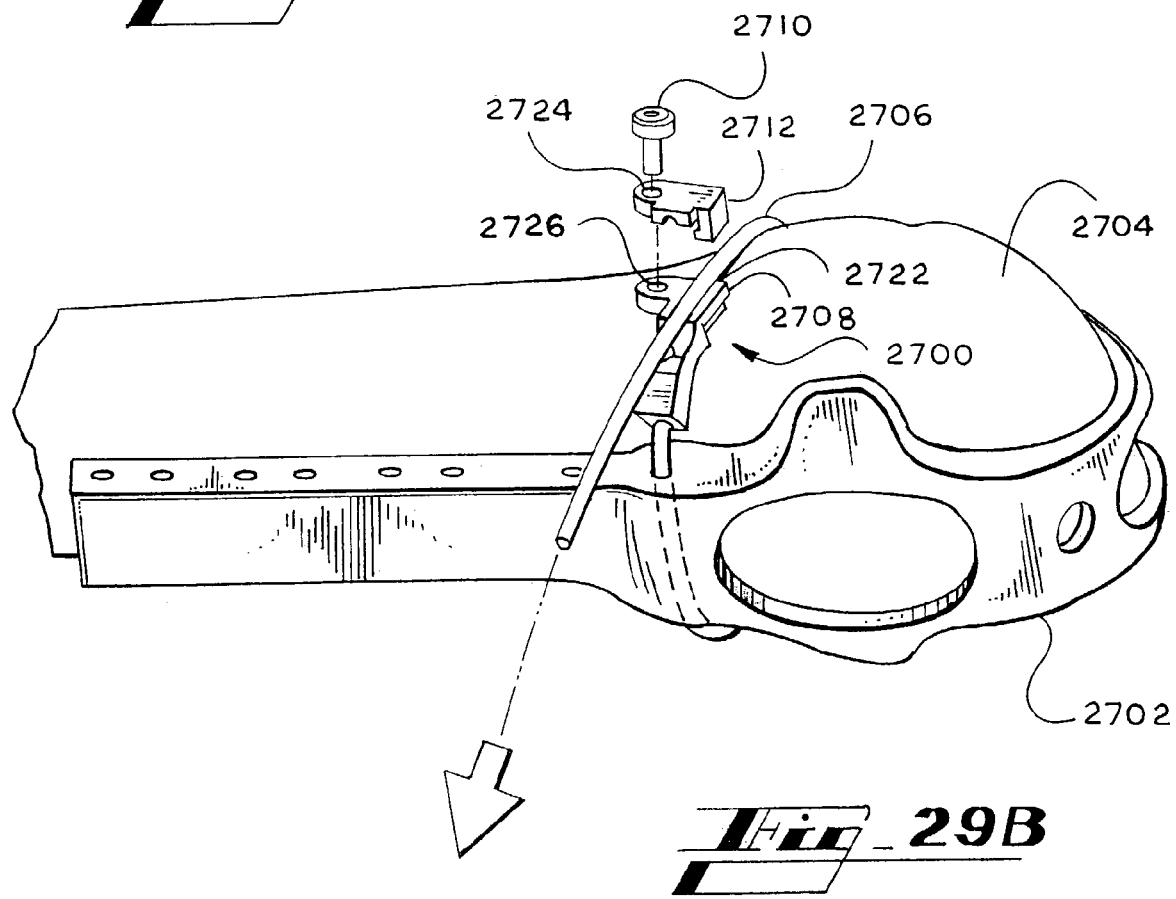
Fig_29B

SYSTEM, METHODS, AND APPARATUSES FOR CLAMPING AND RECLAMPING AN ORTHOPEDIC SURGICAL CABLE

RELATED APPLICATIONS

This is a continuation-in-part application of U.S. Ser. No. 10/230,040, entitled "Systems, Methods, and Apparatuses For Clamping and Reclamping an Orthopedic Surgical Cable," filed on Aug. 28, 2002, which is incorporated by reference.

FIELD OF THE INVENTION

The invention relates generally to systems, methods, and apparatuses related to orthopedic cable clamps, and more specifically to systems, methods, and apparatuses for clamping and reclamping an orthopedic surgical cable used in conjunction with an orthopedic implant device, a bone, and/or bone implant or structure.

BACKGROUND OF THE INVENTION

In an orthopedic surgical procedure, surgically implanted orthopedic cables are frequently used to secure bones together, or otherwise used to tie or fit other parts of the body together. An orthopedic cable is typically a thin length of cable that is manufactured from a biocompatible material such as cobalt chromium alloy, or stainless steel, or another similar type of material. Generally, an orthopedic cable is wrapped around an affected area of a patient's bone structure and then secured with a device such as a cable crimping device in order to stabilize the bone, secure fractures, stabilize trauma, install other devices to the bone, and for other purposes. Conventional orthopedic cable products utilize a device such as a cable crimping device to crimp the orthopedic cable in order to secure the cable with a specific tension around the affected area of a patient's body with a specific tension. However, crimping the cable typically causes damage to the cable and renders the cable unsuitable for re-use in an orthopedic procedure. It is not uncommon for an orthopedic cable to be replaced during the same surgical procedure when the tension on the orthopedic cable is insufficient and the cable must be retightened to obtain a sufficient tension. Since the orthopedic cable is damaged due to the crimping procedure, the orthopedic cable must be replaced. Replacing the orthopedic cable during a surgical procedure is time consuming for the surgeon and increases costs due to the wastage of the orthopedic cable.

In other instances, the conventional orthopedic cable product or portions of the product must also be replaced as well. In order to save time, manufacturers have designed single-use devices to secure the position of an orthopedic cable in a patient's body. These single-use devices cannot be reused and must be discarded if the orthopedic cable is initially tensioned and changes the tension or position of the surgical cable must be made later. Replacing the conventional orthopedic cable product or portions of the product during a surgical procedure is time consuming for the surgeon and increases costs due to the wastage of materials.

For example, one conventional orthopedic cable product utilizes a deformable sleeve or tube around the orthopedic cable. The metal sleeve or tube is then deformed by a screw that compresses the parts of the sleeve or tube around the cable. The metal sleeve or tube is deformed or crushed, and thus cannot be reused. Furthermore, the orthopedic cable may become deformed or crushed, and may not be suitable for re-use. In either event, once the surgical cable has been set to a desired position or tension, and for any reason becomes necessary to re-position or re-tension the surgical cable, then the metal sleeve or tube of the conventional orthopedic cable product must be replaced as well as the surgical cable.

In some instances, a conventional orthopedic cable product and an orthopedic cable are used in conjunction with an orthopedic device, a patient's bone, bone implant, or other structure. For example, an orthopedic device such as a trochanteric grip, can be secured to the exterior surface of a patient's femur using one or more orthopedic cables and corresponding conventional orthopedic cable products or devices. Each time an orthopedic cable is tensioned with respect to the patient's femur, the trochanteric grip becomes further secured to the exterior of the patient's femur. However, as each orthopedic cable is tensioned, other previously tensioned orthopedic cables may loosen, or the position of the orthopedic device may shift. In either instance, previously tensioned orthopedic cables may have to be re-tensioned or re-positioned with respect to the trochanteric grip and the patient's femur. Conventional orthopedic cable products or devices used to secure the position of the orthopedic cables may have to be replaced along with the orthopedic cables that have become damaged or crushed due to the installation of the orthopedic cable products or devices.

At least one conventional orthopedic cable product utilizes a releasable lever operated cable clamp to apply a clamping force to an orthopedic cable. The conventional orthopedic cable product tensions the cable to a desired tension, and a crimp is swaged onto the cable to hold the tension. Then the lever operated cable clamp releases the clamping force, and the cable clamp is removed from the cable. This type of conventional orthopedic cable product is not implantable within a patient's body. For example, the lever operated cable clamp is a separate component from the crimp, and is too large for implanting in a body. Such products utilizing a non-implantable clamp add to the complexity and time for performing relatively delicate surgical procedures.

In some circumstances, conventional orthopedic cable products or devices offset the positioning of an orthopedic cable, creating a nonalignment of the orthopedic cable with respect to the surgical cable clamp when securing the clamp and cable to a patient's bone or body. This can, among other things, eventually loosen the desired tension in the cable, or alter the desired positioning of the cable and/or surgical cable clamp, or cause the cable and/or surgical cable clamp to create an undesired stress or force on a specific portion of the patient's bone or body.

SUMMARY OF THE INVENTION

Systems, methods, and apparatuses according to various embodiments of the invention address some or all of the above issues and combinations thereof. They do so by providing a surgical cable clamp for clamping and reclamping an orthopedic surgical cable used in conjunction with an orthopedic implant device, a bone, and/or bone implant or structure. The surgical cable clamp does not damage the orthopedic surgical cable when then the surgical cable clamp is operated or clamped with respect to the surgical cable. While the surgical cable is operated or in use, a tension can be maintained on the orthopedic surgical cable. Furthermore, the surgical cable clamp can be reused along with the same surgical cable when the surgical cable clamp is unclamped and reclamped with respect to the surgical cable, while retensioning the surgical cable with respect to the orthopedic implant device, a bone, and/or bone implant or structure. Such systems, methods, and apparatuses are particularly useful for surgeons installing an orthopedic surgical cable within a patient's body, and attempting to tension and retension the orthopedic cable with respect to the installation of an orthopedic implant device, a bone, and/or bone implant or structure in the patient's body.

One aspect of systems, methods, and apparatuses according to various embodiments of the invention, focuses on apparatuses for clamping and reclamping an orthopedic cable for installation in a patient's body. For purposes of this document, such apparatuses are each known as a "surgical cable clamp." A surgical cable clamp permits a surgeon to save time and reduce wastage during a surgical procedure by providing the option to reuse both a surgical cable clamp and orthopedic surgical cable that have been initially installed and tensioned. The surgeon may find that later during the same surgical procedure, the surgical cable clamp and orthopedic surgical cable should be retensioned, and the surgical cable clamp permits the surgeon to reclamp the orthopedic cable with respect to the installation of an orthopedic implant device, a bone, and/or bone implant or structure in a patient's body.

Another aspect of systems, methods, and apparatuses according to various embodiments of the invention, focuses on systems for clamping and reclamping an orthopedic cable for installation of a device in a patient's body. A surgical cable clamp permits a surgeon to save time and reduce wastage during a surgical procedure by providing the option to reuse both a surgical cable clamp and orthopedic surgical cable that have been used to initially install a device within a patient's body. The surgeon may find that later during the same surgical procedure, the surgical cable clamp and orthopedic surgical cable should be retensioned, or the device must be repositioned with respect to the patient's body. The surgical cable clamp permits the surgeon to reclamp the orthopedic cable with respect to installation of the device in the patient's body.

According to another aspect of the invention, systems and apparatuses according to various embodiments of the invention include in a combination with an orthopedic cable, apparatus for clamping and reclamping an orthopedic cable for installation with respect to a patient's body. The apparatus includes a clamping body adapted to positioning with respect to a patient's body, and an orthopedic cable. The apparatus further includes a clamping mechanism adapted to secure the orthopedic cable to the clamping body, secure a first tension in the orthopedic cable, release the tension in the orthopedic cable; and re-secure the orthopedic cable relative to the clamping body to secure another tension in the orthopedic cable.

According to yet another aspect of the invention, systems and apparatuses according to various embodiments of the invention can include an orthopedic cable and a surgical cable clamp. The surgical cable clamp includes a clamping body and a clamping mechanism. The clamping body is adapted to receive a portion of the orthopedic cable. The clamping mechanism is adapted to contact a portion of the clamping body, create a compression force on the portion of the orthopedic cable to secure the orthopedic cable relative to the clamping body with a first tension, release the compression force on the portion of the orthopedic cable so that the orthopedic cable can be released relative to the clamping body, and create a second compression force on the portion of the orthopedic cable to re-secure the orthopedic cable relative to the clamping body with a second tension.

According to yet another aspect of the invention, systems and apparatuses according to various embodiments of the invention can include an orthopedic cable, a surgical cable clamp, and a device. The device includes a surgical cable clamp with a clamping body and clamping mechanism. The clamping body is adapted to receive a portion of the orthopedic cable. The clamping mechanism is adapted to contact a portion of the clamping body, create a compression force on the portion of the orthopedic cable to secure the orthopedic cable relative to the device with a first tension, release the compression force on the portion of the orthopedic cable so that the orthopedic cable can be released relative to the clamping body, and create a second compression force on the portion of the orthopedic cable to re-secure the orthopedic cable relative to the device with a second tension.

According to yet another aspect of the invention, systems and apparatuses according to various embodiments of the invention can include a combination of an orthopedic surgical cable and clamp. The combination includes an orthopedic surgical cable, a clamping body, a clamping mechanism, and a force application member. The clamping body is adapted to be installed relative to a bone in a patient, in order to apply a force to the bone. The clamping body is further adapted to restrain a first portion of the orthopedic surgical cable. The clamping mechanism is adapted to cooperate with the clamping body to capture a second portion of the orthopedic surgical cable between the clamping mechanism and the clamping body. It may be a separate piece or be part of the clamping body. The force application member connects to the clamping body and clamping mechanism. It is adapted to be manipulated such as by rotation in order to force the clamping body and clamping mechanism to grip the second portion of the orthopedic surgical cable in a manner whereby the force and consequent gripping are subject to gradual control by rotation or manipulation of the force application member and the gripping does not cause nonalignment of the clamp relative to the orthopedic surgical cable. The orthopedic surgical cable and clamp are adapted to allow the orthopedic surgical cable to be tensioned and secured by the clamp at a first tension, and to allow the orthopedic surgical cable to be subsequently tensioned and secured by the clamp at a second tension without loss of tension due to twisting or nonalignment of the clamp relative to the orthopedic surgical cable.

According to yet another aspect of the invention, systems and apparatuses according to various embodiments of the invention can include a combination of an orthopedic surgical cable and clamp. The combination includes an orthopedic surgical cable, a clamping body, a clamping mechanism, and a force application member. The orthopedic surgical cable is adapted to be installed relative to a bone in a patient, in order to apply a force to the bone. The clamping body is adapted to receive a first portion and a second portion of the orthopedic surgical cable. The clamping mechanism can be part of the clamping body or a separate piece. It is adapted to cooperate with the clamping body to capture the first portion and the second portion of the orthopedic surgical cable between the clamping mechanism and the clamping body. The force application member connects to the clamping body and clamping mechanism, and is adapted to be manipulated in order to force the clamping body and clamping mechanism to grip the first and second portions of the orthopedic surgical cable. It does this so that the force and consequent gripping are subject to gradual control by rotation or manipulation of the force application member. Furthermore, the gripping does not cause twisting or nonalignment of the clamp relative to the orthopedic surgical cable. Accordingly, the orthopedic surgical cable and clamp allow the orthopedic surgical cable to be tensioned and secured by the clamp at a first tension, and also to allow the orthopedic surgical cable to be subsequently tensioned and secured by the clamp at a second tension without loss of tension due to twisting or nonalignment of the clamp relative to the orthopedic surgical cable.

According to yet another aspect of the invention, systems and apparatuses according to various embodiments of the invention can include a combination of an orthopedic surgical cable and clamp. The combination includes an orthopedic surgical cable, a clamping body, a clamping mechanism, and a force application member. The orthopedic surgical cable is adapted to be installed relative to a bone in a patient, in order to apply a force to the bone. The clamping body is adapted to receive a first portion of the orthopedic surgical cable. The clamping mechanism, which can be part of the clamping body or a separate piece, is adapted to cooperate with the clamping body to capture a second portion of the orthopedic surgical cable between the clamping mechanism and the clamping body. The force application member connects to the clamping body and clamping mechanism, and is adapted to be activated in order to force the clamping body and clamping mechanism to grip the first and second portions of the orthopedic surgical cable so that the force and consequent gripping are subject to gradual control by the force application member and the gripping does not cause twisting or nonalignment of the clamp relative to the orthopedic surgical cable. Accordingly, the orthopedic surgical cable and clamp allow the orthopedic surgical cable to be tensioned and secured by the clamp at a first tension, and also to allow the orthopedic surgical cable to be subsequently tensioned and secured by the clamp at a second tension without loss of tension due to twisting or nonalignment of the clamp relative to the orthopedic surgical cable.

A particular method for clamping and reclamping a surgical cable according to one aspect of systems and apparatuses of various embodiments of the invention includes mounting a portion of a surgical cable to the surgical cable clamp; applying a force to the portion of the surgical cable so that the surgical cable is secured relative to the surgical cable clamp with a first tension in the surgical cable; releasing the force on the portion of the surgical cable so that the surgical cable can be repositioned relative to the surgical cable clamp; and applying a second force to the surgical cable so that the surgical cable is again secured relative to the surgical cable clamp.

Another particular method for clamping and reclamping a surgical cable according to one aspect of systems and apparatuses of various embodiments of the invention includes securing a first portion of a surgical cable with a surgical cable clamp so that the first portion of the surgical cable is restrained relative to the surgical cable clamp; wrapping a remaining portion of the surgical cable around a part of a patient's body; connecting an extended portion of the surgical cable to the surgical cable clamp; applying a force to the extended portion of the surgical cable so that the surgical cable is secured relative to the surgical cable clamp with a first tension in the surgical cable; releasing the force on the extended portion of the surgical cable so that the surgical cable can be repositioned relative to the surgical cable clamp; and applying another force to the surgical cable so that the surgical cable is again secured relative to the surgical cable clamp.

Another particular method for using a surgical cable clamp with an orthopedic surgical cable for installation of a device with respect to a patient's body according to one aspect of systems and apparatuses of various embodiments of the invention includes restraining a first portion of a surgical cable with a surgical cable clamp so that the first portion of the surgical cable is restrained relative to the surgical cable clamp; connecting the surgical cable to a device; wrapping a remaining portion of the surgical cable around a part of a patient's body; connecting an extended portion of the surgical cable to the surgical cable clamp; applying a force to the extended portion of the surgical cable so that the surgical cable and the device are secured relative to the surgical cable clamp with a first tension in the surgical cable; releasing the force on the extended portion of the surgical cable so that the surgical cable or device can be repositioned relative to the surgical cable clamp; and applying another force to the surgical cable so that the surgical cable and device are again secured relative to the surgical cable clamp.

Another particular method for using a surgical cable clamp with an orthopedic surgical cable for installation with respect to a patient's body according to one aspect of systems and apparatuses of various embodiments of the invention includes using a surgical cable clamp in combination with an orthopedic surgical cable to mount a portion of the orthopedic surgical cable to the surgical cable clamp; and to apply a force to the portion of the orthopedic surgical cable so that the orthopedic surgical cable is secured relative to the surgical cable clamp with a first tension in the orthopedic surgical cable. The method includes reusing the surgical cable clamp in combination with the orthopedic surgical cable to release the force on the portion of the orthopedic surgical cable so that the surgical cable can be repositioned relative to the surgical cable clamp; and to apply a second force to the orthopedic surgical cable so that the orthopedic surgical cable is again secured relative to the surgical cable clamp.

Another particular method for using a surgical cable clamp with an orthopedic surgical cable for installation with respect to a patient's body according to one aspect of systems and apparatuses of various embodiments of the invention includes installing an orthopedic surgical cable in a patient's body using a clamp that allows the tension in the cable to be adjusted and gradually tensioned. The method includes providing an orthopedic surgical cable and a surgical cable clamp. The surgical cable clamp includes a clamping body, a clamping mechanism, and a force application member. The method also includes mounting the surgical cable clamp relative to a bone in a patient's body, and restraining a first portion of the orthopedic surgical cable relative to the clamping body. A second portion of the orthopedic surgical cable is captured between the clamping mechanism and the clamping body. Next, the force application member connects to the clamping body and the clamping mechanism. The method includes gripping the second portion of the orthopedic surgical cable between the clamping body and clamping mechanism by rotating or manipulating the force application member in a first direction so that the gripping is subject to gradual control by rotation or manipulation of the force application member and the gripping does not cause twisting or nonalignment of the clamp relative to the orthopedic surgical cable, thus maintaining a first tension in the orthopedic surgical cable.

The method also includes releasing the first tension in the orthopedic surgical cable by rotating or manipulating the force application member in an opposing direction to the first direction so that the orthopedic surgical cable can be repositioned between the clamping mechanism and the clamping body; and gripping the second portion of the orthopedic surgical cable between the clamping body and clamping mechanism by rotating or manipulating the force application member in the first direction so that consequent gripping is subject to gradual control by rotation or manipulation of the force application member and the gripping does not cause twisting or nonalignment of the clamp relative to the orthopedic surgical cable, thus maintaining a second tension in the orthopedic surgical cable.

Another particular method for using a surgical cable clamp with an orthopedic surgical cable for installation with respect to a patient's body according to one aspect of systems and apparatuses of various embodiments of the invention includes providing an orthopedic surgical cable and a surgical cable clamp. The surgical cable clamp includes a clamping body, a clamping mechanism, and a force application member. The method also includes mounting the clamping body to a bone in a patient's body; connecting a first portion of the orthopedic surgical cable to the clamping body; wrapping a remaining portion of the orthopedic surgical cable around a part of a patient's bone; connecting a second portion of the orthopedic surgical cable to the clamping body; and capturing the first portion and second portion of the orthopedic surgical cable between the clamping body and clamping mechanism. Next, the force application member connects to the clamping body and clamping mechanism. The method also includes gripping the first and second portions of the orthopedic surgical cable between the clamping body and the clamping mechanism by rotating or manipulating the force application member in a first direction so that the consequent gripping is subject to gradual control by the threaded force application member and the gripping does not cause twisting or nonalignment of the clamp relative to the orthopedic surgical cable, thus maintaining a first tension in the orthopedic surgical cable; releasing the first tension in the orthopedic surgical cable by rotating or manipulating the threaded force application member in a second direction so that the orthopedic surgical cable can be repositioned between the clamping mechanism and the clamping body; and gripping the first and second portions of the orthopedic surgical cable between the clamping body and the clamping mechanism by rotating or manipulating the force application member in the first direction so that the consequent gripping is subject to gradual control by the force application member and the gripping does not cause twisting or nonalignment of the clamp relative to the orthopedic surgical cable, thus maintaining a second tension in the orthopedic surgical cable.

Yet another particular method for using a surgical cable clamp with an orthopedic surgical cable for installation with respect to a patient's body according to one aspect of systems and apparatuses of various embodiments of the invention includes providing an orthopedic surgical cable and a surgical cable clamp. The surgical cable clamp includes a clamping body, a clamping mechanism, and a force application member. The method includes mounting the surgical cable clamp to a bone in the patient's body; restraining a first portion of the orthopedic surgical cable with the surgical cable clamp; wrapping a remaining portion of the orthopedic surgical cable around a part of the patient's bone; capturing an extended portion of the orthopedic surgical cable between the clamping body and the clamping mechanism; and gripping the extended portion of the orthopedic surgical cable between the clamping body and the clamping mechanism by activating the force application member so that the consequent gripping is subject to gradual control by the force application member and the gripping does not cause twisting or nonalignment of the clamp relative to the orthopedic surgical cable, thus maintaining a first tension in the orthopedic surgical cable. The method further includes deactivating the force application member so that the first tension can be released and the orthopedic surgical cable can be repositioned between the clamping mechanism and the clamping body; and gripping the extended portion of the orthopedic surgical cable between the clamping body and the clamping mechanism together by activating the force application member so that the clamping body and clamping mechanism grip the extended portion of the orthopedic surgical cable in a manner whereby the force and consequent gripping are subject to gradual control by the force application member and the gripping does not cause twisting or nonalignment of the clamp relative to the orthopedic surgical cable, thus maintaining a second tension in the orthopedic surgical cable.

Objects, features and advantages of various systems, methods, and apparatuses according to various embodiments of the invention include:

(1) providing the ability to clamp and reclamp an orthopedic surgical cable without damaging the cable and creating the need to replace the cable;

(2) providing the ability to reuse a surgical cable clamp during the same surgical procedure;

(3) providing the ability to reuse the orthopedic surgical cable when the surgical cable clamp initially clamps the cable, and the cable needs to be retensioned or repositioned;

(4) providing the ability to reposition a device in a patient's body by reusing a surgical cable clamp and orthopedic surgical cable that have been initially used and tensioned, by retensioning the surgical cable by reclamping the cable with the surgical cable clamp;

(5) providing the ability to implant a device in a patient's body for clamping and reclamping a surgical cable; and (6) providing the ability to tension and retension an orthopedic surgical cable without twisting or nonalignment of the surgical cable clamp relative to the orthopedic surgical cable.

Other objects, features and advantages of various aspects and embodiments of systems, methods, and apparatuses according to the invention are apparent from the other parts of this document.

BRIEF DESCRIPTION OF THE DRAWINGS

FIG. 1a is a perspective view of a structure that includes a surgical cable clamp in accordance with various embodiments of the invention.

FIG. 1b is another perspective view of a structure that includes a surgical cable clamp in accordance with various embodiments of the invention.

FIG. 1c is another perspective view of a structure that includes a surgical cable clamp in accordance with various embodiments of the invention.

FIG. 2 is an exploded perspective view of another structure for a surgical cable clamp in accordance with various embodiments of the invention.

FIGS. 3a-c illustrate a sequence for a method for using the surgical cable clamp shown in FIG. 2.

FIG. 4a illustrates an exploded perspective view of another structure for a surgical cable clamp in accordance with various embodiments of the invention.

FIG. 4b illustrates a cross-sectional view of the surgical cable clamp shown in FIG. 4a.

FIGS. 5a-d illustrate a sequence of another method for using a surgical cable clamp in accordance with various embodiments of the invention.

FIG. 6 is an exploded perspective view of another structure for a surgical cable clamp in accordance with various embodiments of the invention.

FIG. 7 is an exploded perspective view of another structure for a surgical cable clamp in accordance with various embodiments of the invention.

FIG. 8a is another view of a structure for a surgical cable clamp in accordance with various embodiments of the invention.

FIG. 8b is a cross-sectional view of the surgical clamp shown in FIG. 8a in a clamped position.

FIG. 9a is another view of a structure for a surgical cable clamp in accordance with various embodiments of the invention.

FIG. 9b is a cross-sectional view of the surgical cable clamp shown in FIG. 9a.

FIG. 10a is another view of a structure for a surgical cable clamp in accordance with various embodiments of the invention.

FIG. 10b is a cross-sectional view of the surgical cable clamp shown in FIG. 10a.

FIG. 11a is another view of a structure for a surgical cable clamp in accordance with various embodiments of the invention.

FIG. 11b is a cross-sectional view of the surgical cable clamp shown in FIG. 11a.

FIG. 12a is another view of a structure for a surgical cable clamp in accordance with various embodiments of the invention.

FIG. 12b is the surgical cable clamp shown in FIG. 12a in a clamped position.

FIG. 13a is another view of a structure for a surgical cable clamp in accordance with various embodiments of the invention.

FIG. 13b is a side exploded view of the surgical cable clamp shown in FIG. 13a.

FIG. 14a is another view of a structure for a surgical cable clamp in accordance with various embodiments of the invention.

FIG. 14b is a side exploded view of the surgical cable clamp shown in FIG. 14a.

FIG. 15a is another view of a structure for a surgical cable clamp in accordance with various embodiments of the invention.

FIG. 15b is an isometric view of the surgical cable clamp shown in FIG. 15a in an unclamped position cross section view.

FIG. 16a is another view of a structure for a surgical cable clamp in accordance with various embodiments of the invention.

FIG. 16b is an exploded perspective view of the surgical cable clamp shown in FIG. 16a.

FIG. 17a is another view of a structure for a surgical cable clamp in accordance with various embodiments of the invention.

FIG. 17b is an exploded perspective view of the surgical cable clamp shown in FIG. 17a.

FIG. 18a is another view of a structure for a surgical cable clamp in accordance with various embodiments of the invention.

FIG. 18b is a cross-sectional view of the surgical cable clamp shown in FIG. 18a.

FIG. 19a is another view of a structure for a surgical cable clamp in accordance with various embodiments of the invention.

FIG. 19b is a cross-sectional view of the surgical cable clamp shown in FIG. 19a.

FIG. 20a is another view of a structure for a surgical cable clamp in accordance with various embodiments of the invention.

FIG. 20b is a cross-sectional view showing the clamp position of the surgical cable clamp shown in FIG. 20a.

FIG. 21a is another view of a structure for a surgical cable clamp in accordance with various embodiments of the invention.

FIG. 21b is a cross-sectional view showing the clamp position of the surgical cable clamp shown in FIG. 21a FIG. 22a is another view of a structure for a surgical cable clamp in accordance with various embodiments of the invention.

FIG. 22b is a cross-sectional view showing clamp position of the surgical cable clamp shown in FIG. 22a.

FIG. 23a is another view of a structure for a surgical cable clamp in accordance with various embodiments of the invention.

FIG. 23b is cross-sectional view of the surgical cable clamp shown in FIG. 23a.

FIG. 24a is another view of a structure for a surgical cable clamp in accordance with various embodiments of the invention.

FIG. 24b is a cross-sectional view showing clamp position of the surgical cable clamp shown in FIG. 24a FIG. 25a is another view of a structure for a surgical cable clamp in accordance with various embodiments of the invention.

FIG. 25b is an exploded perspective view of the surgical cable clamp shown in FIG. 25a.

FIGS. 29a-c illustrate a sequence for a method for using the surgical cable clamp shown in FIGS. 26-28.

DETAILED DESCRIPTION OF SPECIFIC EMBODIMENTS

Figure 26:
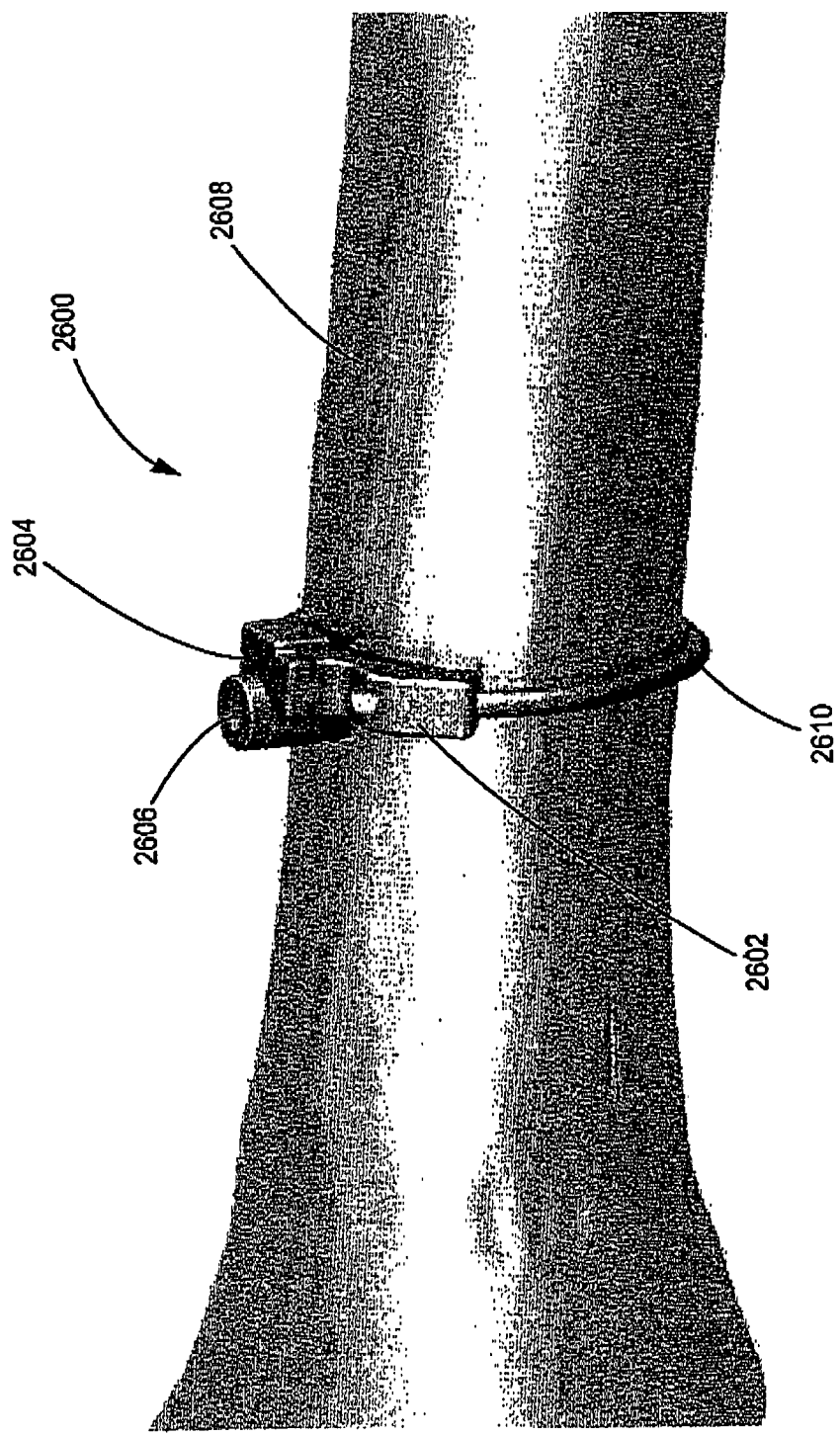
FIG. 26 is a perspective view of a structure of a surgical cable clamp in accordance with various embodiments of the invention.

Systems, methods, and apparatuses according to various embodiments of the invention address some or all of the above issues and combinations thereof. They do so by providing a surgical cable clamp for clamping and reclamping an orthopedic surgical cable used in conjunction with an orthopedic implant device, a bone, and/or bone implant or structure. The surgical cable clamp does not damage the orthopedic surgical cable when then the surgical cable clamp is operated or clamped with respect to the surgical cable. While the surgical cable is operated or in use, a tension can be maintained on the orthopedic surgical cable. Furthermore, the surgical cable clamp can be reused along with the same surgical cable when the surgical cable clamp is unclamped and reclamped with respect to the surgical cable, while retensioning the surgical cable with respect to the orthopedic implant device, a bone, and/or bone implant or structure. Such systems, methods, and apparatuses are particularly useful for surgeons installing an orthopedic surgical cable within a patient's body, and attempting to tension and retension the orthopedic cable with respect to the installation of an orthopedic implant device, a bone, and/or bone implant or structure in the patient's body.

FIG. 1a is a perspective view of a preferred environment for a surgical cable clamp in accordance with various embodiments of the invention. A preferred environment 100 shown in FIG. 1a is the proximal end of a human femur bone 102 in conjunction with a trochanteric grip 104 for use in a total hip replacement surgical procedure. In a first embodiment of the invention, a surgical cable clamp is a stand alone-type clamp 106 for securing the position of an orthopedic surgical cable 108 relative to a portion of the trochanteric grip 104 and a patient's femur bone 102. In a second embodiment of the invention, a surgical cable clamp is a device-incorporated clamp 110 for securing the position of an orthopedic surgical cable 108 relative to a portion of the trochanteric grip 104 and a patient's femur bone 102. The device-incorporated clamp 110 utilizes a portion of the trochanteric grip 104 or other prefabricated orthopedic device for clamping the orthopedic surgical cable 108.

Typically, a trochanteric grip 104 is secured at the proximal end of a patient's femur bone 102 during a total hip replacement procedure. One or more orthopedic surgical cables 108 can be utilized to secure the trochanteric grip 104 into a position relative to the proximal end of a patient's femur bone 102. When a force is applied to a surgical cable clamp 106, 110, the surgical cable clamp 106, 110 compresses the orthopedic surgical cable 108, thus securing the orthopedic surgical cable 108 into a position relative to the trochanteric grip 104 and patient's femur 102.

If necessary, the orthopedic surgical cable 108 can be loosened or otherwise retensioned by applying another force to the surgical cable clamp 106, 110 to relieve the compression force on the orthopedic surgical cable 108 applied by the surgical cable clamp 106, 110. The orthopedic surgical cable 108 can then be retensioned by hand or by way of a tensioning device (not shown) so that the orthopedic surgical cable 108 is at a desired tension or position. Yet another force can then be applied to the surgical cable clamp 106, 110 to create another compression force on the orthopedic surgical cable 108 which can then maintain the desired tension or position of the orthopedic surgical cable 108. Depending upon the location of the orthopedic surgical cable 108 relative to the trochanteric grip 104 and the patient's femur bone 102 or other bone, either and/or both the stand alone-type clamp 106 or the device-incorporated clamp 110 may be used to secure the position and tension of the orthopedic surgical cable 108 as shown.

A surgical cable clamp in accordance with the invention can have other configurations as shown and described in FIGS. 1b, 1c, 4, and 6-28. A surgical cable clamp can be either a stand alone-type clamp device or a device incorporated-type clamp device. Furthermore, as one skilled in the art will recognize, a surgical cable clamp can be fashioned as a single or multiple component-type clamp. In any configuration, a surgical cable clamp is used to secure a tension and, if necessary, secure another tension in an orthopedic surgical cable without need for replacing the original surgical cable. A surgical cable clamp in accordance with the invention can be used with other prefabricated orthopedic devices, such as a bone plate, that utilize orthopedic surgical cables for securing the device to a bone or another part of a patient's body. Finally, even though a surgical cable clamp in accordance with the invention is shown in FIG. 1a used in conjunction with an orthopedic surgical cable and a trochanteric grip, a surgical cable clamp can be utilized with one or more surgical cables, or incorporated into another type of orthopedic device to be secured to a portion of a patient's body such as a bone or another body structure.

FIG. 1b is a perspective view of a structure including a surgical cable clamp in accordance with the invention. The structure shown in FIG. 1b is a trochanteric grip 112 that can be installed adjacent to the proximal end of a human femur bone (similar to that shown in FIG. 1a as 102) for use in a total hip replacement surgical procedure. In another embodiment of the invention, a surgical cable clamp is a device-incorporated clamp 114 for securing the position of an orthopedic surgical cable (not shown) relative to a portion of the trochanteric grip 112 and a patient's femur bone. The device-incorporated clamp 114 utilizes a portion of the trochanteric grip 112 or other prefabricated orthopedic device for clamping the orthopedic surgical cable.

Similar to 104 in FIG. 1a, the trochanteric grip 112 is secured at the proximal end of a patient's femur bone during a total hip replacement procedure. One or more orthopedic surgical cables can be utilized to secure the trochanteric grip 112 into a position relative to the proximal end of a patient's femur bone. When a force is applied to a device-incorporated clamp 114, the device-incorporated clamp 114 compresses the orthopedic surgical cable, thus securing the orthopedic surgical cable into a position relative to the trochanteric grip 112 and patient's femur.

If necessary, the orthopedic surgical cable can be loosened by applying another force to the device-incorporated clamp 114 to relieve the compression force on the orthopedic surgical cable applied by the device-incorporated clamp 114. The orthopedic surgical cable can then be retensioned by hand or by way of a tensioning device (not shown) so that the orthopedic surgical cable is at a desired tension or position. Yet another force can then be applied to the device-incorporated clamp 114 to create another compression force on the orthopedic surgical cable which can then maintain the desired tension or position of the orthopedic surgical cable. Depending upon the location of the orthopedic surgical cable relative to the trochanteric grip 112 and the patient's femur bone or other bone, the device-incorporated clamp 114 may be used to secure the position and secure the tension of the orthopedic surgical cable.

FIG. 1c is a perspective view of another structure including a surgical cable clamp in accordance with the invention. The structure shown in FIG. 1c is a bone plate 116 that can be installed adjacent to a human bone for use in an orthopedic surgical procedure. In another embodiment of the invention, a surgical cable clamp is a device-incorporated clamp 118 for securing the position of an orthopedic surgical cable (not shown) relative to a portion of the bone plate 116 and a patient's bone. The device-incorporated clamp 118 utilizes a portion of the bone plate 116 or other prefabricated orthopedic device for clamping the orthopedic surgical cable.

The bone plate 116 is adjacent to a patient's bone during an orthopedic surgical procedure. One or more orthopedic surgical cables can be utilized to secure the bone plate 116 into a position relative to the patient's bone. When a force is applied to a device-incorporated clamp 118, the device-incorporated clamp 118 compresses the orthopedic surgical cable, thus securing the orthopedic surgical cable into a position relative to the bone plate 116 and patient's bone.

If necessary, the orthopedic surgical cable can be loosened by applying another force to the device-incorporated clamp 118 to relieve the compression force on the orthopedic surgical cable applied by the device-incorporated clamp 118. The orthopedic surgical cable can then be retensioned by hand or by way of a tensioning device (not shown) so that the orthopedic surgical cable is at a desired tension or position. Yet another force can then be applied to the device-incorporated clamp 118 to create another compression force on the orthopedic surgical cable which can then maintain the desired tension or position of the orthopedic surgical cable. Depending upon the location of the orthopedic surgical cable relative to the bone plate 116 and the patient's bone or other bone, the device-incorporated clamp 118 may be used to secure the position and secure the tension of the orthopedic surgical cable.

The device-incorporated clamps 114, 118 of FIGS. 1b and 1c are preferred embodiments of the invention. Other embodiments of the invention can also be used in the structure shown in FIGS. 1b and 1c to accomplish similar functions in accordance with the invention.

FIG. 2 is a perspective view of an embodiment of a stand alone-type clamp 200 similar to that shown as 106 in FIG. 1a. The embodiment of the stand alone-type clamp 200 shown here includes an upper clamping body 202, a clamping bolt 204, and a lower clamping body 206.

The upper clamping body 202 in this embodiment is rectangularly-shaped and has a relatively flat profile with a generally rounded upper surface 208 and a generally flat lower surface 210. On a lateral side 212 between the upper surface 208 and lower surface 210, a pair of semi-circular cable channels 214 are machined in the lower surface 210. The cable channels 214 are sized to receive the width of an orthopedic surgical cable (not shown) and are machined through the width of the upper clamping body 202 along the lower surface 210 to the opposing lateral side. Through the upper surface 208, a bolt hole 216 for receiving the clamping bolt 204 is machined through the thickness of the clamping body 202 to the lower surface 210. Note that the upper clamping body 202 can have numerous other shapes and configurations in accordance with the invention.

The clamping bolt 204 in this embodiment is shaped similar to a conventional machine screw with a socket head 218, a threaded body 220, and blunt point 222. The socket head 218 includes a recess 224 sized to receive a hexagonal-shaped tightening instrument (not shown) for tightening and untightening the clamping bolt 204 to a desired tension. Alternatively, the external shape of the socket head 218 can be shaped for tightening with a wrench-type instrument (not shown) for tightening and untightening a corresponding geometrically-shaped socket head. The threaded body 220 is sized to diametrically fit within the bolt hole 216 of the upper clamping body, and includes one or more threads 226 sized to receive corresponding threads of the lower clamping body 206. Note that the clamping bolt 204 may have numerous other shapes and configurations in accordance with the invention.

The lower clamping body 206 is rectangularly-shaped and has a C-shaped profile with a generally rounded lower surface 228 and a generally flat upper surface 230 sized to receive the lower surface 210 of the upper clamping body 202. On a lateral side 232 between the lower surface 228 and upper surface 230, a pair of semi-circular cable channels 234 are machined in the upper surface 230. The cable channels 234 are sized to receive the width of an orthopedic surgical cable (not shown) and are machined through the width of the lower clamping body 206 along the upper surface 230 to the opposing lateral side. Each cable channel 234 includes a series of grooves 236 or ridges machined in the length of the cable channel 234 of the lower clamping body 206. A series of corresponding grooves (not shown) or ridges is also machined in the length of the cable channel 214 of the upper clamping body 202.

Through the upper surface 230, a threaded bolt hole 238 for receiving the clamping bolt 204 is machined through the thickness of the lower clamping body 206 to the lower surface 228. Note that the lower clamping body 206 can have numerous other shapes and configurations in accordance with the invention.

When the threaded bolt hole 236 is concentrically aligned with the bolt hole 216 of the upper clamping body 202, ends 240 of the upper clamping body 202 fit within recesses 242 of the lower clamping body, thus assisting alignment of the semi-circular-shaped cable channels 214 of the upper clamping body 202 with the semi-circular-shaped cable channels 234 of the lower clamping body 206 to form a pair of circular-shaped cable holes for the stand alone-type clamp 200. In this configuration, the series of grooves 236 of the lower clamping body 206 and corresponding grooves (not shown) of the upper clamping body 202 align with each other to decrease the width of the circular hole formed by the alignment of the cable channels 214, 234. Furthermore, when the upper clamping body is aligned with the lower clamping body clamping bolt 204, the clamping bolt 204 can be inserted through the bolt hole 216 and then torqued to engage the threads of the threaded bolt hole 238 of the lower clamping body 206.

A surgical cable clamp such as a stand alone-type clamp 200 can be manufactured from titanium, stainless steel, cobalt chromium alloy, or another similar type of material. An example of a stand alone-type clamp 200 measures approximately 0.3 inches (7.6 mm) in width perpendicular to the orientation of the surgical cable, approximately 0.2 inches (5.1 mm) in height, and approximately 0.5 inches in length (12.7 mm) parallel with the orientation of the surgical cable when the upper clamping body and lower clamping body are aligned together. An example of a clamping bolt is a conventional #8 machine screw made from titanium, stainless steel, cobalt chromium alloy, or a similar type of material that is compatible with material of the upper and lower clamping body. In some instances, the clamping bolt may be coated with an implantable coating designed to reduce frictional contact with other components of the clamp. Furthermore, an example of a surgical cable that can be used with the stand alone-type clamp 200 is typically a cobalt chromium or stainless steel cable measuring approximately 0.04 to 0.08 inches (1.0 to 2.0 mm) in diameter.

The stand alone-type clamp 200 is a preferred embodiment of a surgical cable clamp. The embodiments shown in FIGS. 1b, 1c, 4, and 6-28 are other embodiments of the invention that can also be used in the preferred environment shown in FIG. 1a. Other embodiments of a surgical cable clamp can be used in the preferred environment and other similar type environments to accomplish similar functions in accordance with the invention.

FIGS. 3a-c illustrate a sequence for a method for using the surgical cable clamp shown in FIGS. 1a and 2. The particular embodiment shown in this sequence utilizes a stand alone-type surgical cable clamp, shown in FIG. 2 as 200. Other embodiments of a surgical cable clamp can be utilized with the method illustrated in FIGS. 3a-c.

In FIG. 3a, a surgical cable clamp 300 in accordance with the invention is shown adjacent to an orthopedic device such as a trochanteric grip 302. The trochanteric grip 302 is aligned with a proximal end of a patient's femur bone 304 in accordance with a hip replacement procedure. When the trochanteric grip 302 is to be secured to the patient's femur 304, the surgical cable clamp 300 is positioned in a desired position adjacent to the trochanteric grip 302 to receive an orthopedic surgical cable 306. Typically, the surgical cable clamp 300 is preassembled prior to the sequence. Similar to the cable clamp in FIG. 2, the surgical cable clamp 300 includes an upper clamping body 308, a clamping bolt 310, and a lower clamping body 312, and can be preassembled as described in FIG. 2. A relatively smaller diameter end 314 of a predetermined length of surgical cable 306 is inserted into and pulled through a first cable channel 316 or hole of the surgical cable clamp 300 formed by the assembly and alignment of the upper clamping body 308 with the lower clamping body 312. A bead 318 on a relatively larger diameter end of the surgical cable 306 secures the relatively larger diameter end of surgical cable 306 adjacent to the surgical cable clamp 300 when the length of the surgical cable 306 is pulled through the first cable channel 316 or hole.

As shown in FIG. 3b, the relatively smaller diameter end 314 of the surgical cable 306 is inserted through a corresponding cable channel 320 or hole in the trochanteric grip 302 and wrapped around the thickness of the patient's femur 304. When the relatively smaller diameter end 314 of the surgical cable 306 is nearly around the patient's femur 304, the relatively smaller diameter end 314 is inserted through a second cable channel 322 or hole of the surgical cable clamp 300.

As shown in FIG. 3c, the relatively smaller diameter end 314 of the surgical cable 306 is manually pulled through the second cable channel 322 or hole or with a cable tensioning device (not shown) until a desired tension in the surgical cable 306 is attained. When the surgical cable 306 is pulled to a desired tension, the clamping bolt 310 is tightened with a hexagonal-shaped tightening instrument (not shown) until a compression force between the upper clamping body 308 and lower clamping body 312 maintains the desired tension on the surgical cable 306. Any excess length of surgical cable can be trimmed with a cutting instrument (not shown).

In some instances, a cable tensioning device (not shown) can be used to tighten the surgical cable 306 to a predetermined tension. A tightening instrument with a corresponding hexagonal-shaped head or driver such as a "T-handled driver" with a hex head to match the shape of the clamping bolt can then be used to tighten the clamping bolt 310 to a preset torque while measuring the tension on the surgical cable with the cable tensioning device as the clamping bolt 310 is tightened. A suitable cable tensioning device can be a device or system that applies a tension to a surgical cable, maintains the tension on the surgical cable until the tightening instrument can be used to tighten the clamping bolt of the surgical cable clamp, measures the tension in the surgical cable, and releases the surgical cable when the clamping bolt has secured the surgical cable.

More than one surgical cable 306 may be needed to secure an orthopedic device such as a trochanteric grip 302 or bone plate to a patient's femur 304. The above sequence can repeat as needed until the trochanteric grip or other orthopedic device is secured to the patient's femur or bone. After tensioning one or more surgical cables 306 to the patient's femur with one or more corresponding surgical cable clamps 300, previously tensioned surgical cables may tend to loosen or otherwise require additional tension to sufficiently secure the orthopedic device such as a trochanteric grip 302 to the patient's femur 304. If necessary, the tension on a previously tensioned surgical cable can be released by applying an untightening force to the clamping bolt 310 with the hexagonal-shaped tightening instrument, releasing the compression force between the upper clamping body 308 and lower clamping body 312, thus releasing the compression and tension on the surgical cable 306. The surgical cable 306 is then retensioned manually or by use of the cable tensioning device. When the desired tension is reached, a tightening force is applied to the clamping bolt 310 in order to create a sufficient compression force between the upper clamping body 308 and the lower clamping body 312 to maintain the desired tension in the surgical cable 306, and secure the position of the surgical cable 306 relative to the surgical cable clamp 300.

Tensioning and retensioning of one or more surgical cables 306 may occur more than once during a surgical procedure until all of the surgical cables 306 are sufficiently tensioned to maintain the position of the surgical cables 306, bone plate and or trochanteric grip 302 relative to the patient's femur 304. The sequence described above with respect to FIGS. 3a-c can be repeated as necessary to accomplish this.

Preferably, the surgical cable clamp illustrated in FIGS. 3a-c and in other figures can be preassembled prior to installation or use. Preassembly of a surgical cable clamp can include assembling component parts of the surgical cable clamp together with, or without, an orthopedic surgical cable so that a user such as a surgeon can rapidly install or use the surgical cable clamp. In many cases, preassembly of the surgical cable clamp with an orthopedic surgical cable saves time during a surgical procedure when installing or using the surgical cable clamp.

FIGS. 4a-b illustrate another embodiment of a surgical cable clamp in accordance with the invention. FIG. 4a is a perspective view of an embodiment of a device-incorporated clamp 400 similar to that shown as 110 in FIG. 1a; and FIG. 4b illustrates a cross-sectional view of the embodiment shown in FIG. 4a. The embodiment of the device-incorporated clamp 400 shown here includes a device body 402, a clamping bolt 404, and a clamping body 406.

The device body 402 in this embodiment is a bone plate such as a portion of a trochanteric grip with a relatively flat lower surface 408 and a relatively flat upper surface 410. Typically, the lower surface 408 is adjacent to a patient's bone or other structure, while the upper surface 410 remains exposed. On a lateral side 412 of the device body 402, a pair of cable holes 414 sized to receive the ends of an orthopedic surgical cable (not shown) are machined through the width of the device body 402 to the opposing lateral side. Between the lower surface 408 and upper surface 410, a bolt hole 416 for receiving the clamping bolt 404 is machined through the thickness of the device body 402. In the lower surface 408, a recess 418 for receiving a portion of the clamping body 406 is concentrically positioned with the bolt hole 416. Note that the device body 402 can have numerous other shapes and configurations for receiving the clamping body 406 and clamping bolt 404 in accordance with the invention.

The clamping bolt 404 in this embodiment is shaped similar to a conventional machine screw with a socket head 420, a threaded body 422, and blunt point 424. The socket head 420 is sized to receive a hexagonal-shaped tightening instrument (not shown) for tightening and untightening a corresponding socket-shaped head. Alternatively, the external shape of the socket head 420 can be shaped for tightening with a wrench-type instrument (not shown) for tightening and untightening a corresponding geometrically-shaped socket head 420. The threaded body 422 includes one or more threads 426 sized to engage corresponding threads machined in the clamping body 406. The blunt point 424 of the clamping bolt 404 is sized to fit within the bolt hole 416 in the upper surface 410 of the device body 402. Note that the clamping bolt 404 may have numerous other shapes and configurations in accordance with the invention.

The clamping body 406 is shaped like a wingnut, but can also be shaped similar to the upper clamping body shown in FIG. 2. Typically, the clamping body 406 includes a rounded upper surface 428, a generally flat lower surface 430, a pair of semi-circular channels 432 in the lower surface 430, and a bolt hole 434 through the thickness of the clamping body 406 between the upper surface 428 and the lower surface 430. Each channel 432 can include a series of grooves (not shown) or ridges machined in the length of the channel 432 of the clamping body 406. A series of corresponding grooves (not shown) or ridges can also be machined in the length of a corresponding channel (not shown) of the device body 402. The clamping body 406 is sized to fit within the recess 418 in the lower surface 408 of the device body 402. When the clamping body 406 is positioned within the recess 418, the bolt hole 434 of the clamping body 406 is concentric with the threaded bolt hole 416 of the device body 402, thus providing a receiving hole for the clamping bolt 404. Note that the clamping body 406 and corresponding recess 418 can have numerous other shapes and configurations in accordance with the scope of the invention.

A surgical cable clamp such as a device-incorporated clamp 400 can be manufactured from titanium, stainless steel, cobalt chromium alloy, or another similar type of material. An example of a device-incorporated clamp 400 measures approximately 0.3 inches (7.6 mm) across the width of the clamping body perpendicular to the orientation of the surgical cable, and approximately 0.25 inches (6.4 mm) across the diameter of the clamping body perpendicular to the orientation of the surgical cable. An example of a suitable clamping bolt for the device-incorporated clamp is a #8 machine screw made from titanium, stainless steel, cobalt chromium alloy, or a similar type of material that is compatible with material of the device body and clamping body. In some instances, the clamping bolt may be coated with an implantable coating designed to reduce frictional contact with other components of the clamp or device.

The device-incorporated clamp 400 in FIG. 4 is one embodiment of a surgical cable clamp. The embodiment shown in FIG. 4 is an embodiment of the invention that can be used with the structure shown in the preferred environment shown in FIG. 1. Other embodiments of a surgical cable clamp can also be used in the preferred environment and other similar type environments to accomplish similar functions in accordance with the invention.

FIGS. 5a-d illustrate a sequence for a method for using a surgical cable clamp shown in FIGS. 1b and 1c. The particular embodiment shown in this sequence utilizes a device-incorporated clamp, similar to that shown in FIG. 1b as 114 and FIG. 1c as 118. Other embodiments of a surgical cable clamp can be utilized with the method illustrated in FIGS. 5a-d.

As shown in FIG. 5a, a surgical cable clamp 500 is shown incorporated into an orthopedic device such as trochanteric grip 502. The trochanteric grip 502 is aligned with a proximal end of a patient's femur bone 504 in accordance with a hip replacement procedure. When the trochanteric grip 502 is to be secured to the patient's femur 504, the surgical cable clamp 500 is positioned in a position adjacent to the patient's femur 504 to receive a surgical cable 506. Similar to the embodiments shown in FIGS. 1b and 1c, the surgical cable clamp 500 includes a device body, i.e. a portion of the trochanteric grip 502, a clamping bolt 508 and an upper clamping body 510. Typically, the orthopedic device such as a trochanteric grip 502 has an upper surface 512 with a recess 514 sized to receive the upper clamping body 510. The trochanteric grip 502 also has a threaded bolt hole 516 machined through the recess 514 and sized to receive the clamping bolt 508. A relatively smaller diameter end 518 of a predetermined length of surgical cable 506 is inserted into and pulled through a first cable hole 520 in a lateral side of the trochanteric grip 502. A bead 522 on the relatively larger diameter opposing end of the surgical cable 506 secures the opposing end of surgical cable 506 adjacent to the trochanteric grip 502 as shown in FIG. 5b. Preferably, the components of a surgical cable clamp 500 can be preassembled with the orthopedic device prior to the surgical procedure, or otherwise assembled together with the surgical cable 506 during the sequence.

After the surgical cable 506 is wrapped around the thickness of the patient's femur 504, the relatively smaller diameter end 518 of the surgical cable 506 is inserted through a second cable hole 524 of the trochanteric grip 502.

As shown in FIG. 5c, the relatively smaller diameter end 518 and the length of the of the surgical cable 506 is pulled through the second cable hole 524 until a desired tension in the surgical cable 506 is attained. When the surgical cable 506 is pulled to a desired tension, the clamping bolt 508 is mounted through the upper clamping body 510 and tightened into the threaded bolt hole 516 with a tightening instrument (not shown) with a corresponding hexagonal-shaped head or driver such as a "T-handled driver" with a hex head to match the shape of the clamping bolt 508 until the compression force between the upper clamping body 510 and the recess 514 maintains a desired tension on the surgical cable 506. Any excess length of surgical cable 506 can be trimmed with a cutting instrument (not shown).

FIG. 5d illustrates a detailed cutaway cross-sectional view of the surgical cable clamp 500 and trochanteric grip 502 shown in FIGS. 5a-c. As described above and shown here, the upper clamping body 510 is secured to the device body, i.e. a portion of the trochanteric grip 502, with the clamping bolt 508. The position of the surgical cable 506 with respect to the trochanteric grip 502 is maintained by the downward force of the upper clamping body 510 and the clamping bolt 508. A series of corresponding grooves (not shown) or ridges can be machined in the recess 514 of the trochanteric grip 502 adjacent to the position of the surgical cable 506 in order to increase frictional contact on the surgical cable 506.

In most instances, a cable tensioning device (not shown) can be used to tighten the surgical cable 506 to a predetermined tension. The cable tensioning device can be configured to maintain a tension on the surgical cable 506 as well as to measure the tension on the surgical cable 506 until the cable 506 is secured by the clamping bolt 508

More than one surgical cable 506 may be needed to secure an orthopedic device such as a trochanteric grip 502 to a patient's femur 504 or another bone. After tensioning one or more surgical cables 506 to the patient's femur 504 or other bone with one or more corresponding surgical cable clamps 500, previously tensioned surgical cables may tend to loosen or otherwise require additional tension to sufficiently secure the orthopedic device such as a trochanteric grip 502 to the patient's femur 504 or other bone. If necessary, the tension on a previously tensioned surgical cable can be released by applying a force to the clamping bolt 508 with the hexagonal-shaped tightening instrument, releasing the compression force between the upper clamping body 510 and recess 514, thus releasing the tension from the surgical cable 506. The surgical cable 506 is then retensioned manually or by use of the cable tensioning device. When the desired tension is reached, a tightening force is applied to the clamping bolt 508 in order to create a sufficient compression force between the upper clamping body 510 and the recess 514 to maintain the desired tension in the surgical cable 506, and secure the position of the surgical cable 506 relative to the surgical cable clamp 500.

Tensioning and retensioning of one or more surgical cables may occur more than once during a surgical procedure until all of the surgical cables are sufficiently tensioned to maintain the position of the orthopedic device such as a trochanteric grip 502 relative to the patient's femur 504 or other bone. The sequence described above with respect to FIGS. 5a-d can be repeated as necessary to accomplish this.

There are multiple shapes and structures for a surgical cable clamp in accordance with various embodiments of the invention. Without limiting the scope of the invention, the following FIGS. 6-29 are intended to illustrate and describe several embodiments of a surgical cable clamp in accordance with the invention. The surgical cable clamps in each of the embodiments shown in FIGS. 6-29 accomplish similar functions to the embodiments such as the stand alone-type clamp and device-incorporated clamp shown and described above in FIGS. 1-5.

FIG. 6 is a perspective view of another embodiment of a surgical cable clamp 600. The embodiment of the surgical cable clamp 600 shown here includes a clamping body 602, a clamping bolt 604, and a corresponding nut 606.

The clamping body 602 in this embodiment has a generally rounded cap-like configuration with a relatively flat upper surface 608 and a relatively flat lower surface 610. On a circular lateral side 612 of the clamping body 602, a pair of cable holes 614 sized to receive the ends of an orthopedic surgical cable (not shown) are machined through the width of the clamping body 602 to the opposing lateral side. Through the upper surface 608, a bolt hole 616 for receiving the clamping bolt 604 is machined through the thickness of the clamping body 602 to the lower surface 610. A pair of opposing recesses 618 for receiving a portion of the corresponding nut 606 are located on the lateral side 612 of the clamping body 602 opposing one another, and extend from the lower surface 610 towards the upper surface 608. The clamping body 602 includes a concentric nut hole (not shown) in the lower surface 610 sized to receive the width of the corresponding nut 606, and concentrically aligned with the bolt hole 616 through the clamping body 602.

The clamping bolt 604 in this embodiment is shaped similar to a conventional machine screw with a socket head 620, a threaded body 622, and blunt point 624. The socket head 620 is sized to receive a tightening instrument (not shown) for tightening and untightening a corresponding socket-shaped head. Alternatively, the external shape of the socket head 620 can be shaped for tightening with a wrench-type instrument (not shown) for tightening and untightening a corresponding geometrically-shaped socket head 620. The threaded body 622 includes one or more threads 626 sized to receive the corresponding nut 606. The blunt point 624 of the clamping bolt 604 is sized to fit within the bolt hole 616 of the clamping body 602 and to receive the corresponding nut 606.

The corresponding nut 606 is shaped similar to a conventional wingnut with a rounded body 628 and one or more wings 630 extending from opposing lateral sides of the rounded body 628. The rounded body 628 is sized to fit within the concentric nut hole (not shown) in the lower surface 610 of the clamping body 602. A threaded receiving hole 632 is machined through a central portion of the rounded body 630 from an upper side 634 to an opposing lower side 636. Each of the wings 630 is sized to fit within the corresponding opposing recesses 618 in the lateral side 612 of the clamping body 602.

FIG. 7 is an exploded perspective view of another embodiment of a surgical cable clamp similar to that shown in FIG. 6 as 600. The embodiment of the surgical cable clamp 700 shown here includes a clamping body 702, a clamping bolt 704, and a corresponding nut 706, and operates in a similar manner as the embodiment in FIG. 6. The clamping body 702 has a generally rectangular-shaped configuration, while the clamping bolt 704 and associated nut 706 have similar shapes as those shown and described in FIG. 6. The surgical cable clamp 700 shown operates in a substantially similar manner as the clamp shown in FIG. 6 as 600.

FIGS. 8a-b illustrate another embodiment of a surgical cable clamp in accordance with the invention. FIG. 8a shows a cross-sectional view of an embodiment of a surgical cable clamp in an unclamped position, and FIG. 8b shows the clamp of FIG. 8a in a clamped position. This surgical cable clamp 800 includes an upper clamping body 802, a lower clamping body 804, and a clamping bolt 806. Both the upper clamping body 802 and lower clamping body 804 are each generally wedge-shaped. The upper clamping body 802 has an angled surface 808 configured to correspond with a similarly angled surface 810 of the lower clamping body 804 when the clamping bodies are fit together along a relatively flat interface 812. Both the upper clamping body 802 and the lower clamping body each have a corresponding machined bolt hole 814a, 814b through their center portions. The clamping bolt 806 fits within the bolt holes 814a,b when the upper clamping body 802 is aligned with the lower clamping body 804 as shown in FIG. 8a. The clamping bolt 806 may be threaded to correspond with threads of a corresponding nut 816 or with threads machined within the bolt hole 814b of the lower clamping body 804. At least one cable hole 818a is machined in a lateral side 820 of the lower clamping body 804, and a corresponding cable hole 818b is machined in a lateral side 822 of the upper clamping body 802. The cable holes 818a,b are sized to receive an orthopedic surgical cable 824 when the cable holes 818a,b are aligned as shown in FIG. 8a.

When the upper clamping block 802 is slightly offset from the lower clamping block 804 along the interface 812 and the clamping bolt 806 is tightened, then the surgical cable clamp 800 clamps the surgical cable 824 as shown in FIG. 8b. Utilizing this configuration, a user can apply a desired tension to the surgical cable 824, and then clamp the surgical cable 824 by offsetting the upper clamping block 802 from the lower clamping block 804. The compression force of the upper clamping body 802 upon the surgical cable 824 at the interface 812, and the surgical cable 824 against the lower clamping body 804, secures the position of the surgical cable 824 relative to the surgical cable clamp 800. By tightening and untightening the clamping bolt 806 and offsetting or aligning the clamping bodies 802, 804, the surgical cable clamp 800 can clamp and unclamp the orthopedic surgical cable 824.

FIGS. 9a-b illustrate another embodiment of a surgical cable clamp in accordance with the invention. FIG. 9a is a perspective exploded view of a surgical cable clamp; and FIG. 9b is a cross-sectional view of the surgical cable clamp shown in FIG. 9a. In this embodiment, a surgical cable clamp 900 includes an upper clamping body 902, a clamping bolt 904, and a lower clamping body 906. The upper clamping body 902 is generally flat and annularly-shaped, and configured to fit within a corresponding recess 908 in the lower clamping body 906. The lower clamping body 906 is generally block-shaped with the recess 908 machined through a portion of the top surface, and the clamping bolt 904 has a similar shape as the clamping bolt shown and described in FIG. 6. A bolt hole 910 machined through a central portion of the upper clamping body 902 is configured to receive the clamping bolt 904, while a threaded bolt hole 912 is machined in the lower portion of the lower clamping body 906 within the recess 908.

The clamping bolt 904 is threaded to correspond with threads machined within the threaded bolt hole 912. Two cable holes 914 are machined in a lateral side 916 of the lower clamping body 906. The cable holes 914 are sized to receive an orthopedic surgical cable (not shown) to be clamped and reclamped by the surgical cable clamp 900.

When an orthopedic surgical cable is inserted within either or both of the cable holes 914, the upper clamping body 902 can be inserted within the recess 908 of the lower clamping body 906 as shown in FIG. 9*b*. Then the upper clamping body 902 is secured within the recess 908 by the clamping bolt 904 mounted within the bolt hole 910 and threaded within bolt hole 912. The compression force of the upper clamping body 902 upon the surgical cable secures the position of the surgical cable relative to the lower clamping body 906. By tightening and untightening the clamping bolt 904, the surgical cable clamp 900 can clamp and unclamp the orthopedic surgical cable as needed when tensioning the orthopedic surgical cable as desired. A series of grooves (not shown) or ridges can be machined on the lower surface of the upper clamping body to increase the friction or grip on the surgical cable.

FIGS. 10*a*-*b* illustrate another embodiment of a surgical cable clamp in accordance with the invention. FIG. 10*a* is a perspective exploded view of a surgical cable clamp; and FIG. 10*b* is a cross-sectional view of the surgical cable clamp shown in FIG. 10*a*. In this embodiment, a surgical cable clamp 1000 includes a upper clamping body 1002, a lower clamping body 1004, and a clamping bolt 1006. The upper clamping body 1002 is generally C-shaped with a lower recess 1008 sized to receive the generally rectangular-shaped lower clamping body 1004. When fit together, the lower clamping body 1004 integrally fits with the upper clamping body 1002 as shown in FIG. 10*b*. The clamping bolt 1006 fits within a bolt hole 1010 machined through the central portion of the upper clamping body 1002, and has a similar shape as the clamping bolt shown and described in FIG. 6. A threaded bolt hole 1012 machined in the lower clamping body 1004 is sized to receive threads of the clamping bolt 1006. Two cable channels 1014 are machined in the lower portion of a lateral side 1016 of the upper clamping body 1002. These cable channels 1014 correspond with cable channels 1018 machined in an upper portion of the lower clamping body 1004. When the upper clamping body 1002 and lower clamping body 1004 are integrally fit together, the cable channels 1014, 1018 align with each other. The cable channels 1014, 1018 are sized to receive an orthopedic surgical cable (not shown) to be clamped and reclamped by the surgical cable clamp 1000. A series of grooves (not shown) or ridges can be machined within the cable channels 1014, 1018 to increase the friction or grip on the surgical cable.

When an orthopedic surgical cable is inserted within either or both of the cable holes, the upper clamping body 1002 is fit together with the lower clamping body 1004, and then the upper clamping body 1002 is secured to the lower clamping body 1004 by the clamping bolt 1006. The compression force of the upper clamping body 1002 upon the surgical cable secures the position of the cable relative to the lower clamping body 1004. By tightening and untightening the clamping bolt 1006, the surgical cable clamp 1000 can clamp and unclamp the orthopedic surgical cable as needed when tensioning the orthopedic surgical cable as desired.

FIGS. 11*a*-*b* illustrate another embodiment of a surgical cable clamp in accordance with the invention. FIG. 11*a* is a perspective exploded view of a surgical cable clamp; and FIG. 11*b* is a cross-sectional view showing clamp position of the surgical cable clamp shown in FIG. 11*a*. The embodiment of a surgical cable clamp 1100 shown here includes a clamping body 1102, a clamping bolt 1104, and a corresponding nut 1106, and operates in a similar manner as the embodiment in FIG. 6. The clamping body 1102 has a generally block-shaped configuration with a recess 1108 in the lower surface, while the clamping bolt 1104 has a similar shape as the clamping bolt shown and described in FIG. 6. The corresponding nut 1106 is annular shaped with a wedge-shaped cross-section, configured to fit within the circular-shaped recess 1108 in the clamping body 1102. A bolt hole 1110 machined through the central portion of the clamping body 1102 corresponds with a threaded bolt hole 1112 in the corresponding nut 1106. When the clamping body 1102 and the corresponding nut 1106 are aligned, the clamping bolt mounts through the bolt hole 1110 and threads into the threaded bolt hole 1112 of the corresponding nut 1106. Two cable holes 1114 are machined in a lateral side 1116 of the clamping body 1102. Each cable hole 1114 extends along a portion of the lateral edge of the recess 1108 within the clamping body 1102, and through to the opposing lateral side of the clamping body 1102.

When an orthopedic surgical cable is inserted within either or both the cable holes 1114, the clamping body 1102 can then be fit together with the corresponding nut 1106. The corresponding nut 1106 is secured to the clamping body 1102 by the clamping bolt 1104. The compression force of the corresponding nut 1106 upon the surgical cable secures the position of the cable relative to the clamping body 1102. By tightening and untightening the clamping bolt 1104, the surgical cable clamp 1100 can clamp and unclamp the orthopedic surgical cable as needed when tensioning the orthopedic surgical cable as desired.

FIGS. 12*a*-*b* illustrate another embodiment of a surgical cable clamp in accordance with the invention. FIG. 12*a* is a side view of the surgical cable clamp in an unclamped position, and FIG. 12*b* is a side view of the surgical cable clamp in FIG. 12*a* in a clamped position. In this embodiment, a surgical cable clamp 1200 includes a upper clamping body 1202, a lower clamping body 1204, and a spring 1206. The upper clamping body 1202 is configured to hingably fit together with the lower clamping body 1204 via a hinge 1208. Together, the upper clamping body 1202 connected to the lower clamping body 1204 form a C-shaped device. A cable support 1210 connects to the upper clamping body 1202, while a corresponding cable support 1212 connects to the lower clamping body 1204. Each of the cable supports 1210, 1212 is eye bolt-shaped. When the clamp 1200 is in an unclamped position as shown in FIG. 12*a*, the cable supports 1210, 1212 align with each other, as well as with a cable hole 1214 adjacent to the hinge 1208 and between adjacent ends of the upper clamping body 1202 and lower clamping body 1204.

The spring 1206 mounts between and connects the upper clamping body 1202 and lower clamping body 1204, adjacent to the hinge 1208. When the clamp 1200 is in a clamped position as shown in FIG. 12*b*, the spring 1206 maintains the upper clamping body 1202 and lower clamping body 1204 in a spaced apart relation that offsets the alignment of the cable supports 1210, 1212. For example, when an orthopedic surgical cable 1216 is mounted through the cable hole 1214 and through each of the aligned cable supports 1210, 1212 as shown in FIG. 12*a*, the surgical cable clamp 1200 does not provide any clamping force upon the cable 1216. However, as shown in FIG. 12*b*, when the upper clamping body 1202 and lower clamping body 1204 are extended away from each other, the offset alignment of the cable supports 1210, 1212 causes the surgical cable clamp 1200 to slightly offset or "clamp" the cable 1216, thus securing the position of the surgical cable 1216 relative to the surgical cable clamp 1200. By compressing or extending the upper and lower clamping bodies 1202, 1204 together or away from each other, the surgical cable clamp 1200 can clamp and unclamp the orthopedic surgical cable 1216 as needed when tensioning the orthopedic surgical cable 1216 as desired.

FIGS. 13*a-b* illustrate another embodiment of a surgical cable clamp in accordance with the invention. FIG. 13*a* is a cross-sectional view of the surgical cable clamp in a clamped position, and FIG. 13*b* is an exploded side view of the surgical cable clamp in FIG. 13*a* in an unclamped position. In this embodiment, a surgical cable clamp 1300 includes a upper clamping body 1302, a lower clamping body 1304, and a pair of clamping bolts 1306. The wedge-shaped upper clamping body 1302 is configured to integrally fit within a corresponding recess 1308 of the lower clamping body 1304. Together, the upper clamping body 1302 and lower clamping body 1304 form a general block-shape. The clamping bolts 1306 each have a similar shape as the clamping bolt shown and described in FIG. 6. A set of bolt holes 1310 in the upper clamping body 1302 correspond with threaded bolt holes 1312 in the lower clamping body 1304. Each of the bolt holes 1310, 1312 is sized to receive the clamping bolts 1306.

At least one cable hole 1314 is machined in a lateral side 1316 of the lower clamping body 1304. At an interface between the upper clamping body 1302 and lower clamping body 1304, a second cable hole 1318 is formed when the upper clamping body 1302 fits together with the lower clamping body 1304. For example, a tip portion 1320 of the upper clamping body 1302 can be a concave-shaped tip, and the recessed portion 1322 of the lower clamping body 1304 can be a concave-shaped recess that corresponds to the tip portion of the upper clamping body 1302 to form a second cable hole 1318. The cable hole 1310 and second cable hole 1318 are sized to receive an orthopedic surgical cable (not shown) to be clamped and reclamped by the surgical cable clamp 1300.

When an orthopedic surgical cable is inserted within either or both the cable hole 1310 and second cable hole 1318, the upper clamping body 1302 can then be secured together with the lower clamping body 1304 by the clamping bolts 1306. The compression force of the upper clamping body 1302 upon the surgical cable secures the position of the cable relative to the lower clamping body 1304. By tightening and untightening the clamping bolts 1306, the surgical cable clamp can clamp and unclamp the orthopedic surgical cable as needed when tensioning the orthopedic surgical cable as desired. A series of grooves (not shown) or ridges to increase the friction or grip on the surgical cable can be machined within the second cable hole 1318 by machining the upper clamping body 1302 and/or lower clamping body 1304.

FIGS. 14*a-b* show another embodiment of a surgical cable clamp in accordance with the invention. FIG. 14*a* is a side view of the surgical cable clamp in a clamped position, and FIG. 14*b* is a side view of the surgical cable clamp in FIG. 14*a* in an unclamped position. In this embodiment, a surgical cable clamp 1400 includes an upper clamping body 1402, a lower clamping body 1404, and a clamping bolt 1406. The upper clamping body 1402 is configured to hingably fit together with the lower clamping body 1404 via a hinge 1408. Together, the upper clamping body 1402 and lower clamping body 1404 form a V-shape. A bolt hole 1410 in the upper clamping body 1402 adjacent to an unhinged end corresponds with a threaded bolt hole 1412 in the lower clamping body 1404 adjacent to its unhinged end. Each of the bolt holes 1410, 1412 are sized to receive the clamping bolt 1406. The clamping bolt 1406 has a similar shape as the clamping bolt shown and described in FIG. 6.

At least one cable hole 1414 is machined in a lateral side 1416 of the upper clamping body 1402. At an interface between the upper clamping body 1402 and lower clamping body 1404, a second cable hole 1418 is formed when the upper clamping body 1402 fits together with the lower clamping body 1404. For example, a recessed portion 1420 of the upper clamping body 1402 can be a concave-shaped cable channel, and a recessed portion 1422 of the lower clamping body 1404 can be a concave-shaped cable channel that corresponds to the recessed portion 1420 of the upper clamping body 1402 to form a second cable hole 1418. The cable hole 1410 and second cable hole 1418 are sized to receive an orthopedic surgical cable (not shown) to be clamped and reclamped by the surgical cable clamp 1400.

When an orthopedic surgical cable is inserted within either or both the cable hole 1410 and second cable hole 1418, the upper clamping body 1402 can then be secured together with the lower clamping body 1404 by the clamping bolt 1406. The compression force of the upper clamping body 1402 upon the surgical cable secures the position of the cable relative to the lower clamping body 1404. By tightening and untightening the clamping bolt 1406, the surgical cable clamp 1400 can clamp and unclamp the orthopedic surgical cable as needed when tensioning the orthopedic surgical cable as desired. A series of grooves (not shown) or ridges to increase the friction or grip on the surgical cable can be machined within the second cable hole 1418 by machining the upper clamping body 1402 and/or lower clamping body 1404.

FIGS. 15*a-b* illustrate another embodiment of a surgical cable clamp in accordance with the invention. FIG. 15*a* is a cross-sectional view of the surgical cable clamp in a clamped position, and FIG. 15*b* is an exploded side view of the surgical cable clamp in FIG. 15*a* in an unclamped position. In this embodiment, a surgical cable clamp 1500 includes an upper clamping body 1502, a lower clamping body 1504, and a pair of clamping bolts 1506. The lower clamping body 1504 forms an inverted T-shape and integrally fits within a corresponding recess 1508 in the lower portion of the upper clamping body 1502. The clamping bolts 1506 fit within a pair of respective bolt holes 1510 machined through portions of the upper clamping body 1502 and within corresponding threaded bolt holes 1512 machined in the lower clamping body 1504. Note that the clamping bolts 1506 each have a similar shape as the clamping bolt shown and described in FIG. 6. At least one cable hole 1514 is machined in a lateral side 1516 of the upper clamping body 1502. A second cable hole 1518 is formed when the upper clamping body 1502 is fit together with the lower clamping body 1504. For example, a tip portion 1520 of the T-shaped lower clamping body 1504 can have a concave-shaped tip and a corresponding recessed portion 1522 in the upper clamping body 1502 can be a concave-shaped portion that forms a second cable hole 1518 when the upper clamping body 1502 is integrally fit together with the lower clamping body 1504. The cable hole 1510 and second cable hole 1518 are sized to receive an orthopedic surgical cable (not shown) to be clamped and reclamped by the surgical cable clamp 1500.

One or more springs 1524 may be positioned between the upper clamping body 1502 and the lower clamping body 1504 to assist with the disassembly of the upper clamping body 1502 from the lower clamping body 1504. In the example shown, the springs 1524 are concentrically positioned around the clamping bolts 1506, and are configured to compress when the lower clamping body 1502 is compressed within the recess 1508 of the upper clamping body as shown in FIG. 15a.

When an orthopedic surgical cable is inserted within either or both the cable hole 1510 and second cable hole 1518, the lower clamping body 1504 can then be fit together with the upper clamping body 1502, and then the lower clamping body 1504 is secured to the upper clamping body 1502 by the clamping bolts 1506. The compression force of the lower clamping body 1504 upon the surgical cable secures the position of the cable relative to the upper clamping body 1502. By tightening and untightening either or both of the clamping bolts 1506, the surgical cable clamp 1500 can clamp and unclamp the orthopedic surgical cable as needed when tensioning the orthopedic surgical cable as desired. A series of grooves (not shown) or ridges to increase the friction or grip on the surgical cable can be machined within the second cable hole 1518 by machining the upper clamping body 1502 and/or lower clamping body 1504.

FIGS. 16a-b show another embodiment of a surgical cable clamp in accordance with the invention. FIG. 16a is a cross-sectional view of the surgical cable clamp in a clamped position, and FIG. 16b is a isometric or perspective view of the surgical cable clamp in FIG. 16a in an unclamped position. In this embodiment, a surgical cable clamp 1600 includes an upper clamping body 1602, a lower clamping body 1604, and a clamping bolt 1606. The cone-shaped lower clamping body 1604 is configured to integrally fit within a corresponding recess 1608 machined in the lower portion of the upper clamping body 1602. The clamping bolt 1606 fits within a bolt hole 1610 machined through a central portion of the upper clamping body 1602, and within a threaded bolt hole 1612 machined in a central portion of the lower clamping body 1604. Note that the clamping bolt 1606 has a similar shape as the clamping bolt shown and described in FIG. 6. At an interface between the lateral sides 1614 of the lower clamping body 1604 and the lateral sides 1616 of the recess 1608, cable clamping areas 1618 are formed when the lower clamping body 1604 is integrally fit within the recess 1608 of the upper clamping body 1602. For example, the lateral sides 1616 of the recess 1608 can each have a pair of concave-shaped recessed portions that are adjacent to the lower clamping body 1604, when the lower clamping body 1604 is fit into the recess 1608. The cable clamping areas 1618 are sized to receive an orthopedic surgical cable (not shown) to be clamped and reclamped by the surgical cable clamp 1600. Thus, when the lower clamping body 1604 is drawn upwards and into the recess 1608 of the upper clamping body 1602, the cable clamping areas 1618 are restricted by the lateral sides 1614 of the lower clamping body 1604.

Cable holes 1620 machined in a lateral side 1622 of the upper clamping body 1602 and through to the opposing later side further align with the cable clamping areas 1618 to permit an orthopedic surgical cable (not shown) to mount through the upper clamping body 1602. When an orthopedic surgical cable is inserted into either or both cable holes 1620 and within either or both corresponding cable clamping areas 1618, the lower clamping body 1604 can then be secured to the upper clamping body 1602 by the clamping bolt 1606. The compression force of the lower clamping body 1604 upon the surgical cable secures the position of the cable relative to the upper clamping body 1602. By tightening and untightening the clamping bolt 1606, the surgical cable clamp 1600 can clamp and unclamp the orthopedic surgical cable as needed when tensioning the orthopedic surgical cable as desired. A series of grooves (not shown) or ridges to increase the friction or grip on the surgical cable can be machined within the along the lateral sides of the lower clamping body 1604 adjacent to the cable clamping areas 1618.

FIGS. 17a-b illustrate another embodiment of a surgical cable clamp in accordance with the invention. FIG. 17a is a cross-sectional view of the surgical cable clamp in a clamped position, and FIG. 17b is an isometric view or perspective view of the surgical cable clamp in FIG. 17a. In this embodiment, a surgical cable clamp 1700 includes a upper clamping body 1702, a lower clamping body 1704, and a clamping bolt 1706. The lower clamping body 1702 is a tapered wedge-shape configured to integrally fit within a corresponding recess 1708 machined in the lower portion of the upper clamping body 1704. The clamping bolt 1706 mounts through a bolt hole 1710 machined through a central portion of the upper clamping body 1702, and within a threaded bolt hole 1712 machined in the lower clamping body 1704. The clamping bolt 1706 may be threaded to correspond with threads machined within bolt hole 1712. Note that the clamping bolt 1706 has a similar shape as the clamping bolt shown and described in FIG. 6. Two cable holes 1714 are machined in a lateral side 1716 of the lower clamping body 1704. At an interface between the upper clamping body 1702 and lower clamping body 1704, a cable clamping area 1718 is formed when the lower clamping body 1704 is integrally fit together with the upper clamping body 1702. At least one of the cable holes 1714 aligns with the cable clamping area 1718. The cable clamping area 1718 is sized to receive an orthopedic surgical cable to be clamped and reclamped by the surgical cable clamp 1700. Thus, when the lower clamping body is drawn upwards and into the recess of the upper clamping body, the cable clamping area 1718 is further restricted by the lower clamping body 1704.

At least one ball spring 1720 is connected to the lower clamping body 1704 and configured to extend between the upper clamping body 1702 and the lower clamping body 1704. The ball spring 1720 assists with the assembly of the lower clamping body 1704 with the upper clamping body 1702. When the surgical cable clamp 1700 is assembled as shown in FIG. 17a, the ball spring 1720 compresses when the lower clamping body 1704 is initially drawn upward within the recess 1708 of the upper clamping body 1702. Conversely, the ball spring 1720 extends into a corresponding ball recess 1722 machined in an opposing lateral side 1724 of the recess 1708 when a predetermined position is reached by the lower clamping body 1704 with respect to the upper clamping body 1702. When the predetermined position is attained, the ball spring 1720 provides a physical stop preventing an undesired release of cable tension caused by the clamping bolt 1706 possibly backing out while in use.

When an orthopedic surgical cable 1726 is inserted within either or both cable clamping areas, the lower clamping body 1704 can then be secured to the upper clamping body 1702 by the clamping bolt 1706. The compression force of the lower clamping body 1704 upon the surgical cable 1726 secures the position of the cable 1726 relative to the upper clamping body 1702. By tightening and untightening the clamping bolt 1706, the surgical cable clamp 1700 can clamp and unclamp the orthopedic surgical cable 1726 as needed when tensioning the orthopedic surgical cable 1726 as desired.

FIGS. 18*a-b* show another embodiment of a surgical cable clamp in accordance with the invention. FIG. 18*a* is an exploded isometric view of the surgical cable clamp in an unclamped position, and FIG. 18*b* is a cross-sectional view showing the clamp position of the surgical cable clamp in FIG. 18*a*. In this embodiment, a surgical cable clamp 1800 includes a clamping body 1802 and a collet 1804. The clamping body 1802 is configured to fit together with the collet 1804 so that the collet 1804 compresses a portion of the clamping body 1802. The clamping body 1802 includes a pair of extended legs 1806*a,b*. A cable clamping area 1808 is formed between the extended legs 1806*a,b*, while opposing cable channels 1810 are machined on the interior lateral sides of each leg 1806*a,b*. The cable channels 1810 and cable clamping areas 1808 are sized to receive the diameter of an orthopedic surgical cable to be clamped and reclamped by the surgical cable clamp 1800. A cable hole 1812 machined through the clamping body 1802 is also sized to receive the diameter of an orthopedic surgical cable to be clamped and reclamped by the surgical cable clamp 1800.

When an orthopedic surgical cable is inserted within the cable clamping area 1808 and within the cable channels 1810, the extended legs 1806*a,b* can then be compressed towards each other with the collet 1804. The compression force of the collet 1804 upon the extended legs 1806*a,b* applies a compression force on the surgical cable, thus securing the position of the cable relative to the clamping body 1802. By tightening and untightening the collet 1804, the surgical cable clamp 1800 can clamp and unclamp the orthopedic surgical cable as needed to secure or unsecure the tension in the cable as desired. A series of grooves (not shown) or ridges to increase the friction or grip on the surgical cable can be machined within the cable channels 1810 by machining the interior lateral sides of each leg 1806*a,b*. Other configurations of sizes and shapes for a collet 1804 or similar shaped body or device can be used in accordance with the invention.

FIGS. 19*a-b* show another embodiment of a surgical cable clamp in accordance with the invention. FIG. 19*a* is an exploded isometric view of the surgical cable clamp in an unclamped position, and FIG. 19*b* is a cross-sectional view showing the clamp position of the surgical cable clamp in FIG. 19*a*. In this embodiment, which is similar to the embodiment shown in FIG. 18, a surgical cable clamp 1900 includes a clamping body 1902 and a collet 1904. However, in this embodiment, the collet 1904 is configured to thread onto the clamping body 1902, rather than a slip fit, so that the collet 1904 compresses a portion of the clamping body 1902. The clamping body 1902 includes a pair of extended legs 1906*a,b*. A cable clamping area 1908 is formed between the extended legs 1906*a,b*, while opposing cable channels 1910 are machined on the interior lateral sides of each leg 1906*a,b*. The cable channels 1910 and cable clamping area 1908 are sized to receive the diameter of an orthopedic surgical cable to be clamped and reclamped by the surgical cable clamp 1900. A cable hole 1912 machined through the clamping body 1902 is also sized to receive the diameter of an orthopedic surgical cable to be clamped and reclamped by the surgical cable clamp 1900.

When an orthopedic surgical cable is inserted within the cable clamping area 1908 and within the cable channels 1910, the extended legs 1906*a,b* can then be compressed towards each other with the collet 1904. The compression force of the collet 1904 upon the extended legs 1906*a,b* applies a compression force on the surgical cable, thus securing the position of the cable relative to the clamping body 1902. By tightening and untightening the collet 1904, the surgical cable clamp 1900 can clamp and unclamp the orthopedic surgical cable as needed when tensioning the orthopedic surgical cable as desired. A series of grooves (not shown) or ridges to increase the friction or grip on the surgical cable can be machined within the cable channels 1910 by machining the interior sides of each leg 1906*a,b*.

Note that the collet 1904 can be a cylindrically-shaped compression piece sized to fit on the ends of the extended legs 1906*a,b*. Alternatively, the collet 1904 can be a cylindrically-shaped threaded piece with corresponding threads configured on the exterior of the extended legs 1906*a,b* to receive the threaded collet 1904. Other configurations of sizes and shapes for a collet 1904 or similar shaped body or device can be used in accordance with the invention.

FIG. 20*a* is another embodiment of a surgical cable clamp in accordance with the invention. FIG. 20*a* is a perspective exploded view of a surgical cable clamp in an unclamped position; and FIG. 20*b* is a cross-sectional view showing the clamp position of the surgical cable clamp shown in FIG. 20*a*. In this embodiment, a surgical cable clamp 2000 includes a upper clamping body 2002, a lower clamping body 2004, and a clamping bolt 2006. The upper clamping body 2002 is generally disc-shaped with a pair of cable channels 2008 machined in along the lower portion and sized to receive a diameter of an orthopedic surgical cable 2010 to be clamped and reclamped by the surgical cable clamp 2000. The lower clamping body 2004 is also generally disc-shaped and integrally fits with the upper clamping body 2002 as shown in FIG. 20*b*. The clamping bolt 2006 fits within a bolt hole 2012 machined through the central portion of the upper clamping body 2002, and has a similar shape as the clamping bolt shown and described in FIG. 6. A threaded bolt hole 2014 machined in the lower clamping body 1004 is sized to receive threads of the clamping bolt 2006.

When an orthopedic surgical cable is inserted between the upper clamping body 2002 and the lower clamping body 2004, and within at least one cable channel 2008, then the upper clamping body 2002 can be secured to the lower clamping body 2004 by the clamping bolt 2006. The compression force of the upper clamping body 2002 upon the surgical cable 2010 secures the position of the cable 2010 relative to the lower clamping body 2004. By tightening and untightening the clamping bolt 2006, the surgical cable clamp 2000 can clamp and unclamp the orthopedic surgical cable 2010 as needed when tensioning the orthopedic surgical cable 2010 as desired. A series of grooves (not shown) or ridges can be machined within the cable channels 2008 and/or along the opposing side of the lower clamping body 2004 to increase the friction or grip on the surgical cable.

FIGS. 21*a-b* is another embodiment of a surgical cable clamp in accordance with the invention. FIG. 21 illustrates a perspective view of a surgical cable clamp in a clamped position; and FIG. 21b illustrates a cross-sectional view showing the clamp position of the surgical cable clamp shown in FIG. 21a also in a clamped position. In this embodiment, a surgical cable clamp 2100 includes a upper clamping body 2102, a lower clamping body 2104, and a clamping bolt 2106. The upper clamping body 2102 is generally wedge-shaped. The lower clamping body 2104 is generally disc-shaped with a corresponding wedge-shaped taper between an upper surface 2108 and lateral surface 2110 of the body 2104. The upper clamping body 2102 integrally fits with the lower clamping body 2104 as shown in FIG. 21b. The clamping bolt 2106 fits within a bolt hole 2112 machined through the central portion of the upper clamping body 2102, and has a similar shape as the clamping bolt shown and described in FIG. 6. A threaded bolt hole 2114 machined in the tapered portion of the lower clamping body 1004 is sized to receive threads of the clamping bolt 2006.

A cable hole 2116 and a cable channel 2118 are machined through the lateral side 2110 of the lower clamping body 2104, and each is sized to receive a diameter of an orthopedic surgical cable 2120 to be clamped and reclamped by the surgical cable clamp 2100. The cable channel 2118 is machined along the tapered portion of the lower clamping body 2104, permitting the upper clamping body 2102 to contact a portion of the surgical cable 2120 when the cable 2120 is mounted within the cable channel 2118.

When an orthopedic surgical cable is inserted between the upper clamping body 2102 and the lower clamping body 2104, and within the cable channel 2118, then the upper clamping body 2102 can be secured to the lower clamping body 2104 by the clamping bolt 2106. The compression force of the upper clamping body 2102 upon the surgical cable 2120 secures the position of the cable 2120 relative to the lower clamping body 2104. By tightening and untightening the clamping bolt 2106, the surgical cable clamp 2100 can clamp and unclamp the orthopedic surgical cable 2120 as needed when tensioning the orthopedic surgical cable 2120 as desired. A series of grooves (not shown) or ridges can be machined within the cable channel 2118 and/or along the opposing side of the upper clamping body 2102 to increase the friction or grip on the surgical cable.

FIGS. 22a-b are another embodiment of a surgical cable clamp in accordance with the invention. FIG. 22a illustrates a cross-sectional view of a surgical cable clamp in an unclamped position; and FIG. 22b illustrates a cross-sectional view showing the clamp position of the surgical cable clamp shown in FIG. 22a. In this embodiment, a surgical cable clamp 2200 includes a upper clamping body 2202 and a lower clamping body 2204. The upper clamping body 2202 is generally a cylindrically-shaped tube with slotted lateral sides 2206. The lower clamping body 2204 is generally spherically-shaped with slots 2208 in its lateral sides 2210 that correspond with slots 2212 in the upper clamping body 2202. The upper clamping body 2202 integrally fits with the lower clamping body 2204 as shown in FIGS. 22a-b. Conventional material joining methods and processes can be used to fit the upper clamping body 2202 with the lower clamping body 2204, or alternatively, the bodies 2202, 2204 can be molded or otherwise formed from a single piece or material.

A cable hole 2214 is machined through the lower clamping body 2204 to receive a diameter of an orthopedic surgical cable 2216 to be clamped and reclamped by the surgical cable clamp 2200. A cable channel 2218 in the upper clamping body 2202 is aligned with the cable hole 2214, and is also configured to receive a diameter of an orthopedic surgical cable 2216. The cable channel 2218 permits the upper clamping body 2202 to contact a portion of the surgical cable 2216 when the cable 2216 is mounted within the cable channel 2218.

When an orthopedic surgical cable is inserted within the cable hole 2214 and mounted within the cable channel 2218, the cable clamp 2200 can be inserted into a cavity 2220 of an orthopedic device 2222 as shown in FIG. 22a. This movement causes a compression force to be applied to the exterior of the lower clamping body 2204 causing the lateral sides 2206 of the upper clamping body 2202 to move inward towards the surgical cable 2216 as shown in FIG. 22b. The compression force of the upper clamping body 2202 upon the surgical cable 2216 secures the position of the cable 2216 relative to the lower clamping body 2204. When a user inserts or removes the lower clamping body from the cavity 2220, the surgical cable clamp 2200 clamps or unclamps the orthopedic surgical cable 2216 as needed when tensioning the orthopedic surgical cable 2216 as desired. A series of grooves (not shown) or ridges can be machined within the cable channel 2218 and/or along the opposing sides of the upper clamping body 2202 to increase the friction or grip on the surgical cable.

FIGS. 23a-b are another embodiment of a surgical cable clamp in accordance with the invention. FIG. 23a illustrates a cross-sectional view of a surgical cable clamp in an unclamped position; and FIG. 23b illustrates a cross-sectional view showing the clamp position of the surgical cable clamp shown in FIG. 23a. In this embodiment, a surgical cable clamp 2300 includes a clamping body 2302. The clamping body of this embodiment is a single molded or manufactured piece, but could be fabricated in multiple pieces similar to the embodiment shown in FIG. 22. The clamping body 2302 is generally a wedge-shaped tube with slotted lateral sides 2304. A cable hole 2306 is machined through the clamping body 2302 to receive a diameter of an orthopedic surgical cable 2308 to be clamped and reclamped by the surgical cable clamp 2300. The cable hole 2306 permits the clamping body 2302 to contact a portion of the surgical cable 2308 when the cable 2308 is mounted within the cable hole 2306.

When an orthopedic surgical cable 2308 is inserted within the cable hole 2306, the cable clamp 2300 can be inserted into a cavity 2310 of an orthopedic device 2312 as shown in FIG. 23a. This movement causes a compression force to be applied to the exterior of the clamping body 2302 causing the lateral sides 2304 of the clamping body 2302 to move inward towards the surgical cable 2308 as shown in FIG. 23b. The compression force of the clamping body 2302 upon the surgical cable 2308 secures the position of the cable 2308 relative to the clamping body 2302. When a user inserts or removes the lower clamping body from the cavity 2310, the surgical cable clamp 2300 clamps or unclamps the orthopedic surgical cable 2308 as needed when tensioning the orthopedic surgical cable 2308 as desired. A series of grooves (not shown) or ridges can be machined within the cable hole 2306 and/or along the opposing sides of the upper clamping body 2302 to increase the friction or grip on the surgical cable.

FIGS. 24a-b illustrate another embodiment of a surgical cable clamp in accordance with the invention. FIG. 24a shows a perspective view of a surgical cable clamp, and FIG. 24b shows a cross-sectional view of the surgical cable clamp shown in FIG. 24a. In this embodiment, a surgical cable clamp 2400 includes a clamping body 2402, and a clamping mechanism 2404. The clamping body 2402 is geometrically shaped with at least one clamping cable hole 2406 machined through the thickness of the body 2402. The clamping cable hole 2406 shown includes a machined out portion 2408 that permits the size of the corresponding clamping cable hole 2406 to be slightly reduced when the clamping body 2402 is compressed. In the configuration shown, the clamping body 2402 has an upper portion 2410 and a lower portion 2412 adjacent to the machined out portion 2408 of the cable hole 2406. The clamping mechanism 2404 is a C-shaped ring that fits within a ridge 2414 that is machined partially around the exterior sides of the upper portion 2410 and lower portion 2412 of the clamping body 2402.

The clamping cable hole 2406 is sized to receive a diameter of an orthopedic surgical cable 2416 to be clamped and reclamped by the surgical cable clamp 2400. When the upper portion 2410 of the clamping body 2402 is compressed towards the lower portion 2412 of the clamping body, the cable hole 2406 compresses slightly to contact a portion of the surgical cable 2416 when the cable 2416 is mounted within the cable hole 2406.

When an orthopedic surgical cable 2416 is inserted between the upper portion 2410 of the clamping body 2402 and the lower portion 2412 of the clamping body 2104, and within the clamping cable hole 2406, then the upper portion 2410 can be secured with respect to the lower clamping body 2412 by positioning the clamping mechanism 2404 within the ridge 2414 and activating the clamping mechanism 2404. The compression force of the clamping mechanism 2404 upon the upper 2410 and lower portions 2412 of the clamping body 2402 compresses the interior sides of the cable hole 2406 upon the surgical cable 2416, while securing the position of the cable 2416 relative to the clamping body 2402. By tightening and untightening the clamping mechanism 2404, the surgical cable clamp 2400 can clamp and unclamp the orthopedic surgical cable 2416 as needed when tensioning the orthopedic surgical cable 2416 as desired. A series of grooves (not shown) or ridges can be machined within the cable hole 2406 to increase the friction or grip on the surgical cable.

Note that the clamping mechanism 2404 can be a material having elastic-like or shape-memory properties, such as nitinol, a memory metal, a material activated by temperature change or heat, a material activated by a force, a material activated by an electrical current, or a material activated by a magnetic force. Other metals, plastics, alloys, composites, or other materials can be used within a clamping mechanism to provide the desired effects. When activated or otherwise in use, the clamping mechanism 2404 is designed to apply a compression force to the clamping body 2402. In the configuration shown in FIGS. 24a-b, the clamping mechanism 2404 compresses the upper 2410 and lower portions 2412 of the clamping body 2402 towards each other, reducing the diameter of the cable hole 2406 and clamping a surgical cable within the cable hole 2406. When the clamping mechanism 2404 is deactivated or otherwise not in use, the clamping mechanism 2404 does not apply a compression force to the clamping body 2402, and the diameter of the cable hole 2406 returns to a normal, unreduced size or position.

FIGS. 25a-b illustrate another embodiment of a surgical cable clamp in accordance with the invention. FIG. 25a is a perspective exploded view of a surgical cable clamp; and FIG. 25b is a cross-sectional view of the surgical cable clamp shown in FIG. 25a. The embodiment of a surgical cable clamp 2500 shown here includes a clamping body 2502, and a clamping mechanism 2504. The clamping body 2502 has a generally block-shaped configuration with a circular-shaped recess 2506 in the upper surface, while the clamping nut 2504 is disc shaped to correspondingly fit within the recess 2506 of the clamping body 2502. Typically, the clamping mechanism 2504 is threaded to fit corresponding threads machined in the lateral sides 2508 of the recess 2506. When the clamping body 2502 and the clamping mechanism 2504 are aligned, the clamping mechanism 2504 mounts to the clamping body 2502 with preferably a quarter radial turn of the clamping mechanism 2504 with respect to the clamping body 2502. Other embodiments can provide additional or less threading to secure the clamping mechanism 2504 to the clamping body 2502 using less than or greater than a quarter radial turn. One or more cable holes 2510 are machined in a lateral side 2512 of the clamping body 2502. Each cable hole 2510 extends along and through a portion of the recess 2506 within the clamping body 2502, and through to the opposing lateral side of the clamping body 2502.

When an orthopedic surgical cable 2514 is inserted within the cable hole 2510 as shown, the clamping body 2502 can then be fit together with the clamping mechanism 2504. The clamping mechanism 2504 is secured to the clamping body 2502 by threading the clamping mechanism 2504 into the recess 2506. The compression force of the clamping mechanism 2504 upon the surgical cable 2514 secures the position of the cable 2514 relative to the clamping body 2502. By tightening and untightening the clamping mechanism 2504, the surgical cable clamp 2500 can clamp and unclamp the orthopedic surgical cable 2514 as needed when tensioning the orthopedic surgical cable as desired. A series of grooves (not shown) or ridges can be machined along and within the cable hole 2510 and/or the opposing side of the clamping mechanism 2504 to increase the friction or grip on the surgical cable.

Figure 27:
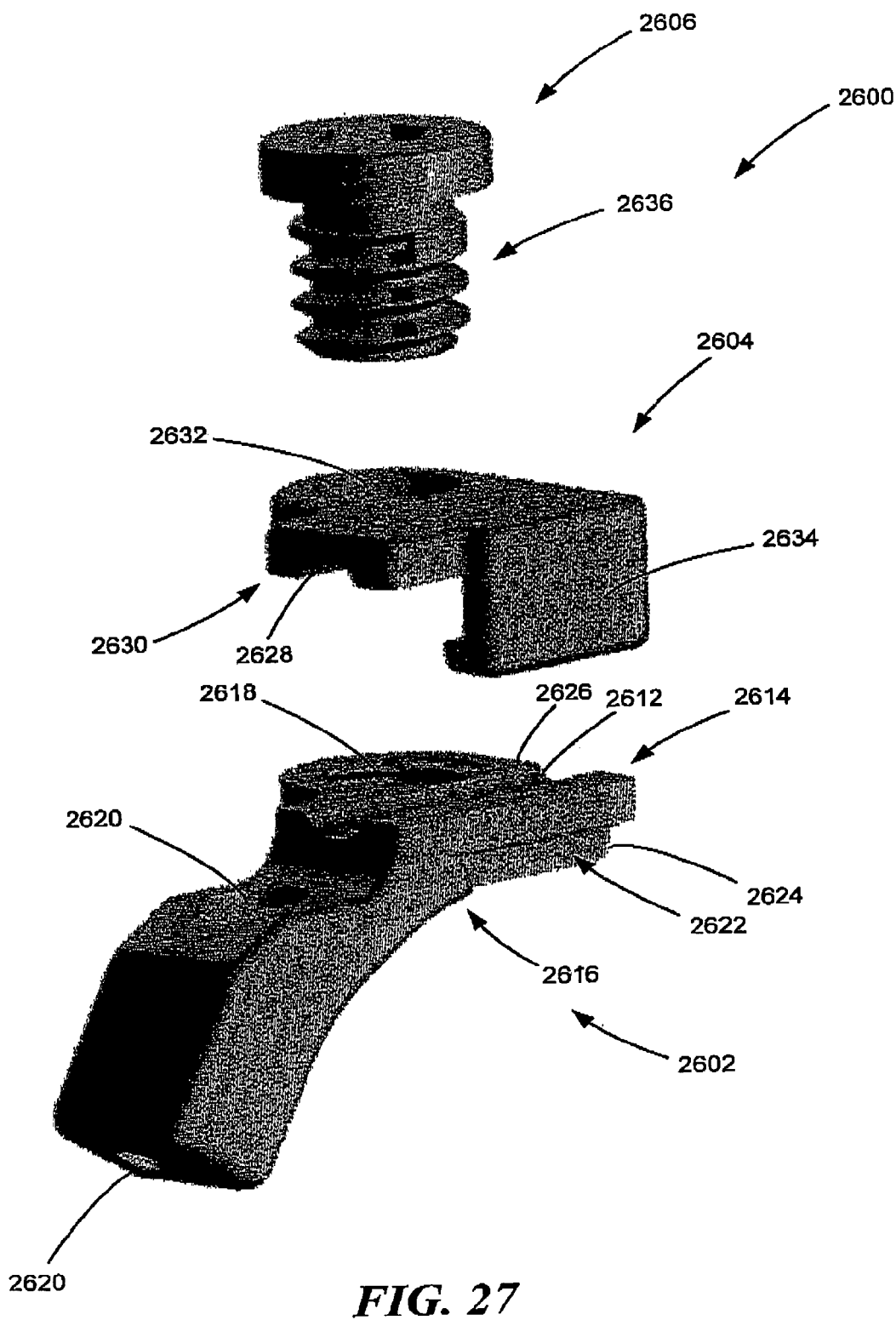
FIG. 27 is an exploded perspective view of the surgical cable clamp shown in FIG. 26.
Figure 28:
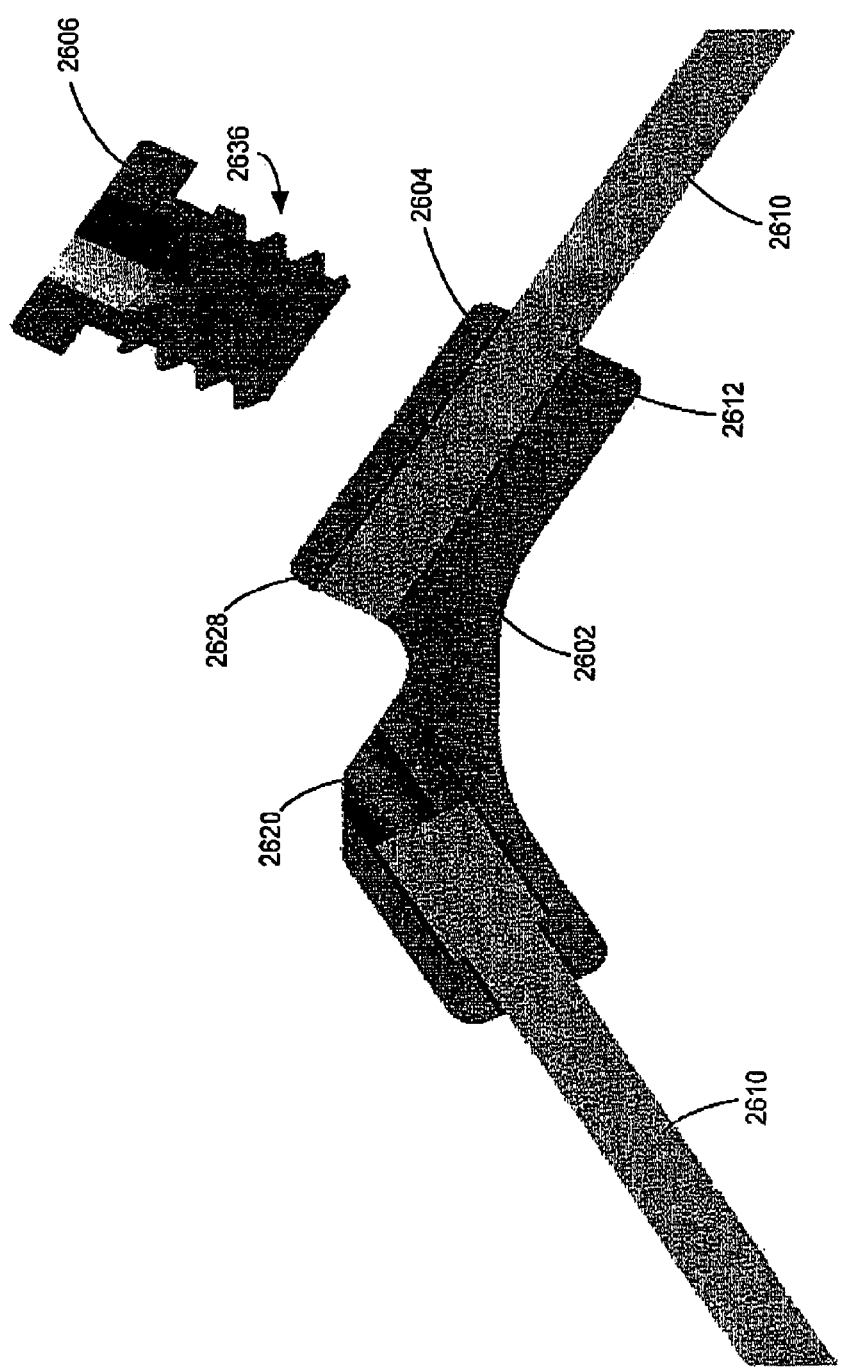
FIG. 28 is a cross-sectional side view of the surgical cable clamp shown in FIG. 26.

FIGS. 26-28 illustrate a surgical cable clamp in accordance with various embodiments of the invention. FIG. 26 is a perspective view of a structure of a surgical cable clamp in accordance with various embodiments of the invention. The cable clamp 2600 includes a clamping body 2602, a clamping mechanism 2604, and a force application member 2606. A preferred environment for the cable clamp 2600 is a portion of a patient's body such as a bone 2608 in conjunction with an orthopedic surgical cable 2610 for use in a surgical procedure. Typically, the orthopedic surgical cable 2610 is adapted to be installed relative to a bone in a patient, in order to apply a force to the bone. The force applied to the bone or portion of a patient's body can be tension or compression. In the embodiment shown here, the force applied to the patient's bone is compression. Similar to other embodiments of the invention described above, the surgical cable clamp 2600 can be a stand alone-type clamp for securing the position of an orthopedic surgical cable 2610 relative to a portion of a patient's body such as a patient's bone 2610. Alternatively, an embodiment of the surgical cable clamp 2600 can also be a device-incorporated clamp, similar to the embodiment shown in FIGS. 4a-b, for securing the position of an orthopedic surgical cable 2610 relative to a portion of a prefabricated orthopedic device such as a trochanteric grip and a patient's bone 2610. The device-incorporated clamp utilizes a portion of the trochanteric grip or other prefabricated orthopedic device for clamping the orthopedic surgical cable 2610.

In many embodiments, one or more orthopedic surgical cables 2610 can be utilized to secure a prefabricated orthopedic device such as a trochanteric grip into a position relative to an end of a patient's bone 2608. When a force is applied to a surgical cable clamp 2600, the surgical cable clamp 2600 compresses the orthopedic surgical cable 2610, thus securing the orthopedic surgical cable 2610 into a position relative to the prefabricated orthopedic device such as a trochanteric grip and patient's bone.

If necessary, the orthopedic surgical cable 2610 can be loosened or otherwise retensioned by applying another force to the surgical cable clamp 2600 to relieve the compression force on the orthopedic surgical cable 2610 applied by the surgical cable clamp 2600. The orthopedic surgical cable 2610 can then be retensioned by hand or by way of a tensioning device (not shown) so that the orthopedic surgical cable 2610 is at a desired tension or position. Yet another force can then be applied to the surgical cable clamp 2600 to create another compression force on the orthopedic surgical cable 2610 which can then maintain the desired tension or position of the orthopedic surgical cable 2610. Depending upon the location of the orthopedic surgical cable 2610 relative to the prefabricated orthopedic device such as a trochanteric grip and the patient's bone 2610, either and/or both the stand alone-type clamp or the device-incorporated clamp may be used to secure the position and tension of the orthopedic surgical cable 2610 as shown.

The surgical cable clamp 2600 shown in FIGS. 26-29 also provides clamping and reclamping of an orthopedic surgical cable without twisting or nonalignment of the clamp 2600 relative to the orthopedic surgical cable. As described in greater detail below, orientation of the orthopedic surgical cable with respect to the clamp 2600 permits the orthopedic surgical cable to be gripped by the clamp 2600 and the cable tensioned without causing twisting or nonalignment of the clamp 2600 relative to the orthopedic surgical cable. Furthermore, orientation of the orthopedic surgical cable with respect to the clamp 2600 permits the orthopedic surgical cable to be subsequently tensioned and secured by the clamp 2600 at a second tension without loss of tension due to twisting or nonalignment of the clamp 2600 relative to the orthopedic surgical cable.

FIG. 27 is an exploded perspective view of the surgical cable clamp shown in FIG. 26. FIG. 28 is a cross-sectional side view of the surgical cable clamp shown in FIG. 26. Generally, the clamping body 2602 is adapted to restrain a first portion of the orthopedic surgical cable 2610 to the clamping body 2602. The clamping body 2602 includes a cable channel 2612 in an upper surface 2614, an opposing lower surface 2616, a threaded force application member receiving hole 2618, a cable hole 2620, and a groove 2622 in a side surface 2624. The cable channel 2612 includes at least one ridge 2626 that can grip a portion of an associated orthopedic surgical cable 2608 between the clamping body 2602 and clamping mechanism 2604. The opposing lower surface 2616 mounts to a portion of a patient's body such as a bone 2608.

Typically, the clamping mechanism 2604 is adapted to cooperate with the clamping body 2602 to capture a second portion of the orthopedic surgical cable 2610 between the clamping mechanism 2604 and the clamping body 2602. The clamping mechanism 2604 includes a cable channel 2628 in a lower surface 2630, a force application member receiving hole 2632, and an arm 2634 adapted to engage the groove 2622 in the side surface 2624 of the clamping body 2602. The clamping body 2602 and clamping mechanism 2604 correspondingly fit together so that the arm 2634 of the clamping mechanism 2604 engages the groove 2622 in the side surface 2624 of the clamping body 2602, and the cable channels 2612, 2628 of the respective clamping body 2602 and clamping mechanism 2604 correspondingly mate together to accommodate a portion of the orthopedic surgical cable 2610 between the clamping body 2602 and clamping mechanism 2604. The cable channel 2628 includes at least one ridge (not shown) similar to ridge 2626 that can grip a portion of an associated orthopedic surgical cable 2610 between the clamping body 2602 and clamping mechanism 2604.

Note that in some embodiments in accordance with the invention, the clamping body 2602 and clamping mechanism 2604 can be integrated into a single piece similar to that shown in FIGS. 1B and 1C. In other embodiments, the clamping body 2602 may be incorporated into an orthopedic device such as a bone plate or trochanteric grip similar to those shown in FIGS. 1B and 1C. Alternatively, the clamping mechanism 2604 may be incorporated into an orthopedic device such as a bone plate or trochanteric grip similar to those shown in FIGS. 1B and 1C.

The force application member 2606 connects to the clamping body 2602 and clamping mechanism 2604. Generally, the force application member 2606 is adapted to be rotated or otherwise manipulated in order to force the clamping body 2602 and clamping mechanism 2604 to grip the second portion of the orthopedic surgical cable 2610 in a manner whereby the force and consequent gripping are subject to gradual control by rotation or manipulation of the force application member 2606 and the gripping does not cause twisting or nonalignment of the clamp 2600 relative to the orthopedic surgical cable 2610. For example, the force application member 2606 can be adapted to force the clamping body 2602 and clamping mechanism 2604 towards each other. Alternatively, the force application member 2606 can be adapted to force the clamping body 2602 and clamping mechanism 2604 apart or away from each other.

The force application member 2606 shown in this embodiment includes a threaded portion 2636 along a portion of the member 2606. Other embodiments of a force application member in accordance with the invention can be threadless. The force application member receiving hole 2618 of the clamping body 2602 and the force application member receiving hole 2632 of the clamping mechanism 2604 can each include a respective threaded portion (not shown) that is adapted to receive the threaded portion 2636 of the force application member 2606. The force application member 2606 connects to the respective force application member receiving holes 2618, 2632 of the clamping body 2602 and clamping mechanism 2604. When rotated or otherwise manipulated, the force application member 2606 forces the clamping body 2602 and clamping mechanism 2604 to grip the portion of cable 2610 within the cable channels 2612, 2628 and between the clamping body 2602 and clamping mechanism 2604. Preferably, at least a portion of either or both of the receiving holes 2618, 2632 includes a threaded portion (not shown) adapted to permit the force application member 2606 to force the clamping body 2602 and clamping mechanism 2604 to grip the portion of cable 2610 within the cable channels 2612, 2628 and between the clamping body 2602 and clamping mechanism 2604. In most embodiments, the orthopedic surgical cable 2610 and clamp 2600 are adapted to allow the orthopedic surgical cable 2610 to be tensioned and secured by the clamp 2600 at a first tension, and further adapted to allow the orthopedic surgical cable 2610 to be subsequently tensioned and secured by the clamp 2600 at a second tension without loss of tension due to twisting or nonalignment of the clamp 2600 relative to the orthopedic surgical cable 2610.

In alternative embodiments, different configurations of a force application member can be used in lieu of the force application member 2606 shown in this embodiment. In alternative embodiments, a force application member is typically made from a material having elastic-like or shape-memory properties, such as nitinol, a memory metal, a material activated by temperature change or heat, a material activated by a force, a material activated by an electrical current, or a material activated by a magnetic force. Other metals, plastics, alloys, composites, or other materials can be used within a clamping mechanism to provide the desired effects. Examples of a force application member are similar to those disclosed in U.S. patent application Ser. No. 10/230,040, the contents of which have incorporated herein by reference. Generally, the force application member connects to the clamping body 2602 and clamping mechanism 2604. The force application member is adapted to be activated in order to force the clamping body 2602 and clamping mechanism 2604 to grip first and second portions of the orthopedic surgical cable 2610 in a manner whereby the force and consequent gripping are subject to gradual control by the force application member and the gripping does not cause twisting or nonalignment of the clamp 2600 relative to the orthopedic surgical cable 2610.

FIGS. 29*a*-*c* illustrate a surgical procedure to use the cable clamp 2600 of FIGS. 26-28. The procedure illustrated in FIGS. 29*a*-*c* is similar to the procedure illustrated in FIGS. 3*a*-*c*. The particular embodiment shown in the sequence of FIGS. 29*a*-*c* utilizes a stand alone-type surgical cable clamp, shown in FIG. 26 as 2600. Other embodiments of a surgical cable clamp 2600, such as a device-incorporated surgical cable clamp, can be utilized with a method similar to that illustrated in FIGS. 5*a*-*d*.

In FIG. 29*a*, a surgical cable clamp 2700 in accordance with the invention is shown adjacent to an orthopedic device such as a trochanteric grip 2702. The trochanteric grip 2702 is aligned with a proximal end of a patient's femur bone 2704 in accordance with a hip replacement procedure. When the trochanteric grip 2702 is to be secured to the patient's femur 2704, the surgical cable clamp 2700 is positioned in a desired position adjacent to the trochanteric grip 2702 to receive an orthopedic surgical cable 2706. Typically, the surgical cable clamp 2700 is preassembled prior to the sequence, and mounted relative to a bone in a patient's body. Similar to the cable clamp in FIGS. 26-28, the surgical cable clamp 2700 includes a clamping body 2708, a force application member 2710, and a clamping mechanism 2712, and can be preassembled as described in FIGS. 26-28. A first portion of the orthopedic surgical cable 2706 is restrained relative to the clamping body 2702. Typically, a relatively smaller diameter end 2714 of a predetermined length of surgical cable 2706 is inserted into and pulled through a first cable hole 2716 or channel of the surgical cable clamp 2700 formed by the assembly and alignment of the clamping body 2708 with the clamping mechanism 2712. A bead 2718 on a relatively larger diameter end of the surgical cable 2706 restrains the relatively larger diameter end of surgical cable 2706 adjacent to the surgical cable clamp 2700 when the length of the surgical cable 2706 is pulled through the first cable hole 2716 or channel. Note that the bead 2718 can be preformed by severing or melting a portion of the cable with an arc, and forming the bead at the end of the cable while the severed or melted cable remains hot. This procedure provides a bead of consistent size and placement relative to the centerline of the cable. Other shapes or configurations of a bead, such as a fitting, can be utilized in accordance with various embodiments of the invention.

As shown in FIG. 29*b*, the relatively smaller diameter end 2714 of the surgical cable 2706 is inserted through a cable hole 2720 or channel in the trochanteric grip 2702 and wrapped around the thickness of the patient's femur 2704. When the relatively smaller diameter end 2714 of the surgical cable 2706 is nearly around the patient's femur 2704, the relatively smaller diameter end 2714 is inserted through a second cable hole 2722 or channel of the surgical cable clamp 2700.

A second portion of the orthopedic surgical cable 2706 is captured between the clamping mechanism 2704 and the clamping body 2702. As shown in FIGS. 29*b*-*c*, the relatively smaller diameter end 2714 of the surgical cable 2706 is manually pulled through the second cable hole 2722 or channel with a cable tensioning device (not shown) until a desired tension in the surgical cable 2706 is attained. The force application member 2710 is connected to the clamping body 2702 and the clamping mechanism 2704 via a series of respective force application member holes 2724, 2726 in each of the clamping body 2702 and the clamping mechanism 2704. When the surgical cable 2706 is pulled to a desired tension, the force application member 2710 is tightened or otherwise rotated or manipulated in a first direction with a hexagonal-shaped tightening instrument (not shown) until the second portion of the orthopedic surgical cable 2706 is gripped between the clamping body 2702 and clamping mechanism 2704 so that the gripping is subject to gradual control by rotation or manipulation of the force application member 2710 and the gripping does not cause twisting or nonalignment of the clamp 2700 relative to the orthopedic surgical cable 2706, thus creating a first tension in the orthopedic surgical cable 2700. Any excess length of surgical cable can be trimmed with a cutting instrument (not shown).

In some instances, a cable tensioning device (not shown) can be used to tighten the surgical cable 2706 to a predetermined tension. A tightening instrument with a corresponding hexagonal-shaped head or driver such as a "T-handled driver" with a hex head to match the shape of the clamping bolt can then be used to tighten the force application member 2710 to a preset torque while measuring the tension on the surgical cable with the cable tensioning device as the force application member 2710 is tightened. A suitable cable tensioning device can be a device or system that applies a tension to a surgical cable, maintains the tension on the surgical cable until the tightening instrument can be used to tighten the clamping bolt of the surgical cable clamp, measures the tension in the surgical cable, and releases the surgical cable when the clamping bolt has secured the surgical cable.

If desired, the first tension in the orthopedic surgical cable 2706 can be released by rotating or manipulating the force application member in an opposing direction to the first direction so that the orthopedic surgical cable can be repositioned between the clamping mechanism and the clamping body. The second portion of the orthopedic surgical cable is gripped between the clamping body and clamping mechanism by rotating or manipulating the threaded force application member in the first direction so that consequent gripping is subject to gradual control by rotation or manipulation of the force application member and the gripping does not cause twisting or nonalignment of the clamp relative to the orthopedic surgical cable, thus creating a second tension in the orthopedic surgical cable.

More than one surgical cable 2706 may be needed to secure an orthopedic device such as a trochanteric grip 2702 or bone plate to a patient's femur 2704. The above sequence can repeat as needed until the trochanteric grip or other orthopedic device is secured to the patient's femur or bone. After tensioning one or more surgical cables 2706 to the patient's femur with one or more corresponding surgical cable clamps 2700, previously tensioned surgical cables may tend to loosen or otherwise require additional tension to sufficiently secure the orthopedic device such as a trochanteric grip 2702 to the patient's femur 2704.

If necessary, the tension on a previously tensioned surgical cable can be released by applying an untightening force to the force application member 2710 with the hexagonal-shaped tightening instrument, releasing the compression force between the clamping body 2708 and clamping mechanism 2712, thus releasing the compression and tension on the surgical cable 2706. The surgical cable 2706 is then retensioned manually or by use of the cable tensioning device. When the desired tension is reached, a tightening force is applied to the force application member 2710 in order to create a sufficient compression force between the clamping body 2708 and the clamping mechanism 2712 to maintain the desired tension in the surgical cable 2706, and secure the position of the surgical cable 2706 relative to the surgical cable clamp 2700.

Tensioning and retensioning of one or more surgical cables 2706 may occur more than once during a surgical procedure until all of the surgical cables 2706 are sufficiently tensioned to maintain the position of the surgical cables 2706, bone plate and or trochanteric grip 2702 relative to the patient's femur 2704. The sequence described above with respect to FIGS. 29a-c can be repeated as necessary to accomplish this.

Preferably, the surgical cable clamp 2700 illustrated in FIGS. 29a-c and in other figures can be preassembled prior to installation or use. Preassembly of a surgical cable clamp can include assembling component parts of the surgical cable clamp together with, or without, an orthopedic surgical cable so that a user such as a surgeon can rapidly install or use the surgical cable clamp. In many cases, preassembly of the surgical cable clamp with an orthopedic surgical cable saves time during a surgical procedure when installing or using the surgical cable clamp.

While the above description contains many specifics, these specifics should not be construed as limitations on the scope of the invention, but merely as exemplifications of the disclosed embodiments. Those skilled in the art will envision many other possible variations that within the scope of the invention as defined by the claims appended hereto.

We claim:

1. A surgical method for reclamping a surgical cable clamp with an orthopedic surgical cable without substantially deforming the orthopedic surgical cable for installation with respect to a patient's body, comprising:

providing an orthopedic surgical cable and a surgical cable clamp, the surgical cable clamp comprising a clamping body, a clamping mechanism, and a force application member;

mounting the surgical cable clamp relative to a bone in a patient's body;

restraining a first portion of the orthopedic surgical cable relative to the clamping body;

capturing a second portion of the orthopedic surgical cable between the clamping mechanism and the clamping body, wherein the orthopedic surgical cable is wrapped around an entire circumference of the bone;

connecting the force application member to the clamping body and the clamping mechanism;

gripping the second portion of the orthopedic surgical cable between the clamping body and clamping mechanism by manipulating the force application member in a first direction so that the gripping is subject to gradual control by manipulation of the force application member and the gripping does not cause nonalignment of the clamp relative to the orthopedic surgical cable, thus maintaining a first tension in the orthopedic surgical cable;

releasing the first tension in the orthopedic surgical cable by manipulating the force application member in an opposing direction to the first direction so that the orthopedic surgical cable can be repositioned between the clamping mechanism and the clamping body; and gripping the second portion of the orthopedic surgical cable between the clamping body and clamping mechanism by manipulating the force application member in the first direction so that consequent gripping is subject to gradual control by manipulation of the force application member and the gripping does not cause nonalignment of the clamp relative to the orthopedic surgical cable, thus maintaining a second tension in the orthopedic surgical cable.

2. The method of claim 1, wherein securing a first portion of the orthopedic surgical cable relative to the clamping body further comprises:

restraining a larger end of the cable with the clamping body.

3. The method of claim 2, wherein the larger end of the cable is a fitting mounted to an end of the cable.

4. The method of claim 1, wherein the surgical cable clamp is incorporated into a prefabricated device selected from a group consisting of: an orthopedic device, a bone plate, or a trochanteric grip.

5. The method of claim 1, wherein the surgical cable clamp is a stand alone type device.

6. The method of claim 1, wherein gripping the second portion of the orthopedic surgical cable between the clamping body and clamping mechanism by manipulating the force application member in a first direction so that the gripping is subject to gradual control by manipulation of the force application member, further comprises:

forcing the clamping body and clamping mechanism apart from each other.

7. The method of claim 1, wherein gripping the second portion of the orthopedic surgical cable between the clamping body and clamping mechanism by manipulating the force application member in a first direction so that the gripping is subject to gradual control by manipulation of the force application member, further comprises:

forcing the clamping body and clamping mechanism towards each other.

8. A surgical method for reclamping a surgical cable clamp with an orthopedic surgical cable without substantially deforming the orthopedic surgical cable for installation with respect to a patient's body, comprising:

providing an orthopedic surgical cable and a surgical cable clamp, the surgical cable clamp comprising a clamping body, a clamping mechanism, and a force application member;

mounting the clamping body to a bone in a patient's body;

connecting a first portion of the orthopedic surgical cable to the clamping body;

wrapping a portion of the orthopedic surgical cable around a part of a patient's bone;

connecting a second portion of the orthopedic surgical cable to the clamping body;

capturing the first portion and second portion of the orthopedic surgical cable between the clamping body and clamping mechanism, wherein the orthopedic surgical cable is wrapped around an entire circumference of the patient's bone;

connecting the force application member to the clamping body and clamping mechanism;

gripping the first and second portions of the orthopedic surgical cable between the clamping body and the clamping mechanism by manipulating the force application member in a first direction so that the consequent gripping is subject to gradual control by the force application member and the gripping does not cause nonalignment of the clamp relative to the orthopedic surgical cable, thus maintaining a first tension in the orthopedic surgical cable;

releasing the first tension in the orthopedic surgical cable by manipulating the force application member in a second direction so that the orthopedic surgical cable can be repositioned between the clamping mechanism and the clamping body; and gripping the first and second portions of the orthopedic surgical cable between the clamping body and the clamping mechanism by manipulating the force application member in the first direction so that the consequent gripping is subject to gradual control by the force application member and the gripping does not cause nonalignment of the clamp relative to the orthopedic surgical cable, thus maintaining a second tension in the orthopedic surgical cable.

9. The method of claim 8, wherein connecting a first portion of the orthopedic surgical cable to the clamping body further comprises:

restraining a larger end of the cable with the clamping body.

10. The method of claim 9, wherein the larger end of the cable is a fitting mounted to an end of the cable.

11. The method of claim 8, wherein the surgical cable clamp is incorporated into a prefabricated device selected from a group consisting of: an orthopedic device, a bone plate, or a trochanteric grip.

12. The method of claim 8, wherein the surgical cable clamp is a stand alone type device.

13. The method of claim 8, wherein gripping the first and second portions of the orthopedic surgical cable between the clamping body and the clamping mechanism by manipulating the force application member in a first direction so that the consequent gripping is subject to gradual control by the force application member and the gripping does not cause nonalignment of the clamp relative to the orthopedic surgical cable, further comprises:

forcing the clamping body and clamping mechanism apart from each other.

14. The method of claim 8, wherein gripping the first and second portions of the orthopedic surgical cable between the clamping body and the clamping mechanism by manipulating the force application member in a first direction so that the consequent gripping is subject to gradual control by the force application member and the gripping does not cause nonalignment of the clamp relative to the orthopedic surgical cable, further comprises:

forcing the clamping body and clamping mechanism towards each other.

15. A surgical method for reclamping a surgical cable clamp with an orthopedic surgical cable without substantially deforming the orthopedic surgical cable for installation with respect to a patient's body, comprising:

providing an orthopedic surgical cable and a surgical cable clamp, the surgical cable clamp comprising a clamping body, a clamping mechanism, and a force application member;

mounting the surgical cable clamp to a bone in the patient's body;

restraining a first portion of the orthopedic surgical cable with the surgical cable clamp;

wrapping a portion of the orthopedic surgical cable around a part of the patient's bone;

capturing an extended portion of the orthopedic surgical cable between the clamping body and the clamping mechanism, wherein the orthopedic surgical cable is wrapped around an entire circumference of the patient's bone;

gripping the extended portion of the orthopedic surgical cable between the clamping body and the clamping mechanism by activating the force application member, wherein the force application member connects to the clamping body and clamping mechanism, so that the consequent gripping is subject to gradual control by the force application member and the gripping does not cause nonalignment of the clamp relative to the orthopedic surgical cable, thus maintaining a first tension in the orthopedic surgical cable;

deactivating the force application member so that the first tension can be released and the orthopedic surgical cable can be repositioned between the clamping mechanism and the clamping body; and gripping the extended portion of the orthopedic surgical cable between the clamping body and the clamping mechanism together by activating the force application member so that the clamping body and clamping mechanism grip the extended portion of the orthopedic surgical cable in a manner whereby the force and consequent gripping are subject to gradual control by the force application member and the gripping does not cause nonalignment of the clamp relative to the orthopedic surgical cable, thus maintaining a second tension in the orthopedic surgical cable.

16. The method of claim 15, wherein:

the force application member is adapted to force the clamping body and clamping mechanism towards each other.

17. The method of claim 15, wherein:

the force application member is adapted to force the clamping body and clamping mechanism apart from each other.

18. The method of claim 15, wherein:

the force application member is selected from a group consisting of: an elastic member, a shape-memory member, a memory metal member, a heat activated member, a force activated member, an electrically-activated member, and a magnetically-activated member.

19. A surgical method for reclamping a surgical cable clamp with an orthopedic surgical cable without substantially deforming the orthopedic surgical cable for installation of a device with respect to a patient's body, comprising:

providing a device, an orthopedic surgical cable, and a surgical cable clamp, wherein the surgical cable clamp includes a clamping body, a mechanism, and a threaded force application member;

restraining a first portion of the orthopedic surgical cable to a device;

mounting the device to a part of the patient's body;

wrapping an extended portion of the orthopedic surgical cable around an entire circumference of a bone in the patient's body;

capturing the extended portion of the orthopedic surgical cable between the surgical cable clamp and device;

connecting the threaded force application member to the clamping body and clamping mechanism;

gripping the extended portion of the orthopedic surgical cable between the surgical cable clamp and device by manipulating the threaded force application member in a first direction so that the surgical cable clamp and device grip the extended portion of the orthopedic surgical cable in a manner whereby the consequent gripping is subject to gradual control by the threaded force application member and the gripping does not cause nonalignment of the clamp relative to the orthopedic surgical cable, thus maintaining a first tension in the orthopedic surgical cable;

releasing the first tension in the orthopedic surgical cable by manipulating the threaded force application member in a second direction so that the first tension can be released and the orthopedic surgical cable can be repositioned between the surgical cable clamp and device; and gripping the extended portion of the orthopedic surgical cable between the surgical cable clamp and device together by manipulating the threaded force application member in the first direction so that the surgical cable clamp and device grip the orthopedic surgical cable in a manner whereby consequent gripping is subject to gradual control by the threaded force application member and the gripping does not cause nonalignment of the clamp relative to the orthopedic surgical cable, thus maintaining a second tension in the orthopedic surgical cable.

20. The method of claim 19, wherein the device is selected from a group consisting of: an orthopedic device, a bone plate, and a trochanteric grip.

21. The method of claim 19, wherein the surgical cable clamp is incorporated into a prefabricated orthopedic device.

22. The method of claim 19, wherein the surgical cable clamp is a stand alone type device.

* * * * *